United States Patent
Ko et al.

(10) Patent No.: US 12,338,468 B2
(45) Date of Patent: Jun. 24, 2025

(54) SUCROSE INVERTASE VARIANTS

(71) Applicant: Corbion Biotech, Inc., South San Fransisco, CA (US)

(72) Inventors: Nien-Hsi Ko, South San Fransisco, CA (US); Janice Lau Wee, South San Fransisco, CA (US); Douglas A. Hattendorf, South San Fransisco, CA (US)

(73) Assignee: Corbion Biotech, Inc., South San Francisco, CA (US)

( * ) Notice: Subject to any disclaimer, the term of this patent is extended or adjusted under 35 U.S.C. 154(b) by 452 days.

(21) Appl. No.: 17/777,711

(22) PCT Filed: Nov. 19, 2020

(86) PCT No.: PCT/US2020/061280
§ 371 (c)(1),
(2) Date: May 18, 2022

(87) PCT Pub. No.: WO2021/102139
PCT Pub. Date: May 27, 2021

(65) Prior Publication Data
US 2023/0037413 A1      Feb. 9, 2023

Related U.S. Application Data

(60) Provisional application No. 62/961,986, filed on Jan. 16, 2020, provisional application No. 62/937,849, filed on Nov. 20, 2019.

(51) Int. Cl.
*C12N 9/26*    (2006.01)
*C12P 19/12*   (2006.01)

(52) U.S. Cl.
CPC ............ *C12N 9/2431* (2013.01); *C12P 19/12* (2013.01); *C12Y 302/01026* (2013.01)

(58) Field of Classification Search
CPC .................. C12N 9/2431; C12P 19/12; C12Y 302/01026
See application file for complete search history.

(56) References Cited

U.S. PATENT DOCUMENTS

| | | |
|---|---|---|
| 7,883,882 B2 | 2/2011 | Franklin et al. |
| 8,476,059 B2 | 7/2013 | Trimbur et al. |
| 8,592,188 B2 | 11/2013 | Franklin et al. |
| 8,846,352 B2 | 9/2014 | Chua et al. |

(Continued)

FOREIGN PATENT DOCUMENTS

| CN | 110078832 A | * | 8/2019 | ............. C07K 16/18 |
|---|---|---|---|---|
| WO | WO 2011/034863 A1 | | 3/2011 | |

(Continued)

OTHER PUBLICATIONS

P10594, 1989, UniProt database. (Year: 1989).*

(Continued)

*Primary Examiner* — M Franco G Salvoza
*Assistant Examiner* — Naghmeh Nina Moazzami
(74) *Attorney, Agent, or Firm* — Sunit Talapatra; Foley & Lardner LLP

(57) ABSTRACT

The present disclosure provides sucrose invertase variants having an enhanced ability to hydrolyze sucrose into glucose and fructose and related methods and compositions.

19 Claims, 8 Drawing Sheets

Specification includes a Sequence Listing.

Percentage of sucrose inverted relative to control with single copy of wild-type ScSUC2 gene (at 28°C, pH7)

(56) References Cited

U.S. PATENT DOCUMENTS

| | | |
|---|---|---|
| 9,328,351 B2 | 5/2016 | Franklin et al. |
| 9,649,368 B2 | 5/2017 | Franklin et al. |
| 10,053,715 B2 | 8/2018 | Franklin et al. |
| 10,125,382 B2 | 11/2018 | Casolari et al. |
| 10,287,613 B2 | 5/2019 | Franklin et al. |
| 10,316,299 B2 | 6/2019 | Davis et al. |
| 2008/0292918 A1 | 11/2008 | Finnerty et al. |
| 2009/0282545 A1 | 11/2009 | Eichelberger et al. |
| 2010/0297749 A1 | 11/2010 | Aravanis et al. |
| 2011/0045563 A1 | 2/2011 | Melis |
| 2011/0111413 A1 | 5/2011 | Padgett et al. |
| 2012/0288930 A1 | 11/2012 | Trimbur et al. |
| 2014/0068797 A1 | 3/2014 | Doudna et al. |
| 2014/0178950 A1 | 6/2014 | Franklin et al. |
| 2014/0315985 A1 | 10/2014 | May et al. |
| 2016/0168618 A1 | 6/2016 | Kim et al. |

FOREIGN PATENT DOCUMENTS

| | | |
|---|---|---|
| WO | WO 2011/150410 A2 | 12/2011 |
| WO | WO 2011/150411 A2 | 12/2011 |
| WO | WO 2015/012533 A1 | 1/2015 |
| WO | WO 2018/067849 A2 | 4/2018 |

OTHER PUBLICATIONS

English translation of CN-110078832-A (Year: 2019).*
Barbosa et al., "Biochemical characterization and evaluation of invertases produced from *Saccharomyces cerevisiae* CAT-1 and *Rhodotorula mucilaginosa* for the production of fructooligosaccharides", *Preparative Biochemistry and Biotechnology*, vol. 48, No. 6, pp. 506-513 (2018).
Berka et al., "The development of gene expression systems for filamentous fungi", *Biotechnology Advances*, vol. 7, No. 2, pp. 127-154 (1989).
Gustafsson et al., "Codon bias and heterologous protein expression", *Trends in Biotechnology*, vol. 22, pp. 346-353 (2004).
Hawkins et al., "Expression of Human Growth Hormone by the Eukaryotic Alga, *Chorella*", *Current Microbiology*, vol. 38, pp. 335-341 (1999).
International Search Authority, International Search Report in International Patent Application No. PCT/US2020/061280, mailed on Mar. 12, 2021.
International Search Authority, Written Opinion in International Patent Application No. PCT/US2020/061280, mailed on Mar. 12, 2021.
Jansen et al., "Revisiting the codon adaptation index from a whole-genome perspective: analyzing the relationship between gene expression and codon occurrence in yeast using a variety of models", *Nucleic Acids Research*, vol. 31, No. 8, pp. 2242-2251 (2003).
Jinek et al., "A programmable dual-RNA-guided DNA endonuclease in adaptive bacterial immunity", *Science*, vol. 337, pp. 816-821 (2012).
Lafraya et al., "Fructo-Oligosaccharide Synthesis by Mutant Versions of *Saccharomyces cerevisiae* Invertase", *Applied and Environmental Microbiology*, vol. 77, No. 17, p. 6148-6157 (2011).
Lindberg et al., "Engineering a platform for photosynthetic isoprene production in cyanobacteria, using *Synechocystis* as the model organism", *Metabolic Engineering*, vol. 12, Issue 1, pp. 70-79 (2010).
Miao et al., "High yield bio-oil production from fast pyrolysis by metabolic controlling of *Chlorella protothecoides*", *Journal of Biotechnology*, vol. 110, Issue 1, pp. 85-93 (2004).
Miao et al., "Biodiesel production from heterotrophic microalgal oil", *Bioresource Technology*, vol. 97, p. 841-846 (2006).
Nadeem et al., "Microbial inversases: A review on kinetics, thermodynamics, psysiochemical properties", *Process Biochemistry*, vol. 50, No. 8, pp. 1202-1210 (2015).
Needleman et al., "A General Method Applicable to the Search for Similarities in the Amino Acid Sequence of Two Proteins", *Journal of Molecular Biology*, vol. 48, Issue 3, pp. 443-453 (1970).
Ran et al., "In vivo genome editing using *Staphylococcus aureus* Cas9", *Nature*, vol. 520, No. 7546, pp. 186-191 (2015).
Romanos et al., "Foreign Gene Expression in Yeast: a Review", *Yeast*, vol. 8, No. 6, pp. 423-488 (1992).
Sanjay et al., "Enhanced pH and thermal stabilities of invertase immobilized on montmorillonite K-10", *Food Chemistry*, vol. 94, No. 4, pp. 573-579 (2006).
Sharp et al., "The codon Adaptation Index—a measure of directional synonymous codon usage bias, and its potential applications", *Nucleic Acids Research*, vol. 15, Issue 3, pp. 1281-1295 (1987).
Villalobos et al., "Gene Designer: a synthetic biology tool for constructing artificial DNA segments", *BMC Bioinformatics*, vol. 7, No. 285, pp. 1-8 (2006).
Welch et al., "Design Parameters to Control Synthetic Gene Expression in *Escherichia coli*", *PLOS One*, vol. 4, Issue 9, p. e7002 (2009).
Wu et al., "SGDB: a database of synthetic genes re-designed for optimizing protein over-expression", *Nucleic Acids Research*, vol. 35, Issue suppl_1, pp. D76-79 (2007).

* cited by examiner

SEQUENCE LISTING

<160> NUMBER OF SEQ ID NOS: 18

<210> SEQ ID NO 1
<211> LENGTH: 532
<212> TYPE: PRT
<213> ORGANISM: Saccharomyces cerevisiae

<400> SEQUENCE: 1

```
Met Leu Leu Gln Ala Phe Leu Phe Leu Leu Ala Gly Phe Ala Ala Lys
1               5                   10                  15

Ile Ser Ala Ser Met Thr Asn Glu Thr Ser Asp Arg Pro Leu Val His
            20                  25                  30

Phe Thr Pro Asn Lys Gly Trp Met Asn Asp Pro Asn Gly Leu Trp Tyr
        35                  40                  45

Asp Glu Lys Asp Ala Lys Trp His Leu Tyr Phe Gln Tyr Asn Pro Asn
    50                  55                  60

Asp Thr Val Trp Gly Thr Pro Leu Phe Trp Gly His Ala Thr Ser Asp
65                  70                  75                  80

Asp Leu Thr Asn Trp Glu Asp Gln Pro Ile Ala Ile Ala Pro Lys Arg
                85                  90                  95

Asn Asp Ser Gly Ala Phe Ser Gly Ser Met Val Val Asp Tyr Asn Asn
            100                 105                 110

Thr Ser Gly Phe Phe Asn Asp Thr Ile Asp Pro Arg Gln Arg Cys Val
        115                 120                 125

Ala Ile Trp Thr Tyr Asn Thr Pro Glu Ser Glu Glu Gln Tyr Ile Ser
    130                 135                 140

Tyr Ser Leu Asp Gly Gly Tyr Thr Phe Thr Glu Tyr Gln Lys Asn Pro
145                 150                 155                 160

Val Leu Ala Ala Asn Ser Thr Gln Phe Arg Asp Pro Lys Val Phe Trp
                165                 170                 175

Tyr Glu Pro Ser Gln Lys Trp Ile Met Thr Ala Ala Lys Ser Gln Asp
            180                 185                 190

Tyr Lys Ile Glu Ile Tyr Ser Ser Asp Asp Leu Lys Ser Trp Lys Leu
        195                 200                 205

Glu Ser Ala Phe Ala Asn Glu Gly Phe Leu Gly Tyr Gln Tyr Glu Cys
    210                 215                 220

Pro Gly Leu Ile Glu Val Pro Thr Glu Gln Asp Pro Ser Lys Ser Tyr
225                 230                 235                 240

Trp Val Met Phe Ile Ser Ile Asn Pro Gly Ala Pro Ala Gly Gly Ser
                245                 250                 255

Phe Asn Gln Tyr Phe Val Gly Ser Phe Asn Gly Thr His Phe Glu Ala
            260                 265                 270

Phe Asp Asn Gln Ser Arg Val Val Asp Phe Gly Lys Asp Tyr Tyr Ala
        275                 280                 285
```

```
Leu Gln Thr Phe Phe Asn Thr Asp Pro Thr Tyr Gly Ser Ala Leu Gly
    290                 295                 300

Ile Ala Trp Ala Ser Asn Trp Glu Tyr Ser Ala Phe Val Pro Thr Asn
305                 310                 315                 320

Pro Trp Arg Ser Ser Met Ser Leu Val Arg Lys Phe Ser Leu Asn Thr
                325                 330                 335

Glu Tyr Gln Ala Asn Pro Glu Thr Glu Leu Ile Asn Leu Lys Ala Glu
                340                 345                 350

Pro Ile Leu Asn Ile Ser Asn Ala Gly Pro Trp Ser Arg Phe Ala Thr
            355                 360                 365

Asn Thr Thr Leu Thr Lys Ala Asn Ser Tyr Asn Val Asp Leu Ser Asn
    370                 375                 380

Ser Thr Gly Thr Leu Glu Phe Glu Leu Val Tyr Ala Val Asn Thr Thr
385                 390                 395                 400

Gln Thr Ile Ser Lys Ser Val Phe Ala Asp Leu Ser Leu Trp Phe Lys
                405                 410                 415

Gly Leu Glu Asp Pro Glu Glu Tyr Leu Arg Met Gly Phe Glu Val Ser
                420                 425                 430

Ala Ser Ser Phe Phe Leu Asp Arg Gly Asn Ser Lys Val Lys Phe Val
            435                 440                 445

Lys Glu Asn Pro Tyr Phe Thr Asn Arg Met Ser Val Asn Asn Gln Pro
    450                 455                 460

Phe Lys Ser Glu Asn Asp Leu Ser Tyr Tyr Lys Val Tyr Gly Leu Leu
465                 470                 475                 480

Asp Gln Asn Ile Leu Glu Leu Tyr Phe Asn Asp Gly Asp Val Val Ser
                485                 490                 495

Thr Asn Thr Tyr Phe Met Thr Thr Gly Asn Ala Leu Gly Ser Val Asn
                500                 505                 510

Met Thr Thr Gly Val Asp Asn Leu Phe Tyr Ile Asp Lys Phe Gln Val
            515                 520                 525

Arg Glu Val Lys
    530

<210> SEQ ID NO 2
<211> LENGTH: 532
<212> TYPE: PRT
<213> ORGANISM: artificial
<220> FEATURE:
<223> OTHER INFORMATION: ScSUC2 I17C mutant

<400> SEQUENCE: 2

Met Leu Leu Gln Ala Phe Leu Phe Leu Leu Ala Gly Phe Ala Ala Lys
1               5                   10                  15

Cys Ser Ala Ser Met Thr Asn Glu Thr Ser Asp Arg Pro Leu Val His
                20                  25                  30

Phe Thr Pro Asn Lys Gly Trp Met Asn Asp Pro Asn Gly Leu Trp Tyr
            35                  40                  45

Asp Glu Lys Asp Ala Lys Trp His Leu Tyr Phe Gln Tyr Asn Pro Asn
    50                  55                  60

Asp Thr Val Trp Gly Thr Pro Leu Phe Trp Gly His Ala Thr Ser Asp
65                  70                  75                  80

Asp Leu Thr Asn Trp Glu Asp Gln Pro Ile Ala Ile Ala Pro Lys Arg
                85                  90                  95

Asn Asp Ser Gly Ala Phe Ser Gly Ser Met Val Val Asp Tyr Asn Asn
            100                 105                 110
```

```
Thr Ser Gly Phe Phe Asn Asp Thr Ile Asp Pro Arg Gln Arg Cys Val
        115                 120                 125

Ala Ile Trp Thr Tyr Asn Thr Pro Glu Ser Glu Gln Tyr Ile Ser
130                 135                 140

Tyr Ser Leu Asp Gly Gly Tyr Thr Phe Thr Glu Tyr Gln Lys Asn Pro
145                 150                 155                 160

Val Leu Ala Ala Asn Ser Thr Gln Phe Arg Asp Pro Lys Val Phe Trp
                165                 170                 175

Tyr Glu Pro Ser Gln Lys Trp Ile Met Thr Ala Ala Lys Ser Gln Asp
                180                 185                 190

Tyr Lys Ile Glu Ile Tyr Ser Ser Asp Leu Lys Ser Trp Lys Leu
        195                 200                 205

Glu Ser Ala Phe Ala Asn Glu Gly Phe Leu Gly Tyr Gln Tyr Glu Cys
        210                 215                 220

Pro Gly Leu Ile Glu Val Pro Thr Glu Gln Asp Pro Ser Lys Ser Tyr
225                 230                 235                 240

Trp Val Met Phe Ile Ser Ile Asn Pro Gly Ala Pro Ala Gly Gly Ser
                245                 250                 255

Phe Asn Gln Tyr Phe Val Gly Ser Phe Asn Gly Thr His Phe Glu Ala
        260                 265                 270

Phe Asp Asn Gln Ser Arg Val Val Asp Phe Gly Lys Asp Tyr Tyr Ala
        275                 280                 285

Leu Gln Thr Phe Phe Asn Thr Asp Pro Thr Tyr Gly Ser Ala Leu Gly
        290                 295                 300

Ile Ala Trp Ala Ser Asn Trp Glu Tyr Ser Ala Phe Val Pro Thr Asn
305                 310                 315                 320

Pro Trp Arg Ser Ser Met Ser Leu Val Arg Lys Phe Ser Leu Asn Thr
                325                 330                 335

Glu Tyr Gln Ala Asn Pro Glu Thr Glu Leu Ile Asn Leu Lys Ala Glu
                340                 345                 350

Pro Ile Leu Asn Ile Ser Asn Ala Gly Pro Trp Ser Arg Phe Ala Thr
        355                 360                 365

Asn Thr Thr Leu Thr Lys Ala Asn Ser Tyr Asn Val Asp Leu Ser Asn
        370                 375                 380

Ser Thr Gly Thr Leu Glu Phe Glu Leu Val Tyr Ala Val Asn Thr Thr
385                 390                 395                 400

Gln Thr Ile Ser Lys Ser Val Phe Ala Asp Leu Ser Leu Trp Phe Lys
                405                 410                 415

Gly Leu Glu Asp Pro Glu Glu Tyr Leu Arg Met Gly Phe Glu Val Ser
                420                 425                 430

Ala Ser Ser Phe Phe Leu Asp Arg Gly Asn Ser Lys Val Lys Phe Val
            435                 440                 445

Lys Glu Asn Pro Tyr Phe Thr Asn Arg Met Ser Val Asn Asn Gln Pro
450                 455                 460

Phe Lys Ser Glu Asn Asp Leu Ser Tyr Tyr Lys Val Tyr Gly Leu Leu
465                 470                 475                 480

Asp Gln Asn Ile Leu Glu Leu Tyr Phe Asn Asp Gly Asp Val Val Ser
                485                 490                 495

Thr Asn Thr Tyr Phe Met Thr Gly Asn Ala Leu Gly Ser Val Asn
            500                 505                 510

Met Thr Thr Gly Val Asp Asn Leu Phe Tyr Ile Asp Lys Phe Gln Val
            515                 520                 525
```

Arg Glu Val Lys
    530

<210> SEQ ID NO 3
<211> LENGTH: 532
<212> TYPE: PRT
<213> ORGANISM: Artificial Sequence
<220> FEATURE:
<223> OTHER INFORMATION: ScSUC2 R28V mutant

<400> SEQUENCE: 3

Met Leu Leu Gln Ala Phe Leu Phe Leu Leu Ala Gly Phe Ala Ala Lys
1               5                   10                  15

Ile Ser Ala Ser Met Thr Asn Glu Thr Ser Asp Val Pro Leu Val His
            20                  25                  30

Phe Thr Pro Asn Lys Gly Trp Met Asn Asp Pro Asn Gly Leu Trp Tyr
        35                  40                  45

Asp Glu Lys Asp Ala Lys Trp His Leu Tyr Phe Gln Tyr Asn Pro Asn
    50                  55                  60

Asp Thr Val Trp Gly Thr Pro Leu Phe Trp Gly His Ala Thr Ser Asp
65                  70                  75                  80

Asp Leu Thr Asn Trp Glu Asp Gln Pro Ile Ala Ile Ala Pro Lys Arg
                85                  90                  95

Asn Asp Ser Gly Ala Phe Ser Gly Ser Met Val Val Asp Tyr Asn Asn
            100                 105                 110

Thr Ser Gly Phe Phe Asn Asp Thr Ile Asp Pro Arg Gln Arg Cys Val
        115                 120                 125

Ala Ile Trp Thr Tyr Asn Thr Pro Glu Ser Glu Glu Gln Tyr Ile Ser
    130                 135                 140

Tyr Ser Leu Asp Gly Gly Tyr Thr Phe Thr Glu Tyr Gln Lys Asn Pro
145                 150                 155                 160

Val Leu Ala Ala Asn Ser Thr Gln Phe Arg Asp Pro Lys Val Phe Trp
                165                 170                 175

Tyr Glu Pro Ser Gln Lys Trp Ile Met Thr Ala Ala Lys Ser Gln Asp
            180                 185                 190

Tyr Lys Ile Glu Ile Tyr Ser Ser Asp Asp Leu Lys Ser Trp Lys Leu
        195                 200                 205

Glu Ser Ala Phe Ala Asn Glu Gly Phe Leu Gly Tyr Gln Tyr Glu Cys
    210                 215                 220

Pro Gly Leu Ile Glu Val Pro Thr Glu Gln Asp Pro Ser Lys Ser Tyr
225                 230                 235                 240

Trp Val Met Phe Ile Ser Ile Asn Pro Gly Ala Pro Ala Gly Gly Ser
                245                 250                 255

Phe Asn Gln Tyr Phe Val Gly Ser Phe Asn Gly Thr His Phe Glu Ala
            260                 265                 270

Phe Asp Asn Gln Ser Arg Val Val Asp Phe Gly Lys Asp Tyr Tyr Ala
        275                 280                 285

Leu Gln Thr Phe Phe Asn Thr Asp Pro Thr Tyr Gly Ser Ala Leu Gly
    290                 295                 300

Ile Ala Trp Ala Ser Asn Trp Glu Tyr Ser Ala Phe Val Pro Thr Asn
305                 310                 315                 320

Pro Trp Arg Ser Ser Met Ser Leu Val Arg Lys Phe Ser Leu Asn Thr
                325                 330                 335

Glu Tyr Gln Ala Asn Pro Glu Thr Glu Leu Ile Asn Leu Lys Ala Glu
            340                 345                 350

-continued

```
Pro Ile Leu Asn Ile Ser Asn Ala Gly Pro Trp Ser Arg Phe Ala Thr
            355                 360                 365

Asn Thr Thr Leu Thr Lys Ala Asn Ser Tyr Asn Val Asp Leu Ser Asn
370                 375                 380

Ser Thr Gly Thr Leu Glu Phe Glu Leu Val Tyr Ala Val Asn Thr Thr
385                 390                 395                 400

Gln Thr Ile Ser Lys Ser Val Phe Ala Asp Leu Ser Leu Trp Phe Lys
                405                 410                 415

Gly Leu Glu Asp Pro Glu Glu Tyr Leu Arg Met Gly Phe Glu Val Ser
                420                 425                 430

Ala Ser Ser Phe Phe Leu Asp Arg Gly Asn Ser Lys Val Lys Phe Val
            435                 440                 445

Lys Glu Asn Pro Tyr Phe Thr Asn Arg Met Ser Val Asn Asn Gln Pro
    450                 455                 460

Phe Lys Ser Glu Asn Asp Leu Ser Tyr Tyr Lys Val Tyr Gly Leu Leu
465                 470                 475                 480

Asp Gln Asn Ile Leu Glu Leu Tyr Phe Asn Asp Gly Asp Val Val Ser
                485                 490                 495

Thr Asn Thr Tyr Phe Met Thr Thr Gly Asn Ala Leu Gly Ser Val Asn
                500                 505                 510

Met Thr Thr Gly Val Asp Asn Leu Phe Tyr Ile Asp Lys Phe Gln Val
            515                 520                 525

Arg Glu Val Lys
    530

<210> SEQ ID NO 4
<211> LENGTH: 532
<212> TYPE: PRT
<213> ORGANISM: Artificial Sequence
<220> FEATURE:
<223> OTHER INFORMATION: ScSUC2 N359K mutant

<400> SEQUENCE: 4

Met Leu Leu Gln Ala Phe Leu Phe Leu Leu Ala Gly Phe Ala Ala Lys
1               5                   10                  15

Ile Ser Ala Ser Met Thr Asn Glu Thr Ser Asp Arg Pro Leu Val His
            20                  25                  30

Phe Thr Pro Asn Lys Gly Trp Met Asn Asp Pro Asn Gly Leu Trp Tyr
        35                  40                  45

Asp Glu Lys Asp Ala Lys Trp His Leu Tyr Phe Gln Tyr Asn Pro Asn
    50                  55                  60

Asp Thr Val Trp Gly Thr Pro Leu Phe Trp Gly His Ala Thr Ser Asp
65                  70                  75                  80

Asp Leu Thr Asn Trp Glu Asp Gln Pro Ile Ala Ile Ala Pro Lys Arg
                85                  90                  95

Asn Asp Ser Gly Ala Phe Ser Gly Ser Met Val Val Asp Tyr Asn Asn
            100                 105                 110

Thr Ser Gly Phe Phe Asn Asp Thr Ile Asp Pro Arg Gln Arg Cys Val
        115                 120                 125

Ala Ile Trp Thr Tyr Asn Thr Pro Glu Ser Glu Glu Gln Tyr Ile Ser
    130                 135                 140

Tyr Ser Leu Asp Gly Gly Tyr Thr Phe Thr Glu Tyr Gln Lys Asn Pro
145                 150                 155                 160

Val Leu Ala Ala Asn Ser Thr Gln Phe Arg Asp Pro Lys Val Phe Trp
                165                 170                 175
```

Tyr Glu Pro Ser Gln Lys Trp Ile Met Thr Ala Ala Lys Ser Gln Asp
            180                 185                 190

Tyr Lys Ile Glu Ile Tyr Ser Ser Asp Asp Leu Lys Ser Trp Lys Leu
        195                 200                 205

Glu Ser Ala Phe Ala Asn Glu Gly Phe Leu Gly Tyr Gln Tyr Glu Cys
    210                 215                 220

Pro Gly Leu Ile Glu Val Pro Thr Glu Gln Asp Pro Ser Lys Ser Tyr
225                 230                 235                 240

Trp Val Met Phe Ile Ser Ile Asn Pro Gly Ala Pro Ala Gly Gly Ser
                245                 250                 255

Phe Asn Gln Tyr Phe Val Gly Ser Phe Asn Gly Thr His Phe Glu Ala
            260                 265                 270

Phe Asp Asn Gln Ser Arg Val Val Asp Phe Gly Lys Asp Tyr Tyr Ala
        275                 280                 285

Leu Gln Thr Phe Phe Asn Thr Asp Pro Thr Tyr Gly Ser Ala Leu Gly
    290                 295                 300

Ile Ala Trp Ala Ser Asn Trp Glu Tyr Ser Ala Phe Val Pro Thr Asn
305                 310                 315                 320

Pro Trp Arg Ser Ser Met Ser Leu Val Arg Lys Phe Ser Leu Asn Thr
                325                 330                 335

Glu Tyr Gln Ala Asn Pro Glu Thr Glu Leu Ile Asn Leu Lys Ala Glu
            340                 345                 350

Pro Ile Leu Asn Ile Ser Lys Ala Gly Pro Trp Ser Arg Phe Ala Thr
        355                 360                 365

Asn Thr Thr Leu Thr Lys Ala Asn Ser Tyr Asn Val Asp Leu Ser Asn
    370                 375                 380

Ser Thr Gly Thr Leu Glu Phe Glu Leu Val Tyr Ala Val Asn Thr Thr
385                 390                 395                 400

Gln Thr Ile Ser Lys Ser Val Phe Ala Asp Leu Ser Leu Trp Phe Lys
                405                 410                 415

Gly Leu Glu Asp Pro Glu Glu Tyr Leu Arg Met Gly Phe Glu Val Ser
            420                 425                 430

Ala Ser Ser Phe Phe Leu Asp Arg Gly Asn Ser Lys Val Lys Phe Val
        435                 440                 445

Lys Glu Asn Pro Tyr Phe Thr Asn Arg Met Ser Val Asn Asn Gln Pro
    450                 455                 460

Phe Lys Ser Glu Asn Asp Leu Ser Tyr Tyr Lys Val Tyr Gly Leu Leu
465                 470                 475                 480

Asp Gln Asn Ile Leu Glu Leu Tyr Phe Asn Asp Gly Asp Val Val Ser
                485                 490                 495

Thr Asn Thr Tyr Phe Met Thr Thr Gly Asn Ala Leu Gly Ser Val Asn
            500                 505                 510

Met Thr Thr Gly Val Asp Asn Leu Phe Tyr Ile Asp Lys Phe Gln Val
        515                 520                 525

Arg Glu Val Lys
    530

<210> SEQ ID NO 5
<211> LENGTH: 532
<212> TYPE: PRT
<213> ORGANISM: Artificial Sequence
<220> FEATURE:
<223> OTHER INFORMATION: ScSUC2 F366M mutant

<400> SEQUENCE: 5

```
Met Leu Leu Gln Ala Phe Leu Phe Leu Leu Ala Gly Phe Ala Ala Lys
1               5                   10                  15

Ile Ser Ala Ser Met Thr Asn Glu Thr Ser Asp Arg Pro Leu Val His
            20                  25                  30

Phe Thr Pro Asn Lys Gly Trp Met Asn Asp Pro Asn Gly Leu Trp Tyr
            35                  40                  45

Asp Glu Lys Asp Ala Lys Trp His Leu Tyr Phe Gln Tyr Asn Pro Asn
        50                  55                  60

Asp Thr Val Trp Gly Thr Pro Leu Phe Trp Gly His Ala Thr Ser Asp
65                  70                  75                  80

Asp Leu Thr Asn Trp Glu Asp Gln Pro Ile Ala Ile Ala Pro Lys Arg
                85                  90                  95

Asn Asp Ser Gly Ala Phe Ser Gly Ser Met Val Val Asp Tyr Asn Asn
            100                 105                 110

Thr Ser Gly Phe Phe Asn Asp Thr Ile Asp Pro Arg Gln Arg Cys Val
            115                 120                 125

Ala Ile Trp Thr Tyr Asn Thr Pro Glu Ser Glu Glu Gln Tyr Ile Ser
        130                 135                 140

Tyr Ser Leu Asp Gly Gly Tyr Thr Phe Thr Glu Tyr Gln Lys Asn Pro
145                 150                 155                 160

Val Leu Ala Ala Asn Ser Thr Gln Phe Arg Asp Pro Lys Val Phe Trp
                165                 170                 175

Tyr Glu Pro Ser Gln Lys Trp Ile Met Thr Ala Ala Lys Ser Gln Asp
            180                 185                 190

Tyr Lys Ile Glu Ile Tyr Ser Ser Asp Asp Leu Lys Ser Trp Lys Leu
        195                 200                 205

Glu Ser Ala Phe Ala Asn Glu Gly Phe Leu Gly Tyr Gln Tyr Glu Cys
        210                 215                 220

Pro Gly Leu Ile Glu Val Pro Thr Glu Gln Asp Pro Ser Lys Ser Tyr
225                 230                 235                 240

Trp Val Met Phe Ile Ser Ile Asn Pro Gly Ala Pro Ala Gly Gly Ser
                245                 250                 255

Phe Asn Gln Tyr Phe Val Gly Ser Phe Asn Gly Thr His Phe Glu Ala
            260                 265                 270

Phe Asp Asn Gln Ser Arg Val Val Asp Phe Gly Lys Asp Tyr Tyr Ala
            275                 280                 285

Leu Gln Thr Phe Phe Asn Thr Asp Pro Thr Tyr Gly Ser Ala Leu Gly
        290                 295                 300

Ile Ala Trp Ala Ser Asn Trp Glu Tyr Ser Ala Phe Val Pro Thr Asn
305                 310                 315                 320

Pro Trp Arg Ser Ser Met Ser Leu Val Arg Lys Phe Ser Leu Asn Thr
                325                 330                 335

Glu Tyr Gln Ala Asn Pro Glu Thr Glu Leu Ile Asn Leu Lys Ala Glu
            340                 345                 350

Pro Ile Leu Asn Ile Ser Asn Ala Gly Pro Trp Ser Arg Met Ala Thr
        355                 360                 365

Asn Thr Thr Leu Thr Lys Ala Asn Ser Tyr Asn Val Asp Leu Ser Asn
        370                 375                 380

Ser Thr Gly Thr Leu Glu Phe Glu Leu Val Tyr Ala Val Asn Thr Thr
385                 390                 395                 400

Gln Thr Ile Ser Lys Ser Val Phe Ala Asp Leu Ser Leu Trp Phe Lys
            405                 410                 415

Gly Leu Glu Asp Pro Glu Glu Tyr Leu Arg Met Gly Phe Glu Val Ser
```

```
                    420             425             430
Ala Ser Ser Phe Phe Leu Asp Arg Gly Asn Ser Lys Val Lys Phe Val
            435             440             445

Lys Glu Asn Pro Tyr Phe Thr Asn Arg Met Ser Val Asn Asn Gln Pro
    450             455             460

Phe Lys Ser Glu Asn Asp Leu Ser Tyr Tyr Lys Val Tyr Gly Leu Leu
465             470             475             480

Asp Gln Asn Ile Leu Glu Leu Tyr Phe Asn Asp Gly Asp Val Val Ser
                485             490             495

Thr Asn Thr Tyr Phe Met Thr Thr Gly Asn Ala Leu Gly Ser Val Asn
            500             505             510

Met Thr Thr Gly Val Asp Asn Leu Phe Tyr Ile Asp Lys Phe Gln Val
            515             520             525

Arg Glu Val Lys
        530

<210> SEQ ID NO 6
<211> LENGTH: 532
<212> TYPE: PRT
<213> ORGANISM: Artificial Sequence
<220> FEATURE:
<223> OTHER INFORMATION: ScSUC2 I17C-R28V mutant

<400> SEQUENCE: 6

Met Leu Leu Gln Ala Phe Leu Phe Leu Leu Ala Gly Phe Ala Ala Lys
1               5                   10                  15

Cys Ser Ala Ser Met Thr Asn Glu Thr Ser Asp Val Pro Leu Val His
            20                  25                  30

Phe Thr Pro Asn Lys Gly Trp Met Asn Asp Pro Asn Gly Leu Trp Tyr
        35                  40                  45

Asp Glu Lys Asp Ala Lys Trp His Leu Tyr Phe Gln Tyr Asn Pro Asn
    50                  55                  60

Asp Thr Val Trp Gly Thr Pro Leu Phe Trp Gly His Ala Thr Ser Asp
65                  70                  75                  80

Asp Leu Thr Asn Trp Glu Asp Gln Pro Ile Ala Ile Ala Pro Lys Arg
                85                  90                  95

Asn Asp Ser Gly Ala Phe Ser Gly Ser Met Val Val Asp Tyr Asn Asn
            100                 105                 110

Thr Ser Gly Phe Phe Asn Asp Thr Ile Asp Pro Arg Gln Arg Cys Val
        115                 120                 125

Ala Ile Trp Thr Tyr Asn Thr Pro Glu Ser Glu Glu Gln Tyr Ile Ser
    130                 135                 140

Tyr Ser Leu Asp Gly Gly Tyr Thr Phe Thr Glu Tyr Gln Lys Asn Pro
145                 150                 155                 160

Val Leu Ala Ala Asn Ser Thr Gln Phe Arg Asp Pro Lys Val Phe Trp
                165                 170                 175

Tyr Glu Pro Ser Gln Lys Trp Ile Met Thr Ala Ala Lys Ser Gln Asp
            180                 185                 190

Tyr Lys Ile Glu Ile Tyr Ser Ser Asp Asp Leu Lys Ser Trp Lys Leu
        195                 200                 205

Glu Ser Ala Phe Ala Asn Glu Gly Phe Leu Gly Tyr Gln Tyr Glu Cys
    210                 215                 220

Pro Gly Leu Ile Glu Val Pro Thr Glu Gln Asp Pro Ser Lys Ser Tyr
225                 230                 235                 240

Trp Val Met Phe Ile Ser Ile Asn Pro Gly Ala Pro Ala Gly Gly Ser
```

```
            245                 250                 255
Phe Asn Gln Tyr Phe Val Gly Ser Phe Asn Gly Thr His Phe Glu Ala
            260                 265                 270

Phe Asp Asn Gln Ser Arg Val Val Asp Phe Gly Lys Asp Tyr Tyr Ala
            275                 280                 285

Leu Gln Thr Phe Phe Asn Thr Asp Pro Thr Tyr Gly Ser Ala Leu Gly
            290                 295                 300

Ile Ala Trp Ala Ser Asn Trp Glu Tyr Ser Ala Phe Val Pro Thr Asn
305                 310                 315                 320

Pro Trp Arg Ser Ser Met Ser Leu Val Arg Lys Phe Ser Leu Asn Thr
            325                 330                 335

Glu Tyr Gln Ala Asn Pro Glu Thr Glu Leu Ile Asn Leu Lys Ala Glu
            340                 345                 350

Pro Ile Leu Asn Ile Ser Asn Ala Gly Pro Trp Ser Arg Phe Ala Thr
            355                 360                 365

Asn Thr Thr Leu Thr Lys Ala Asn Ser Tyr Asn Val Asp Leu Ser Asn
            370                 375                 380

Ser Thr Gly Thr Leu Glu Phe Glu Leu Val Tyr Ala Val Asn Thr Thr
385                 390                 395                 400

Gln Thr Ile Ser Lys Ser Val Phe Ala Asp Leu Ser Leu Trp Phe Lys
            405                 410                 415

Gly Leu Glu Asp Pro Glu Glu Tyr Leu Arg Met Gly Phe Glu Val Ser
            420                 425                 430

Ala Ser Ser Phe Phe Leu Asp Arg Gly Asn Ser Lys Val Lys Phe Val
            435                 440                 445

Lys Glu Asn Pro Tyr Phe Thr Asn Arg Met Ser Val Asn Asn Gln Pro
            450                 455                 460

Phe Lys Ser Glu Asn Asp Leu Ser Tyr Tyr Lys Val Tyr Gly Leu Leu
465                 470                 475                 480

Asp Gln Asn Ile Leu Glu Leu Tyr Phe Asn Asp Gly Asp Val Val Ser
            485                 490                 495

Thr Asn Thr Tyr Phe Met Thr Thr Gly Asn Ala Leu Gly Ser Val Asn
            500                 505                 510

Met Thr Thr Gly Val Asp Asn Leu Phe Tyr Ile Asp Lys Phe Gln Val
            515                 520                 525

Arg Glu Val Lys
            530

<210> SEQ ID NO 7
<211> LENGTH: 532
<212> TYPE: PRT
<213> ORGANISM: Artificial Sequence
<220> FEATURE:
<223> OTHER INFORMATION: ScSUC2 I17C-R28V-N359K mutant

<400> SEQUENCE: 7

Met Leu Leu Gln Ala Phe Leu Phe Leu Leu Ala Gly Phe Ala Ala Lys
1               5                   10                  15

Cys Ser Ala Ser Met Thr Asn Glu Thr Ser Asp Val Pro Leu Val His
            20                  25                  30

Phe Thr Pro Asn Lys Gly Trp Met Asn Asp Pro Asn Gly Leu Trp Tyr
            35                  40                  45

Asp Glu Lys Asp Ala Lys Trp His Leu Tyr Phe Gln Tyr Asn Pro Asn
            50                  55                  60

Asp Thr Val Trp Gly Thr Pro Leu Phe Trp Gly His Ala Thr Ser Asp
```

```
                65                  70                  75                  80
Asp Leu Thr Asn Trp Glu Asp Gln Pro Ile Ala Ile Ala Pro Lys Arg
                    85                  90                  95
Asn Asp Ser Gly Ala Phe Ser Gly Ser Met Val Val Asp Tyr Asn Asn
                    100                 105                 110
Thr Ser Gly Phe Phe Asn Asp Thr Ile Asp Pro Arg Gln Arg Cys Val
                    115                 120                 125
Ala Ile Trp Thr Tyr Asn Thr Pro Glu Ser Glu Gln Tyr Ile Ser
130                 135                 140
Tyr Ser Leu Asp Gly Gly Tyr Thr Phe Thr Glu Tyr Gln Lys Asn Pro
145                 150                 155                 160
Val Leu Ala Ala Asn Ser Thr Gln Phe Arg Asp Pro Lys Val Phe Trp
                    165                 170                 175
Tyr Glu Pro Ser Gln Lys Trp Ile Met Thr Ala Ala Lys Ser Gln Asp
                    180                 185                 190
Tyr Lys Ile Glu Ile Tyr Ser Ser Asp Asp Leu Lys Ser Trp Lys Leu
                    195                 200                 205
Glu Ser Ala Phe Ala Asn Glu Gly Phe Leu Gly Tyr Gln Tyr Glu Cys
                    210                 215                 220
Pro Gly Leu Ile Glu Val Pro Thr Glu Gln Asp Pro Ser Lys Ser Tyr
225                 230                 235                 240
Trp Val Met Phe Ile Ser Ile Asn Pro Gly Ala Pro Ala Gly Gly Ser
                    245                 250                 255
Phe Asn Gln Tyr Phe Val Gly Ser Phe Asn Gly Thr His Phe Glu Ala
                    260                 265                 270
Phe Asp Asn Gln Ser Arg Val Val Asp Phe Gly Lys Asp Tyr Tyr Ala
                    275                 280                 285
Leu Gln Thr Phe Phe Asn Thr Asp Pro Thr Tyr Gly Ser Ala Leu Gly
                    290                 295                 300
Ile Ala Trp Ala Ser Asn Trp Glu Tyr Ser Ala Phe Val Pro Thr Asn
305                 310                 315                 320
Pro Trp Arg Ser Ser Met Ser Leu Val Arg Lys Phe Ser Leu Asn Thr
                    325                 330                 335
Glu Tyr Gln Ala Asn Pro Glu Thr Glu Leu Ile Asn Leu Lys Ala Glu
                    340                 345                 350
Pro Ile Leu Asn Ile Ser Lys Ala Gly Pro Trp Ser Arg Phe Ala Thr
                    355                 360                 365
Asn Thr Thr Leu Thr Lys Ala Asn Ser Tyr Asn Val Asp Leu Ser Asn
                    370                 375                 380
Ser Thr Gly Thr Leu Glu Phe Glu Leu Val Tyr Ala Val Asn Thr Thr
385                 390                 395                 400
Gln Thr Ile Ser Lys Ser Val Phe Ala Asp Leu Ser Leu Trp Phe Lys
                    405                 410                 415
Gly Leu Glu Asp Pro Glu Glu Tyr Leu Arg Met Gly Phe Glu Val Ser
                    420                 425                 430
Ala Ser Ser Phe Phe Leu Asp Arg Gly Asn Ser Lys Val Lys Phe Val
                    435                 440                 445
Lys Glu Asn Pro Tyr Phe Thr Asn Arg Met Ser Val Asn Asn Gln Pro
                    450                 455                 460
Phe Lys Ser Glu Asn Asp Leu Ser Tyr Tyr Lys Val Tyr Gly Leu Leu
465                 470                 475                 480
Asp Gln Asn Ile Leu Glu Leu Tyr Phe Asn Asp Gly Asp Val Val Ser
                    485                 490                 495
```

```
Thr Asn Thr Tyr Phe Met Thr Thr Gly Asn Ala Leu Gly Ser Val Asn
            500                 505                 510

Met Thr Thr Gly Val Asp Asn Leu Phe Tyr Ile Asp Lys Phe Gln Val
        515                 520                 525

Arg Glu Val Lys
        530

<210> SEQ ID NO 8
<211> LENGTH: 532
<212> TYPE: PRT
<213> ORGANISM: Artificial Sequence
<220> FEATURE:
<223> OTHER INFORMATION: ScSUC2 I17C-R28V-F366M mutant

<400> SEQUENCE: 8

Met Leu Leu Gln Ala Phe Leu Phe Leu Leu Ala Gly Phe Ala Ala Lys
1               5                   10                  15

Cys Ser Ala Ser Met Thr Asn Glu Thr Ser Asp Val Pro Leu Val His
            20                  25                  30

Phe Thr Pro Asn Lys Gly Trp Met Asn Asp Pro Asn Gly Leu Trp Tyr
        35                  40                  45

Asp Glu Lys Asp Ala Lys Trp His Leu Tyr Phe Gln Tyr Asn Pro Asn
    50                  55                  60

Asp Thr Val Trp Gly Thr Pro Leu Phe Trp Gly His Ala Thr Ser Asp
65              70                  75                  80

Asp Leu Thr Asn Trp Glu Asp Gln Pro Ile Ala Ile Ala Pro Lys Arg
                85                  90                  95

Asn Asp Ser Gly Ala Phe Ser Gly Ser Met Val Val Asp Tyr Asn Asn
            100                 105                 110

Thr Ser Gly Phe Phe Asn Asp Thr Ile Asp Pro Arg Gln Arg Cys Val
        115                 120                 125

Ala Ile Trp Thr Tyr Asn Thr Pro Glu Ser Glu Glu Gln Tyr Ile Ser
    130                 135                 140

Tyr Ser Leu Asp Gly Gly Tyr Thr Phe Thr Glu Tyr Gln Lys Asn Pro
145                 150                 155                 160

Val Leu Ala Ala Asn Ser Thr Gln Phe Arg Asp Pro Lys Val Phe Trp
                165                 170                 175

Tyr Glu Pro Ser Gln Lys Trp Ile Met Thr Ala Ala Lys Ser Gln Asp
            180                 185                 190

Tyr Lys Ile Glu Ile Tyr Ser Ser Asp Asp Leu Lys Ser Trp Lys Leu
        195                 200                 205

Glu Ser Ala Phe Ala Asn Glu Gly Phe Leu Gly Tyr Gln Tyr Glu Cys
    210                 215                 220

Pro Gly Leu Ile Glu Val Pro Thr Glu Gln Asp Pro Ser Lys Ser Tyr
225                 230                 235                 240

Trp Val Met Phe Ile Ser Ile Asn Pro Gly Ala Pro Ala Gly Gly Ser
                245                 250                 255

Phe Asn Gln Tyr Phe Val Gly Ser Phe Asn Gly Thr His Phe Glu Ala
            260                 265                 270

Phe Asp Asn Gln Ser Arg Val Val Asp Phe Gly Lys Asp Tyr Tyr Ala
        275                 280                 285

Leu Gln Thr Phe Phe Asn Thr Asp Pro Thr Tyr Gly Ser Ala Leu Gly
    290                 295                 300

Ile Ala Trp Ala Ser Asn Trp Glu Tyr Ser Ala Phe Val Pro Thr Asn
305                 310                 315                 320
```

```
Pro Trp Arg Ser Ser Met Ser Leu Val Arg Lys Phe Ser Leu Asn Thr
            325                 330                 335

Glu Tyr Gln Ala Asn Pro Glu Thr Glu Leu Ile Asn Leu Lys Ala Glu
            340                 345                 350

Pro Ile Leu Asn Ile Ser Asn Ala Gly Pro Trp Ser Arg Met Ala Thr
            355                 360                 365

Asn Thr Thr Leu Thr Lys Ala Asn Ser Tyr Asn Val Asp Leu Ser Asn
            370                 375                 380

Ser Thr Gly Thr Leu Glu Phe Glu Leu Val Tyr Ala Val Asn Thr Thr
385                 390                 395                 400

Gln Thr Ile Ser Lys Ser Val Phe Ala Asp Leu Ser Leu Trp Phe Lys
            405                 410                 415

Gly Leu Glu Asp Pro Glu Glu Tyr Leu Arg Met Gly Phe Glu Val Ser
            420                 425                 430

Ala Ser Ser Phe Phe Leu Asp Arg Gly Asn Ser Lys Val Lys Phe Val
            435                 440                 445

Lys Glu Asn Pro Tyr Phe Thr Asn Arg Met Ser Val Asn Asn Gln Pro
            450                 455                 460

Phe Lys Ser Glu Asn Asp Leu Ser Tyr Tyr Lys Val Tyr Gly Leu Leu
465                 470                 475                 480

Asp Gln Asn Ile Leu Glu Leu Tyr Phe Asn Asp Gly Asp Val Val Ser
            485                 490                 495

Thr Asn Thr Tyr Phe Met Thr Gly Asn Ala Leu Gly Ser Val Asn
            500                 505                 510

Met Thr Thr Gly Val Asp Asn Leu Phe Tyr Ile Asp Lys Phe Gln Val
            515                 520                 525

Arg Glu Val Lys
    530

<210> SEQ ID NO 9
<211> LENGTH: 532
<212> TYPE: PRT
<213> ORGANISM: Artificial Sequence
<220> FEATURE:
<223> OTHER INFORMATION: ScSUC2 I17C-R28V-N359K-F366M mutant

<400> SEQUENCE: 9

Met Leu Leu Gln Ala Phe Leu Phe Leu Leu Ala Gly Phe Ala Ala Lys
1               5                   10                  15

Cys Ser Ala Ser Met Thr Asn Glu Thr Ser Asp Val Pro Leu Val His
            20                  25                  30

Phe Thr Pro Asn Lys Gly Trp Met Asn Asp Pro Asn Gly Leu Trp Tyr
            35                  40                  45

Asp Glu Lys Asp Ala Lys Trp His Leu Tyr Phe Gln Tyr Asn Pro Asn
        50                  55                  60

Asp Thr Val Trp Gly Thr Pro Leu Phe Trp Gly His Ala Thr Ser Asp
65                  70                  75                  80

Asp Leu Thr Asn Trp Glu Asp Gln Pro Ile Ala Ile Ala Pro Lys Arg
            85                  90                  95

Asn Asp Ser Gly Ala Phe Ser Gly Ser Met Val Val Asp Tyr Asn Asn
            100                 105                 110

Thr Ser Gly Phe Phe Asn Asp Thr Ile Asp Pro Arg Gln Arg Cys Val
            115                 120                 125

Ala Ile Trp Thr Tyr Asn Thr Pro Glu Ser Glu Glu Gln Tyr Ile Ser
        130                 135                 140
```

```
Tyr Ser Leu Asp Gly Gly Tyr Thr Phe Thr Glu Tyr Gln Lys Asn Pro
145                 150                 155                 160

Val Leu Ala Ala Asn Ser Thr Gln Phe Arg Asp Pro Lys Val Phe Trp
            165                 170                 175

Tyr Glu Pro Ser Gln Lys Trp Ile Met Thr Ala Ala Lys Ser Gln Asp
        180                 185                 190

Tyr Lys Ile Glu Ile Tyr Ser Ser Asp Asp Leu Lys Ser Trp Lys Leu
    195                 200                 205

Glu Ser Ala Phe Ala Asn Glu Gly Phe Leu Gly Tyr Gln Tyr Glu Cys
210                 215                 220

Pro Gly Leu Ile Glu Val Pro Thr Glu Gln Asp Pro Ser Lys Ser Tyr
225                 230                 235                 240

Trp Val Met Phe Ile Ser Ile Asn Pro Gly Ala Pro Ala Gly Gly Ser
                245                 250                 255

Phe Asn Gln Tyr Phe Val Gly Ser Phe Asn Gly Thr His Phe Glu Ala
            260                 265                 270

Phe Asp Asn Gln Ser Arg Val Val Asp Phe Gly Lys Asp Tyr Tyr Ala
        275                 280                 285

Leu Gln Thr Phe Phe Asn Thr Asp Pro Thr Tyr Gly Ser Ala Leu Gly
    290                 295                 300

Ile Ala Trp Ala Ser Asn Trp Glu Tyr Ser Ala Phe Val Pro Thr Asn
305                 310                 315                 320

Pro Trp Arg Ser Ser Met Ser Leu Val Arg Lys Phe Ser Leu Asn Thr
                325                 330                 335

Glu Tyr Gln Ala Asn Pro Glu Thr Glu Leu Ile Asn Leu Lys Ala Glu
            340                 345                 350

Pro Ile Leu Asn Ile Ser Lys Ala Gly Pro Trp Ser Arg Met Ala Thr
        355                 360                 365

Asn Thr Thr Leu Thr Lys Ala Asn Ser Tyr Asn Val Asp Leu Ser Asn
    370                 375                 380

Ser Thr Gly Thr Leu Glu Phe Glu Leu Val Tyr Ala Val Asn Thr Thr
385                 390                 395                 400

Gln Thr Ile Ser Lys Ser Val Phe Ala Asp Leu Ser Leu Trp Phe Lys
                405                 410                 415

Gly Leu Glu Asp Pro Glu Glu Tyr Leu Arg Met Gly Phe Glu Val Ser
            420                 425                 430

Ala Ser Ser Phe Phe Leu Asp Arg Gly Asn Ser Lys Val Lys Phe Val
        435                 440                 445

Lys Glu Asn Pro Tyr Phe Thr Asn Arg Met Ser Val Asn Asn Gln Pro
    450                 455                 460

Phe Lys Ser Glu Asn Asp Leu Ser Tyr Tyr Lys Val Tyr Gly Leu Leu
465                 470                 475                 480

Asp Gln Asn Ile Leu Glu Leu Tyr Phe Asn Asp Gly Asp Val Val Ser
                485                 490                 495

Thr Asn Thr Tyr Phe Met Thr Thr Gly Asn Ala Leu Gly Ser Val Asn
            500                 505                 510

Met Thr Thr Gly Val Asp Asn Leu Phe Tyr Ile Asp Lys Phe Gln Val
        515                 520                 525

Arg Glu Val Lys
    530
```

<210> SEQ ID NO 10
<211> LENGTH: 6797

<212> TYPE: DNA
<213> ORGANISM: Artificial Sequence
<220> FEATURE:
<223> OTHER INFORMATION: Nucleic acid sequence of construct pSZ6917

<400> SEQUENCE: 10

```
agcggaagag cgcccaatgt ttaaacagcc cgcaccctcg ttgatctggg agccctgcgc      60
agccccttaa atcatctcag tcaggtttct gtgttcaact gagcctaaag ggctttcgtc     120
atgcgcacga gcacacgtat atcggccacg cagtttctca aaagcggtag aacagttcgc     180
gagccctcgt aggtcgaaaa cttgcgccag tactattaaa ttaaattaat tgatcgaacg     240
agacgcgaaa cttttgcaga atgccaccga gtttgcccag agaatgggag tggcgccatt     300
caccatccgc ctgtgcccgg cttgattcgc cgagacgatg gacggcgaga ccagggagcg     360
gcttgcgagc cccgagccgg tagcaggaac aatgatcgac aatcttcctg tccaattact     420
ggcaaccatt agaaagagcc ggagcgcgtt gaaagtctgc aatcgagtaa ttttcgata     480
cgtcgggcct gctgaaccct aaggctccgg actttgttta aggcgatcca agatgcacgc     540
ggccccaggc acgtatctca agcacaaacc ccagccttag tttcgagact tgggagata     600
gcgaccgata tctagtttgg cattttgtat attaattacc tcaagcaatg gagcgctctg     660
atgcggtgca gcgtcggctg cagcacctgg cagtggcgct agggtcgccc tatcgctcgg     720
aacctggtca gctggctccc gcctcctgct cagcctcttc cggtacccct tcttgcgcta     780
tgacacttcc agcaaaaggt agggcgggct gcgagacggc ttcccggcgc tgcatgcaac     840
accgatgatg cttcgacccc ccgaagctcc ttcggggctg catgggcgct ccgatgccgc     900
tccagggcga gcgctgttta aatagccagg ccccgattg caaagacatt atagcgagct     960
accaaagcca tattcaaaca cctagatcac taccacttct acacaggcca ctcgagcttg    1020
tgatcgcact ccgctaaggg ggcgcctctt cctcttcgtt tcagtcacaa cccgcaaact    1080
ctagaatatc aatgctgctg caggccttcc tgttcctgct ggccggcttc gccgccaagt    1140
gcagcgcctc catgacgaac gagacgtccg acgtgcccct ggtgcacttc accccaaca    1200
agggctggat gaacgacccc aacgccgtgt ggtacgacga aaggacgcc aagtggcacc    1260
tgtacttcca gtacaacccg aacgacaccg tctggggac gcccttgttc tggggccacg    1320
ccacgtccga cgacctgacc aactgggagg accagcccat cgccatcgcc cgaagcgca    1380
acgactccgg cgccttctcc ggctccatgg tggtggacta caacaacacc tccggcttct    1440
tcaacgacac catcgacccg cgccagcgct gcgtggccat ctggacctac aacaccccgg    1500
agtccgagga gcagtacatc tcctacagcc tggacggcgg ctacaccttc accgagtacc    1560
agaagaaccc cgtgctggcc gccaactcca cccagttccg cgacccgaag gtcttctggt    1620
acgagccctc ccagaagtgg atcatgaccg cggccaagtc ccaggactac aagatcgaga    1680
tctactcctc cgacgacctg aagtcctgga agctggagtc cgcgttcgcc aacgagggct    1740
tcctcggcta ccagtacgag tgccccgcc tgatcgaggt cccaccgag caggacccca    1800
gcaagtccta ctgggtgatg ttcatctcca tcaacccgg cgccccggcc ggcggctcct    1860
tcaaccagta cttcgtcggc agcttcaacg gcacccactt cgaggccttc gacaaccagt    1920
cccgcgtggt ggacttcggc aaggactact acgccctgca gaccttcttc aacaccgacc    1980
cgacctacgg gagcgccctg ggcatcgcgt gggcctccaa ctgggagtac tccgccttcg    2040
tgccaccaa ccctggcgc tcctccatgt ccctcgtgcg caagttctcc ctcaacaccg    2100
agtaccaggc caacccggag acggagctga tcaacctgaa ggccgagccg atcctgaaca    2160
```

-continued

| | | | | | |
|---|---|---|---|---|---|
| tcagcaaggc | cggccctgg | agccggatgg | ccaccaacac | cacgttgacg | aaggccaaca | 2220 |
| gctacaacgt | cgacctgtcc | aacagcaccg | gcaccctgga | gttcgagctg | gtgtacgccg | 2280 |
| tcaacaccac | ccagacgatc | tccaagtccg | tgttcgcgga | cctctccctc | tggttcaagg | 2340 |
| gcctggagga | ccccgaggag | tacctccgca | tgggcttcga | ggtgtccgcg | tcctccttct | 2400 |
| tcctggaccg | cgggaacagc | aaggtgaagt | tcgtgaagga | gaaccccta c| ttcaccaacc | 2460 |
| gcatgagcgt | gaacaaccag | cccttcaaga | gcgagaacga | cctgtcctac | tacaaggtgt | 2520 |
| acggcttgct | ggaccagaac | atcctggagc | tgtacttcaa | cgacggcgac | gtcgtgtcca | 2580 |
| ccaacaccta | cttcatgacc | accgggaacg | ccctgggctc | cgtgaacatg | acgacggggg | 2640 |
| tggacaacct | gttctacatc | gacaagttcc | aggtgcgcga | ggtcaagtga | caattgacgc | 2700 |
| ccgcgcggcg | cacctgacct | gttctctcga | gggcgcctgt | tctgccttgc | gaaacaagcc | 2760 |
| cctggagcat | gcgtgcatga | tcgtctctgg | cgccccgccg | cgcggtttgt | cgccctcgcg | 2820 |
| ggcgccgcgg | ccgcggggc | gcattgaaat | tgttgcaaac | cccacctgac | agattgaggg | 2880 |
| cccaggcagg | aaggcgttga | gatggaggta | caggagtcaa | gtaactgaaa | gtttttatga | 2940 |
| taactaacaa | caaagggtcg | tttctggcca | gcgaatgaca | agaacaagat | tccacatttc | 3000 |
| cgtgtagagg | cttgccatcg | aatgtgagcg | ggcgggccgc | ggacccgaca | aaacccttac | 3060 |
| gacgtggtaa | gaaaaacgtg | gcgggcactg | tccctgtagc | ctgaagacca | gcaggagacg | 3120 |
| atcggaagca | tcacagcaca | ggatcccgcg | tctcgaacag | agcgcgcaga | ggaacgctga | 3180 |
| aggtctcgcc | tctgtcgcac | ctcagcgcgg | catacaccac | aataaccacc | tgacgaatgc | 3240 |
| gcttggttct | tcgtccatta | gcgaagcgtc | cggttcacac | acgtgccacg | ttggcgaggt | 3300 |
| ggcaggtgac | aatgatcggt | ggagctgatg | gtcgaaacgt | tcacagccta | ggatcgagtg | 3360 |
| tacagtcaat | gaatggtgag | ctcagcgtct | gcgtgttggg | agctggagtc | gtgggcttga | 3420 |
| cgacggcgct | gcagctgttg | caggatgtgc | ctggcgtgcg | cgttcacgtc | gtggctgaga | 3480 |
| aatatggcga | cgaaacgttg | acggctgggg | ccggcgggct | gtggatgcca | tacgcattgg | 3540 |
| gtacgcggcc | attggatggg | attgataggc | ttatggaggg | ataatagagt | ttttgccgga | 3600 |
| tccaacgcat | gtggatgcgg | tatcccggtg | ggctgaaagt | gtggaaggat | agtgcattgg | 3660 |
| ctattcacat | gcactgccca | cccctttggg | caggaaatgt | gccggcatcg | ttggtgcacc | 3720 |
| gatgggaaa | atcgacgttc | gaccactaca | tgaagattta | tacgtctgaa | gatgcagcga | 3780 |
| ctgcgggtgc | gaaacggatg | acggtttggt | cgtgtatgtc | acagcatgtg | ctggatcttg | 3840 |
| cgggctaact | ccccctgcca | cggcccattg | caggtgtcat | gttgactgga | gggtacgacc | 3900 |
| tttcgtccgt | caaattccca | gaggaggacc | cgctctgggc | cgacattgtg | cccactgaag | 3960 |
| agcgtttaaa | ccgcctctcc | ccgcgcgttg | gccgattcat | taatgcagct | ggcacgacag | 4020 |
| gtttcccgac | tggaaagcgg | gcagtgagcg | caacgcaatt | aatgtgagtt | agctcactca | 4080 |
| ttaggcaccc | caggctttac | actttatgct | tccggctcgt | atgttgtgtg | gaattgtgag | 4140 |
| cggataacaa | tttcacacag | gaaacagcta | tgaccatgat | tacgccaagc | tcgaaattaa | 4200 |
| ccctcactaa | agggaacaaa | agctggccaa | ttcgccctat | agtgagtcgt | attacaattc | 4260 |
| actggccgtc | gttttacaac | gtcgtgactg | ggaaaaccct | ggcgttaccc | aacttaatcg | 4320 |
| ccttgcagca | catccccctt | tcgccagctg | gcgtaatagc | gaagaggccc | gcaccgatcg | 4380 |
| cccttcccaa | cagttgcgca | gcctgaatgg | cgaatgggac | gcgccctgta | gcggcgcatt | 4440 |
| aagcgcggcg | ggtgtggtgg | ttacgcgcag | cgtgaccgct | acacttgcca | gcgccctagc | 4500 |
| gcccgctcct | ttcgctttct | tcccttcctt | tctcgccacg | ttcgccggct | ttccccgtca | 4560 |

```
agctctaaat cgggggctcc ctttagggtt ccgatttagt gctttacggc acctcgaccc    4620
caaaaaactt gattagggtg atggttcacg tagtgggcca tcgccctgat agacggtttt    4680
tcgccctttg acgttggagt ccacgttctt taatagtgga ctcttgttcc aaactggaac    4740
aacactcaac cctatctcgg tctattcttt tgatttataa gggattttgc cgatttcggc    4800
ctattggtta aaaatgagc tgatttaaca aaaatttaac gcgaatttta acaaaatatt    4860
aacgcttaca atttaggtgg cacttttcgg ggaaatgtgc gcggaacccc tatttgttta    4920
tttttctaaa tacattcaaa tatgtatccg ctcatgagac aataaccctg ataaatgctt    4980
caataatatt gaaaaaggaa gagtatgagt attcaacatt tccgtgtcgc ccttattccc    5040
ttttttgcgg catttttgcct tcctgttttt gctcacccag aaacgctggt gaaagtaaaa    5100
gatgctgaag atcagttggg tgcacgagtg ggttacatcg aactggatct caacagcggt    5160
aagatccttg agagttttcg ccccgaagaa cgttttccaa tgatgagcac ttttaaagtt    5220
ctgctatgtg gcgcggtatt atcccgtatt gacgccgggc aagagcaact cggtcgccgc    5280
atacactatt ctcagaatga cttggttgag tactcaccag tcacagaaaa gcatcttacg    5340
gatggcatga cagtaagaga attatgcagt gctgccataa ccatgagtga taacactgcg    5400
gccaacttac ttctgacaac gatcggagga ccgaaggagc taaccgcttt tttgcacaac    5460
atggggatc atgtaactcg ccttgatcgt tgggaaccgg agctgaatga agccatacca    5520
aacgacgagc gtgacaccac gatgcctgta gcaatggcaa caacgttgcg caaactatta    5580
actggcgaac tacttactct agcttcccgg caacaattaa tagactggat ggaggcggat    5640
aaagttgcag gaccacttct gcgctcggcc cttccggctg gctggtttat tgctgataaa    5700
tctggagccg gtgagcgtgg gtctcgcggt atcattgcag cactgggcc agatggtaag    5760
ccctcccgta tcgtagttat ctacacgacg gggagtcagg caactatgga tgaacgaaat    5820
agacagatcg ctgagatagg tgcctcactg attaagcatt ggtaactgtc agaccaagtt    5880
tactcatata ctttagat tgatttaaaa cttcattttt aatttaaaag gatctaggtg    5940
aagatccttt tgataatct catgaccaaa atcccttaac gtgagttttc gttccactga    6000
gcgtcagacc ccgtagaaaa gatcaaagga tcttcttgag atcctttttt tctgcgcgta    6060
atctgctgct tgcaaacaaa aaaaccaccg ctaccagcgg tggtttgttt gccggatcaa    6120
gagctaccaa ctcttttcc gaaggtaact ggcttcagca gagcgcagat accaaatact    6180
gtccttctag tgtagccgta gttaggccac cacttcaaga actctgtagc accgcctaca    6240
tacctcgctc tgctaatcct gttaccagtg gctgctgcca gtggcgataa gtcgtgtctt    6300
accgggttgg actcaagacg atagttaccg gataaggcgc agcggtcggg ctgaacgggg    6360
ggttcgtgca cacagcccag cttggagcga acgacctaca ccgaactgag atacctacag    6420
cgtgagctat gagaaagcgc cacgcttccc gaagggagaa aggcggacag gtatccggta    6480
agcggcaggg tcgaacagg agagcgcacg agggagcttc cagggggaaa cgcctggtat    6540
ctttatagtc ctgtcgggtt tcgccacctc tgacttgagc gtcgattttt gtgatgctcg    6600
tcaggggggc ggagcctatg gaaaaacgcc agcaacgcgg cctttttacg gttcctggcc    6660
ttttgctggc cttttgctca catgttcttt cctgcgttat cccctgattc tgtggataac    6720
cgtattaccg cctttgagtg agctgatacc gctcgccgca gccgaacgac cgagcgcagc    6780
gagtcagtga gcgagga                                                   6797
```

<210> SEQ ID NO 11

<211> LENGTH: 1599
<212> TYPE: DNA
<213> ORGANISM: Artificial Sequence
<220> FEATURE:
<223> OTHER INFORMATION: wild-type S. cerevisiae SUC2 with codon bias
      for improved expression in P. moriformis

<400> SEQUENCE: 11

| | | | | | |
|---|---|---|---|---|---|
| atgctgctgc | aggccttcct | gttcctgctg | gccggcttcg | ccgccaagat | cagcgcctcc | 60 |
| atgacgaacg | agacgtccga | ccgcccctg | gtgcacttca | cccccaacaa | gggctggatg | 120 |
| aacgacccca | acggcctgtg | gtacgacgag | aaggacgcca | gtggcacct | gtacttccag | 180 |
| tacaacccga | acgacaccgt | ctggggacg | cccttgttct | ggggccacgc | cacgtccgac | 240 |
| gacctgacca | actgggagga | ccagcccatc | gccatcgccc | gaagcgcaa | cgactccggc | 300 |
| gccttctccg | gctccatggt | ggtggactac | aacaacacct | ccggcttctt | caacgacacc | 360 |
| atcgacccgc | gccagcgctg | cgtggccatc | tggacctaca | caccccgga | gtccgaggag | 420 |
| cagtacatct | cctacagcct | ggacggcggc | tacaccttca | ccgagtacca | gaagaacccc | 480 |
| gtgctggccg | ccaactccac | ccagttccgc | gacccgaagg | tcttctggta | cgagccctcc | 540 |
| cagaagtgga | tcatgaccgc | ggccaagtcc | caggactaca | gatcgagat | ctactcctcc | 600 |
| gacgacctga | agtcctggaa | gctggagtcc | gcgttcgcca | acgagggctt | cctcggctac | 660 |
| cagtacgagt | gccccggcct | gatcgaggtc | cccaccgagc | aggaccccag | caagtcctac | 720 |
| tgggtgatgt | tcatctccat | caaccccggc | gccccggccg | gcggctcctt | caaccagtac | 780 |
| ttcgtcggca | gcttcaacgg | cacccacttc | gaggccttcg | acaaccagtc | cgcgtggtg | 840 |
| gacttcggca | aggactacta | cgccctgcag | accttcttca | caccgaccc | gacctacggg | 900 |
| agcgccctgg | gcatcgcgtg | ggcctccaac | tgggagtact | ccgccttcgt | gcccaccaac | 960 |
| ccctggcgct | cctccatgtc | cctcgtgcgc | aagttctccc | tcaacaccga | gtaccaggcc | 1020 |
| aacccggaga | cggagctgat | caacctgaag | gccgagccga | tcctgaacat | cagcaacgcc | 1080 |
| ggccccctgga | gccggttcgc | caccaacacc | acgttgacga | aggccaacag | ctacaacgtc | 1140 |
| gacctgtcca | acagcaccgg | caccctggag | ttcgagctgg | tgtacgccgt | caacaccacc | 1200 |
| cagacgatct | ccaagtccgt | gttcgcggac | ctctcccctct | ggttcaaggg | cctggaggac | 1260 |
| cccgaggagt | acctccgcat | gggcttcgag | gtgtccgcgt | cctccttctt | cctggaccgc | 1320 |
| gggaacagca | aggtgaagtt | cgtgaaggag | aaccccctact | tcaccaaccg | catgagcgtg | 1380 |
| aacaaccagc | ccttcaagag | cgagaacgac | ctgtcctact | acaaggtgta | cggcttgctg | 1440 |
| gaccagaaca | tcctggagct | gtacttcaac | gacggcgacg | tcgtgtccac | caacacctac | 1500 |
| ttcatgacca | ccgggaacgc | cctgggctcc | gtgaacatga | cgacggggt | ggacaacctg | 1560 |
| ttctacatcg | acaagttcca | ggtgcgcgag | gtcaagtga | | | 1599 |

<210> SEQ ID NO 12
<211> LENGTH: 1599
<212> TYPE: DNA
<213> ORGANISM: Artificial Sequence
<220> FEATURE:
<223> OTHER INFORMATION: S. cerevisiae SUC2 I17C enzyme variant

<400> SEQUENCE: 12

| | | | | | |
|---|---|---|---|---|---|
| atgctgctgc | aggccttcct | gttcctgctg | gccggcttcg | ccgccaagtg | cagcgcctcc | 60 |
| atgacgaacg | agacgtccga | ccgcccctg | gtgcacttca | cccccaacaa | gggctggatg | 120 |
| aacgacccca | acggcctgtg | gtacgacgag | aaggacgcca | gtggcacct | gtacttccag | 180 |

| | |
|---|---|
| tacaacccga acgacaccgt ctgggggacg cccttgttct ggggccacgc cacgtccgac | 240 |
| gacctgacca actgggagga ccagcccatc gccatcgccc cgaagcgcaa cgactccggc | 300 |
| gccttctccg gctccatggt ggtggactac aacaacacct ccggcttctt caacgacacc | 360 |
| atcgacccgc gccagcgctg cgtggccatc tggacctaca caccccgga gtccgaggag | 420 |
| cagtacatct cctacagcct ggacggcggc tacaccttca ccgagtacca aagaaccccc | 480 |
| gtgctggccg ccaactccac ccagttccgc gacccgaagg tcttctggta cgagccctcc | 540 |
| cagaagtgga tcatgaccgc ggccaagtcc caggactaca agatcgagat ctactcctcc | 600 |
| gacgacctga agtcctggaa gctggagtcc gcgttcgcca acgagggctt cctcggctac | 660 |
| cagtacgagt gccccggcct gatcgaggtc cccaccgagc aggaccccag caagtcctac | 720 |
| tgggtgatgt tcatctccat caaccccggc gccccggccg gcggctcctt caaccagtac | 780 |
| ttcgtcggca gcttcaacgg cacccacttc gaggccttcg acaaccagtc ccgcgtggtg | 840 |
| gacttcggca aggactacta cgccctgcag accttcttca acaccgaccc gacctacggg | 900 |
| agcgccctgg gcatcgcgtg ggcctccaac tgggagtact ccgccttcgt gcccaccaac | 960 |
| ccctggcgct cctccatgtc cctcgtgcgc aagttctccc tcaacaccga gtaccaggcc | 1020 |
| aacccggaga cggagctgat caacctgaag gccgagccga tcctgaacat cagcaacgcc | 1080 |
| ggccccctgga gccggttcgc caccaacacc acgttgacga aggccaacag ctacaacgtc | 1140 |
| gacctgtcca acagcaccgg cacgctggag ttcgagctgg tgtacgccgt caacaccacc | 1200 |
| cagacgatct ccaagtccgt gttcgcggac ctctcccctct ggttcaaggg cctggaggac | 1260 |
| cccgaggagt acctccgcat gggcttcgag gtgtccgcgt cctccttctt cctggaccgc | 1320 |
| gggaacagca aggtgaagtt cgtgaaggag aaccccctact tcaccaaccg catgagcgtg | 1380 |
| aacaaccagc ccttcaagag cgagaacgac ctgtcctact acaaggtgta cggcttgctg | 1440 |
| gaccagaaca tcctggagct gtacttcaac gacggcgacg tcgtgtccac caacacctac | 1500 |
| ttcatgacca ccgggaacgc cctgggctcc gtgaacatga cgacgggggt ggacaacctg | 1560 |
| ttctacatcg acaagttcca ggtgcgcgag gtcaagtga | 1599 |

<210> SEQ ID NO 13
<211> LENGTH: 1599
<212> TYPE: DNA
<213> ORGANISM: Artificial Sequence
<220> FEATURE:
<223> OTHER INFORMATION: S. cerevisiae SUC2 R28V enzyme variant

<400> SEQUENCE: 13

| | |
|---|---|
| atgctgctgc aggccttcct gttcctgctg gccggcttcg ccgccaagat cagcgcctcc | 60 |
| atgacgaacg agacgtccga cgtgcccctg gtgcacttca cccccaacaa gggctggatg | 120 |
| aacgacccca cggcctgtg gtacgacgag aaggacgcca agtggcacct gtacttccag | 180 |
| tacaacccga acgacaccgt ctgggggacg cccttgttct ggggccacgc cacgtccgac | 240 |
| gacctgacca actgggagga ccagcccatc gccatcgccc cgaagcgcaa cgactccggc | 300 |
| gccttctccg gctccatggt ggtggactac aacaacacct ccggcttctt caacgacacc | 360 |
| atcgacccgc gccagcgctg cgtggccatc tggacctaca caccccgga gtccgaggag | 420 |
| cagtacatct cctacagcct ggacggcggc tacaccttca ccgagtacca aagaaccccc | 480 |
| gtgctggccg ccaactccac ccagttccgc gacccgaagg tcttctggta cgagccctcc | 540 |
| cagaagtgga tcatgaccgc ggccaagtcc caggactaca agatcgagat ctactcctcc | 600 |
| gacgacctga agtcctggaa gctggagtcc gcgttcgcca acgagggctt cctcggctac | 660 |

```
cagtacgagt gccccggcct gatcgaggtc cccaccgagc aggacccag  caagtcctac    720 tgggtgatgt tcatctccat caaccccggc gccccggccg gcggctcctt caaccagtac    780
ttcgtcggca gcttcaacgg cacccacttc gaggccttcg acaaccagtc ccgcgtggtg    840
gacttcggca aggactacta cgccctgcag accttcttca acaccgaccc gacctacggg    900
agcgccctgg gcatcgcgtg ggcctccaac tgggagtact ccgccttcgt gcccaccaac    960
ccctggcgct cctccatgtc cctcgtgcgc aagttctccc tcaacaccga gtaccaggcc   1020
aacccggaga cggagctgat caacctgaag gccgagccga tcctgaacat cagcaacgcc   1080 ggccctgga  gccggttcgc caccaacacc acgttgacga aggccaacag ctacaacgtc    1140
gacctgtcca acagcaccgg cacctggag  ttcgagctgg tgtacgccgt caacaccacc   1200
cagacgatct ccaagtccgt gttcgcggac ctctccctct ggttcaaggg cctggaggac   1260
cccgaggagt acctccgcat gggcttcgag gtgtccgcgt cctccttctt cctggaccgc   1320
gggaacagca aggtgaagtt cgtgaaggag aaccccctact tcaccaaccg catgagcgtg   1380
aacaaccagc ccttcaagag cgagaacgac ctgtcctact acaaggtgta cggcttgctg   1440
gaccagaaca tcctggagct gtacttcaac gacggcgacg tcgtgtccac caacacctac   1500
ttcatgacca ccgggaacgc cctgggctcc gtgaacatga cgacggggt  ggacaacctg   1560 ttctacatcg acaagttcca ggtgcgcgag gtcaagtga                          1599

<210> SEQ ID NO 14
<211> LENGTH: 1599
<212> TYPE: DNA
<213> ORGANISM: Artificial Sequence
<220> FEATURE:
<223> OTHER INFORMATION: S. cerevisiae SUC2 I17C-R28V enzyme variant

<400> SEQUENCE: 14
atgctgctgc aggccttcct gttcctgctg gccggcttcg ccgccaagtg cagcgcctcc     60
atgacgaacg agacgtccga cgtgcccctg gtgcacttca cccccaacaa gggctggatg    120
aacgacccca cggcctgtg  gtacgacgag aaggacgcca gtggcacct  gtacttccag    180 tacaacccga cgacaccgt  ctgggggacg cccttgttct ggggcacgc  cacgtccgac    240 gacctgacca actgggagga ccagcccatc gccatcgccc cgaagcgcaa cgactccggc    300
gccttctccg gctccatggt ggtggactac aacaacacct ccggcttctt caacgacacc    360
atcgacccgc gccagcgctg cgtggccatc tggacctaca acaccccgga gtccgaggag    420
cagtacatct cctacagcct ggacggcggc tacaccttca ccgagtacca gaagaacccc    480
gtgctggccg ccaactccac ccagttccgc gacccgaagg tcttctggta cgagccctcc    540
cagaagtgga tcatgaccgc ggccaagtcc caggactaca agatcgagat ctactcctcc    600
gacgacctga agtcctggaa gctggagtcc gcgttcgcca acgagggctt cctcggctac    660
cagtacgagt gccccggcct gatcgaggtc cccaccgagc aggacccag  caagtcctac    720 tgggtgatgt tcatctccat caaccccggc gccccggccg gcggctcctt caaccagtac    780
ttcgtcggca gcttcaacgg cacccacttc gaggccttcg acaaccagtc ccgcgtggtg    840
gacttcggca aggactacta cgccctgcag accttcttca acaccgaccc gacctacggg    900
agcgccctgg gcatcgcgtg ggcctccaac tgggagtact ccgccttcgt gcccaccaac    960
ccctggcgct cctccatgtc cctcgtgcgc aagttctccc tcaacaccga gtaccaggcc   1020
aacccggaga cggagctgat caacctgaag gccgagccga tcctgaacat cagcaacgcc   1080
```

```
ggcccctgga gccggttcgc caccaacacc acgttgacga aggccaacag ctacaacgtc    1140
gacctgtcca acagcaccgg caccctggag ttcgagctgg tgtacgccgt caacaccacc    1200
cagacgatct ccaagtccgt gttcgcggac ctctccctct ggttcaaggg cctggaggac    1260
cccgaggagt acctccgcat gggcttcgag gtgtccgcgt cctccttctt cctggaccgc    1320
gggaacagca aggtgaagtt cgtgaaggag aaccccctact tcaccaaccg catgagcgtg    1380
aacaaccagc ccttcaagag cgagaacgac ctgtcctact acaaggtgta cggcttgctg    1440
gaccagaaca tcctggagct gtacttcaac gacggcgacg tcgtgtccac caacacctac    1500
ttcatgacca ccgggaacgc cctgggctcc gtgaacatga cgacgggggt ggacaacctg    1560
ttctacatcg acaagttcca ggtgcgcgag gtcaagtga                           1599
```

<210> SEQ ID NO 15
<211> LENGTH: 1599
<212> TYPE: DNA
<213> ORGANISM: Artificial Sequence
<220> FEATURE:
<223> OTHER INFORMATION: S. cerevisiae SUC2 I17C-R28V-N359K enzyme
      variant

<400> SEQUENCE: 15

```
atgctgctgc aggccttcct gttcctgctg gccggcttcg ccgccaagtg cagcgcctcc     60
atgacgaacg agacgtccga cgtgcccctg gtgcacttca cccccaacaa gggctggatg    120
aacgacccca acggcctgtg gtacgacgag aaggacgcca gtggcacct gtacttccag    180 tacaacccga cgacaccgt ctgggggacg cccttgttct ggggccacgc cacgtccgac    240
gacctgacca actgggagga ccagcccatc gccatcgccc gaagcgcaa cgactccggc    300 gccttctccg gctccatggt ggtggactac aacaacaccct ccggcttctt caacgacacc    360
atcgacccgc ccagcgctg cgtggccatc tggacctaca caccccgga gtccgaggag    420 cagtacatct cctacagcct ggacggcggc tacaccttca ccgagtacca gaagaacccc    480
gtgctggccg ccaactccac ccagttccgc gacccgaagg tcttctggta cgagccctcc    540
cagaagtgga tcatgaccgc cggccaagtcc caggactaca agatcgagat ctactcctcc    600
gacgacctga agtcctggaa gctggagtcc cgcttcgcca acgagggctt cctcggctac    660
cagtacgagt gccccggcct gatcgaggtc cccaccgagc aggacccag caagtcctac    720 tgggtgatgt tcatctccat caaccccggc gccccggccg gcggctcctt caaccagtac    780
ttcgtcggca gcttcaacgg cacccacttc gaggccttcg acaaccagtc ccgcgtggtg    840
gacttcggca aggactacta cgccctgcag accttcttca caccgaccc gacctacggg    900 agcgccctgg gcatcgcgtg ggcctccaac tgggagtact ccgccttcgt gccaccaaac    960
ccctggcgct cctccatgtc cctcgtgcgc aagttctccc tcaacaccga gtaccaggcc   1020
aacccggaga cggagctgat caacctgaag gccgagccga tcctgaacat cagcaaggcc   1080
ggcccctgga gccggttcgc caccaacacc acgttgacga aggccaacag ctacaacgtc   1140
gacctgtcca acagcaccgg caccctggag ttcgagctgg tgtacgccgt caacaccacc   1200
cagacgatct ccaagtccgt gttcgcggac ctctccctct ggttcaaggg cctggaggac   1260
cccgaggagt acctccgcat gggcttcgag gtgtccgcgt cctccttctt cctggaccgc   1320
gggaacagca aggtgaagtt cgtgaaggag aaccccctact tcaccaaccg catgagcgtg   1380
aacaaccagc ccttcaagag cgagaacgac ctgtcctact acaaggtgta cggcttgctg   1440
gaccagaaca tcctggagct gtacttcaac gacggcgacg tcgtgtccac caacacctac   1500
```

-continued

| | |
|---|---|
| ttcatgacca ccgggaacgc cctgggctcc gtgaacatga cgacggggt ggacaacctg | 1560 |
| ttctacatcg acaagttcca ggtgcgcgag gtcaagtga | 1599 |

<210> SEQ ID NO 16
<211> LENGTH: 1599
<212> TYPE: DNA
<213> ORGANISM: Artificial Sequence
<220> FEATURE:
<223> OTHER INFORMATION: S. cerevisiae SUC2 I17C-R28V-F366M enzyme variant

<400> SEQUENCE: 16

| | |
|---|---|
| atgctgctgc aggccttcct gttcctgctg gccggcttcg ccgccaagtg cagcgcctcc | 60 |
| atgacgaacg agacgtccga cgtgcccctg gtgcacttca cccccaacaa gggctggatg | 120 |
| aacgacccca cggcctgtg gtacgacgag aaggacgcca gtggcacct gtacttccag | 180 |
| tacaacccga cgacaccgt ctgggggacg cccttgttct ggggccacgc cacgtccgac | 240 |
| gacctgacca ctgggagga ccagcccatc gccatcgccc cgaagcgcaa cgactccggc | 300 |
| gccttctccg gctccatggt ggtggactac aacaacacct ccggcttctt caacgacacc | 360 |
| atcgacccgc ccagcgctg cgtggccatc tggacctaca caccccgga gtccgaggag | 420 |
| cagtacatct cctacagcct ggacggcggc tacaccttca ccgagtacca gaagaacccc | 480 |
| gtgctggccg ccaactccac ccagttccgc gacccgaagg tcttctggta cgagccctcc | 540 |
| cagaagtgga tcatgaccgc ggccaagtcc caggactaca gatcgagat ctactcctcc | 600 |
| gacgacctga gtcctggaa ctggagtcc gcgttcgcca acgagggctt cctcggctac | 660 |
| cagtacgagt gccccggcct gatcgaggtc cccaccgagc aggaccccag caagtcctac | 720 |
| tgggtgatgt tcatctccat caaccccggc gccccggccg gcggctcctt caaccagtac | 780 |
| ttcgtcggca gcttcaacgg cacccacttc gaggccttcg acaaccagtc ccgcgtggtg | 840 |
| gacttcggca aggactacta cgccctgcag accttcttca caccgaccc gacctacggg | 900 |
| agcgccctgg gcatcgcgtg ggcctccaac tgggagtact ccgccttcgt gcccaccaac | 960 |
| ccctggcgct cctccatgtc cctcgtgcgc aagttctccc tcaacaccga gtaccaggcc | 1020 |
| aacccggaga cggagctgat caacctgaag gccgagccga tcctgaacat cagcaacgcc | 1080 |
| ggccccctgga ccggatggc caccaacacc acgttgacga aggccaacag ctacaacgtc | 1140 |
| gacctgtcca cagcaccgg cacctggag ttcagctgg tgtacgccgt caacaccacc | 1200 |
| cagacgatct ccaagtccgt gttcgcggac ctctccctct ggttcaaggg cctggaggac | 1260 |
| cccgaggagt acctccgcat gggcttcgag gtgtccgcgt cctccttctt cctgaccgc | 1320 |
| gggaacagca aggtgaagtt cgtgaaggag aacccctact tcaccaaccg catgagcgtg | 1380 |
| aacaaccagc ccttcaagag cgagaacgac ctgtcctact acaaggtgta cggcttgctg | 1440 |
| gaccagaaca tcctggagct gtacttcaac gacggcgacg tcgtgtccac caacacctac | 1500 |
| ttcatgacca ccgggaacgc cctgggctcc gtgaacatga cgacggggt ggacaacctg | 1560 |
| ttctacatcg acaagttcca ggtgcgcgag gtcaagtga | 1599 |

<210> SEQ ID NO 17
<211> LENGTH: 1599
<212> TYPE: DNA
<213> ORGANISM: Artificial Sequence
<220> FEATURE:
<223> OTHER INFORMATION: S. cerevisiae SUC2 I17C-R28V-N359K-F366M enzyme variant

<400> SEQUENCE: 17

```
atgctgctgc aggccttcct gttcctgctg gccggcttcg ccgccaagtg cagcgcctcc    60
atgacgaacg agacgtccga cgtgcccctg gtgcacttca cccccaacaa gggctggatg   120
aacgacccca acggcctgtg gtacgacgag aaggacgcca agtggcacct gtacttccag   180
tacaacccga acgacaccgt ctgggggacg cccttgttct ggggccacgc cacgtccgac   240
gacctgacca actgggagga ccagcccatc gccatcgccc gaagcgcaa cgactccggc    300
gccttctccg gctccatggt ggtggactac aacaacacct ccggcttctt caacgacacc   360
atcgacccgc cagcgctg cgtggccatc tggacctaca caccccgga gtccgaggag     420
cagtacatct cctacagcct ggacggcggc tacaccttca ccgagtacca agaaccccc    480
gtgctggccg ccaactccac ccagttccgc gacccgaagg tcttctggta cgagccctcc   540
cagaagtgga tcatgaccgc ggccaagtcc caggactaca agatcgagat ctactcctcc   600
gacgacctga gtcctggaa gctggagtcc gcgttcgcca acgagggctt cctcggctac   660
cagtacgagt gccccggcct gatcgaggtc cccaccgagc aggaccccag caagtcctac   720
tgggtgatgt tcatctccat caaccccggc gccccggccg gcggctcctt caaccagtac   780
ttcgtcggca gcttcaacgg cacccacttc gaggccttcg acaaccagtc ccgcgtggtg   840
gacttcggca aggactacta cgccctgcag accttcttca acaccgaccc gacctacggg   900
agcgccctgg gcatcgcgtg ggcctccaac tgggagtact ccgccttcgt gcccaccaac   960
ccctggcgct cctccatgtc cctcgtgcgc aagttctccc tcaacaccga gtaccaggcc  1020
aacccggaga cggagctgat caacctgaag gccgagccga tcctgaacat cagcaaggcc  1080
ggccccctgga gccggatggc caccaacacc acgttgacga aggccaacag ctacaacgtc  1140
gacctgtcca acagcaccgg cacgctggag ttcgagctgg tgtacgccgt caacaccacc  1200
cagacgatct ccaagtccgt gttcgcggac ctctccctct ggttcaaggg cctggaggac  1260
cccgaggagt acctccgcat gggcttcgag gtgtccgcgt cctccttctt cctgaccgc   1320
gggaacagca aggtgaagtt cgtgaaggag aaccccctact tcaccaaccg catgagcgtg  1380
aacaaccagc ccttcaagag cgagaacgac ctgtcctact acaaggtgta cggcttgctg  1440
gaccagaaca tcctggagct gtacttcaac gacggcgacg tcgtgtccac caacacctac  1500
ttcatgacca ccgggaacgc cctgggctcc gtgaacatga cgacggggt ggacaacctg   1560
ttctacatcg acaagttcca ggtgcgcgag gtcaagtga                         1599

<210> SEQ ID NO 18
<211> LENGTH: 1599
<212> TYPE: DNA
<213> ORGANISM: Saccharomyces cerevisiae

<400> SEQUENCE: 18
atgcttttgc aagctttcct tttccttttg ctggttttg cagccaaaat atctgcatca    60
atgacaaacg aaactagcga tagcctttg gtccacttca cccaacaa gggctggatg    120
aatgacccaa atggttgtg gtacgatgaa aaagatgcca atggcatct gtactttcaa    180
tacaacccaa atgacaccgt atggggtacg ccattgttt ggggccatgc tacttccgat    240
gatttgacta attgggaaga tcaacccatt gctatcgctc ccaagcgtaa cgattcaggt   300
gctttctctg gctccatggt ggttgattac aacaacacga gtgggttttt caatgatact   360
attgatccaa gacaaagatg cgttgcgatt tggacttata cactcctga agtgaagag    420
caatacatta gctattctct tgatggtggt tacactttta ctgaatacca aagaaccct    480
```

```
gttttagctg ccaactccac tcaattcaga gatccaaagg tgttctggta tgaaccttct      540
caaaaatgga ttatgacggc tgccaaatca caagactaca aaattgaaat ttactcctct      600
gatgacttga agtcctggaa gctagaatct gcatttgcca atgaaggttt cttaggctac      660
caatacgaat gtccaggttt gattgaagtc ccaactgagc aagatccttc caaatcttat      720
tgggtcatgt ttatttctat caacccaggt gcacctgctg gcggttcctt caaccaatat      780
tttgttggat ccttcaatgg tactcattt gaagcgtttg acaatcaatc tagagtggta      840
gattttggta aggactacta tgccttgcaa actttcttca acactgaccc aacctacggt      900
tcagcattag gtattgcctg ggcttcaaac tgggagtaca gtgcctttgt cccaactaac      960
ccatggagat catccatgtc tttggtccgc aagttttctt tgaacactga atatcaagct     1020
aatccagaga ctgaattgat caatttgaaa gccgaaccaa tattgaacat tagtaatgct     1080
ggtccctggt ctcgttttgc tactaacaca actctaacta aggccaattc ttacaatgtc     1140
gatttgagca actcgactgg taccctagag tttgagttgg tttacgctgt taacaccaca     1200
caaaccatat ccaaatccgt ctttgccgac ttatcacttt ggttcaaggg tttagaagat     1260
cctgaagaat atttgagaat gggttttgaa gtcagtgctt cttccttctt tttggaccgt     1320
ggtaactcta aggtcaagtt tgtcaaggag aacccatatt tcacaaacag aatgtctgtc     1380
aacaaccaac cattcaagtc tgagaacgac ctaagttact ataaagtgta cggcctactg     1440
gatcaaaaca tcttggaatt gtacttcaac gatggagatg tggtttctac aaatacctac     1500
ttcatgacca ccggtaacgc tctaggatct gtgaacatga ccactggtgt cgataatttg     1560
ttctacattg acaagttcca agtaagggaa gtaaaatag                            1599
```

SUCROSE INVERTASE VARIANTS

CROSS-REFERENCE TO RELATED APPLICATIONS

This patent application is the U.S. national stage of PCT/US2020/061280, filed Nov. 19, 2020, which claims the benefit of U.S. Provisional Patent Application No. 62/937,849, filed Nov. 20, 2019 and U.S. Provisional Patent Application No. 62/961,986, filed Jan. 16, 2020, each of which is incorporated by reference in its entirety herein.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 69,087 Byte ASCII (Text) file named "759785_ST25.txt", dated May 17, 2022.

FIELD

The present disclosure relates to generally to the area of genetic engineering of microbes. In particular, the disclosure relates to variants of the enzyme sucrose invertase and related methods.

BACKGROUND

Heterologous expression of sucrose invertase from *Saccharomyces cerevisiae* (ScSUC2) enables the conversion of sucrose in the culture medium into glucose and fructose for consumption by the host cells. For some host cells cultured at pH 5, adequate sucrose hydrolysis to support the fermentation is typically observed. However, for some host cells cultured at pH 7, the addition of exogenous invertase is often required to ensure sufficient sucrose hydrolysis at pH 7. This is because ScSUC2 activity is optimal at pH 4.5, but the enzyme retains only 20% of its maximal activity at pH 7.

SUMMARY

Various embodiments contemplated herein may include, but need not be limited to, one or more of the following:

Embodiment 1: A sucrose invertase variant including a polypeptide sequence having at least 80%, 85%, 90%, 91%, 92%, 93%, 94%, 95%, 96%, 97%, 98%, or 99% amino acid sequence identity to a full-length wild-type *Saccharomyces cerevisiae* sucrose invertase having the amino acid sequence of SEQ ID NO:1, or to a functional subsequence thereof, wherein the sucrose invertase variant includes a modification including at least one amino acid substitution in at least one amino acid residue position selected from the group consisting of positions 17, 28, 359, and 366, wherein the amino acid residue positions correspond to amino acid residues numbered from the N-terminus of SEQ ID NO:1.

Embodiment 2: The sucrose invertase variant of embodiment 1, wherein the functional subsequence is a subsequence of SEQ ID NO:1 that lacks predicted transit peptide amino acid residues 1-19 of SEQ ID NO: 1.

Embodiment 3: The sucrose invertase variant of embodiment 1 or embodiment 2, wherein the one or more amino acid substitutions are selected from the group consisting of: (a) an amino acid substitution from isoleucine to cysteine at amino acid residue position 17 (I17C); (b) an amino acid substitution from arginine to valine at amino acid residue position 28 (R28V); (c) an amino acid substitution from asparagine to lysine at amino acid residue position 359 (N359K); and (d) an amino acid substitution from phenylalanine to methionine at amino acid residue position 366 (F366M).

Embodiment 4: The sucrose invertase variant of embodiment 1 or embodiment 2, wherein the one or more amino acid substitutions comprise an amino acid substitution at amino acid residue position 17.

Embodiment 5: The sucrose invertase variant of embodiment 4, wherein the amino acid substitution at amino acid residue position 17 includes an amino acid substitution from isoleucine to cysteine (I17C).

Embodiment 6: The sucrose invertase variant of embodiment 1 or embodiment 2, wherein the one or more amino acid substitutions comprise a substitution at amino acid residue position 28.

Embodiment 7: The sucrose invertase variant of embodiment 6, wherein the amino acid substitution at amino acid residue position 28 includes an amino acid substitution from arginine to valine (R28V).

Embodiment 8: The sucrose invertase variant of embodiment 1 or embodiment 2, wherein the one or more amino acid substitutions comprise an amino acid substitution at amino acid residue position 359.

Embodiment 9: The sucrose invertase variant of embodiment 8, wherein the amino acid substitution at amino acid residue position 359 includes an amino acid substitution from asparagine to lysine (N359K).

Embodiment 10: The sucrose invertase variant of embodiment 1 or embodiment 2, wherein the one or more amino acid substitutions comprise an amino acid substitution at amino acid residue position 366.

Embodiment 11: The sucrose invertase variant of embodiment 10 wherein the amino acid substitution at amino acid residue position 366 includes an amino acid substitution from phenylalanine to methionine (F366M).

Embodiment 12: The sucrose invertase variant of any preceding embodiments, wherein the variant includes at least two amino acid substitutions.

Embodiment 13: The sucrose invertase variant of embodiment 12, wherein the at least two amino acid substitutions comprise amino acid substitutions at a pair of amino acid residue positions selected from the group consisting of (a) 17 and 28; (b) 17 and 359; (c) 17 and 366; (d) 28 and 359; (e) 28 and 366; and (f) 359 and 366.

Embodiment 14: The sucrose invertase variant of embodiment 13, wherein the at least two amino acid substitutions comprise a pair of amino acid substitutions selected from the group consisting of (a) I17C and R28V; (b) I17C and N359K; (c) I17C and F366M; (d) R28V and N359K; (e) R28V and F366M; and (f) N359K and F366M.

Embodiment 15: The sucrose invertase variant of embodiment 14, wherein the at least two amino acid substitutions comprise I17C and R28V.

Embodiment 16: The sucrose invertase variant of any preceding embodiments, wherein the sucrose invertase variant includes at least three amino acid substitutions.

Embodiment 17: The sucrose invertase variant of embodiment 16, wherein the at least three amino acid substitutions comprise amino acid substitutions at a group of amino acid residue positions selected from: (a) 17, 28, and 359; (b) 17, 28, and 366; (c) 17, 359, and 366; and (d) 28, 359, and 366.

Embodiment 18: The sucrose invertase variant of embodiment 17, wherein the at least three amino acid substitutions comprise a group of amino acid substitutions selected from:

(a) R17C, R28V, and N359K; (b) R17C, R28V, and F366M; (c) R17C, N359K, and F366M; and (d) R28V, N359K, and F366M.

Embodiment 19: The sucrose invertase variant of embodiment 16, wherein the at least three amino acid substitutions comprise R17C, R28V, and N359K.

Embodiment 20: The sucrose invertase variant of embodiment 16, wherein the at least three amino acid substitutions comprise R17C, R28V, and F366M.

Embodiment 21: The sucrose invertase variant of any preceding embodiments, wherein the sucrose invertase variant includes at least four amino acids substitutions.

Embodiment 22: The sucrose invertase variant of embodiment 21, wherein the at least four amino acid substitutions comprise R17C, R28V, N359K, and F366M.

Embodiment 23: The sucrose invertase variant of any one of embodiments 1-22, wherein said amino acid sequence identity is at least 95%, 96%, 97%, or 99%.%, or optionally, wherein the sucrose invertase variant comprises: (a) an amino acid sequence of SEQ ID NO:2, or a subsequence of SEQ ID NO:2 that lacks predicted transit peptide amino acid residues 1-19 of SEQ ID NO:2; (b) an amino acid sequence of SEQ ID NO:3, or a subsequence of SEQ ID NO:3 that lacks predicted transit peptide amino acid residues 1-19 of SEQ ID NO:3; (c) an amino acid sequence of SEQ ID NO:4, or a subsequence of SEQ ID NO:4 that lacks predicted transit peptide amino acid residues 1-19 of SEQ ID NO:4; (d) an amino acid sequence of SEQ ID NO: 5, or a subsequence of SEQ ID NO:5 that lacks predicted transit peptide amino acid residues 1-19 of SEQ ID NO:5; (e) an amino acid sequence of SEQ ID NO:6, or a subsequence of SEQ ID NO:6 that lacks predicted transit peptide amino acid residues 1-19 of SEQ ID NO:6; (f) an amino acid sequence of SEQ ID NO: 7, or a subsequence of SEQ ID NO:7 that lacks predicted transit peptide amino acid residues 1-19 of SEQ ID NO:7; (g) an amino acid sequence of SEQ ID NO:8, or a subsequence of SEQ ID NO:8 that lacks predicted transit peptide amino acid residues 1-19 of SEQ ID NO:8; or (h) an amino acid sequence of SEQ ID NO:9, or a subsequence of SEQ ID NO:9 that lacks predicted transit peptide amino acid residues 1-19 of SEQ ID NO:9.

Embodiment 24: The sucrose invertase variant of any one of embodiments 1-23, wherein the sucrose invertase variant has an enhanced ability to hydrolyze sucrose into glucose and fructose at pH 7, as compared to an unmodified form of the sucrose invertase variant.

Embodiment 25: The sucrose invertase variant of any one of embodiments 1-24, wherein the sucrose invertase variant has an enhanced ability to hydrolyze sucrose into glucose and fructose at pH 4, 4.5, 5, 5.5, 6, 6.5, 7.5, or 8, as compared to an unmodified form of the sucrose invertase variant.

Embodiment 26: The sucrose invertase variant of embodiment 24 or 25, wherein the enhanced ability to hydrolyze sucrose into glucose and fructose is at least 10%, 15%, 20%, 25%, 30%, 35%, 40%, 45%, 50%, 55%, 60%, 65%0, 70%, 75%, 80%, 85%, 90%, 95%, 100%, 105%, 110%, 115%, 120%, 125%, 130%, 135%, 140%, 145%, 150%, 160%, 170%, 180%, 190% or 200%, as compared to an unmodified form of the sucrose invertase variant.

Embodiment 27: The sucrose invertase variant of any one of embodiments 24-26, wherein the enhanced ability to hydrolyze sucrose into glucose and fructose is observed at a temperature between 25° C. and 35° C., inclusive.

Embodiment 28: A polynucleotide including a nucleotide sequence encoding the sucrose invertase variant of any one of embodiments 1-27.

Embodiment 29: The polynucleotide of embodiment 28, wherein the nucleotide sequence is codon-optimized for expression in a selected host cell.

Embodiment 30: The polynucleotide of embodiment 29, wherein the host cell is a *Prototheca moriformis* cell.

Embodiment 31: The polynucleotide of any one of embodiments 28-30, wherein the nucleotide sequence has at least 60%, 65%, 70%, 75%, 80%, 85%, 90%, 91%, 92%, 93%, 94%, 95%, 96%, 97%, 98%, or 99% nucleotide sequence identity with SEQ ID NO:11, SEQ ID NO:17, SEQ ID NO:18, or a functional subsequence thereof.

Embodiment 32: The polynucleotide of embodiment 31, wherein the nucleotide sequence identity is at least 95%, 96%, 97%, 98%, or 99%, or optionally, the polynucleotide comprises: (a) the nucleotide sequence of SEQ ID NO:11; (b) the nucleotide sequence of SEQ ID NO:12; (c) the nucleotide sequence of SEQ ID NO:13; (d) the nucleotide sequence of SEQ ID NO:14; (e) the nucleotide sequence of SEQ ID NO:15; (f) the nucleotide sequence of SEQ ID NO:16; (f) the nucleotide sequence of SEQ ID NO:17; or (g) the nucleotide sequence of SEQ ID NO:18.

Embodiment 33: An expression construct including the polynucleotide of any one of embodiments 28-32, wherein the polynucleotide is operably linked to a promoter.

Embodiment 34: An engineered cell including the polynucleotide of any one of embodiments 28-32 or the expression construct of embodiment 33.

Embodiment 35: The engineered cell of embodiment 34, wherein the engineered cell includes two or more copies of any one of the polynucleotides of any one of embodiments 28-32 or includes at least two different polynucleotides selected from the polynucleotides of any one of embodiments 28-32.

Embodiment 36: The engineered cell of embodiment 34 or embodiment 35, wherein the engineered cell includes an engineered microbial cell.

Embodiment 37: The engineered cell of embodiment 36, wherein the engineered microbial cell includes an engineered algal cell.

Embodiment 38: The engineered cell of embodiment 37, wherein the engineered algal cell includes an engineered *Prototheca* cell.

Embodiment 39: The engineered cell of embodiment 37, wherein the engineered algal cell includes an engineered *Prototheca moriformis* cell.

Embodiment 40: The engineered cell of embodiment 36, wherein the engineered microbial cell is an engineered yeast cell.

Embodiment 41: The engineered cell of any one of embodiments 34-40, wherein the engineered cell expresses the sucrose invertase variant(s) of any one of embodiments 1-27.

Embodiment 42: The engineered cell of any one of embodiments 34-41, wherein the engineered cell has an enhanced ability to hydrolyze sucrose into glucose and fructose at pH 7, as compared to a cell of the same type that has been engineered to express an unmodified form of any sucrose invertase variant expressed by the engineered cell.

Embodiment 43: The engineered cell of embodiment 42, wherein the engineered cell also has an enhanced ability to hydrolyze sucrose into glucose and fructose at pH 4, 4.5, 5, 5.5, 6, 6.5, 7.5, or 8, as compared to a cell of the same type that has been engineered to express an unmodified form of any sucrose invertase variant expressed by the engineered cell.

Embodiment 44: The engineered cell of embodiment 42 or embodiment 43, wherein the enhanced ability to hydrolyze sucrose into glucose and fructose is observed when the engineered cell is cultured at a temperature between 25° C. and 35° C., inclusive.

Embodiment 45: The engineered cell of any of embodiments 1-44, wherein the engineered cells further includes at least one heterologous polynucleotide that encodes a product of interest or a polypeptide that participates in producing a product of interest.

Embodiment 46: The engineered cell of embodiment 45, wherein the product of interest is a fatty acid, a lipid, a sterol, an enzyme, a fusion protein, an amino acid, an antioxidant, an antibody, or a pharmaceutical product.

Embodiment 47: A method of producing a product of interest, the method including culturing the engineered cell of embodiment 45 or embodiment 46 in a culture medium including sucrose as a carbon source, whereby the product of interest is produced, and optionally recovering the product of interest.

Embodiment 48: The method of embodiment 47, wherein the product of interest is a fatty acid, a lipid, a sterol, an enzyme, a fusion protein, an amino acid, an antioxidant, an antibody, or a pharmaceutical product.

Embodiment 49: A culture including the engineered cell of any one of embodiments 34-48 and a culture medium.

Embodiment 50: A method of culturing the engineered cell of any one of embodiments 34-48, wherein the method includes culturing the engineered cell in a culture medium.

Embodiment 51: The culture of embodiment 49 or the method of embodiment 50, wherein the culture medium includes sucrose as a carbon source.

Embodiment 52: The culture or method of any one of embodiments 49-51, wherein the culture medium has a pH of about 7.

Embodiment 53: The culture or method of any one of embodiments 49-51, wherein the culture medium has a pH of 4, 4.5, 5, 5.5, 6, 6.5, 7.5, or 8.

Embodiment 54: A method of producing a sucrose invertase variant, the method including culturing an engineered cell according to any of embodiments 34-48 under suitable conditions, such that at least one sucrose invertase variant is produced.

Embodiment 55: The method of embodiment 54, wherein the method further includes recovering at least one sucrose invertase variant from the culture and/or the engineered cell.

Embodiment 56: The method of embodiment 55, wherein the method further includes purifying at least one sucrose invertase variant.

Embodiment 57: A composition including the sucrose invertase variant of any one of embodiments 1-27.

Embodiment 58: A method of hydrolyzing a substrate, the method comprising contacting the sucrose invertase variant of any one of embodiments 1-27 with the substrate under suitable conditions, such that the sucrose invertase variant hydrolyzes the substrate.

Embodiment 59: The method of embodiment 58, wherein the substrate is sucrose, and the sucrose invertase variant hydrolyzes the substrate into sucrose into glucose and fructose.

Embodiment 60: The method of embodiment 58 or embodiment 59, wherein said contacting occurs in a cell or cell culture.

Embodiment 61: The method of embodiment 58 or embodiment 59, wherein said contacting occurs in an in vitro reaction mixture.

Embodiment 62: A method of producing an engineered cell of any one of embodiments 34-46, comprising the step of introducing into the cell expression of the sucrose invertase variant of any one of embodiments 1-27.

DETAILED DESCRIPTION

Figure 1:
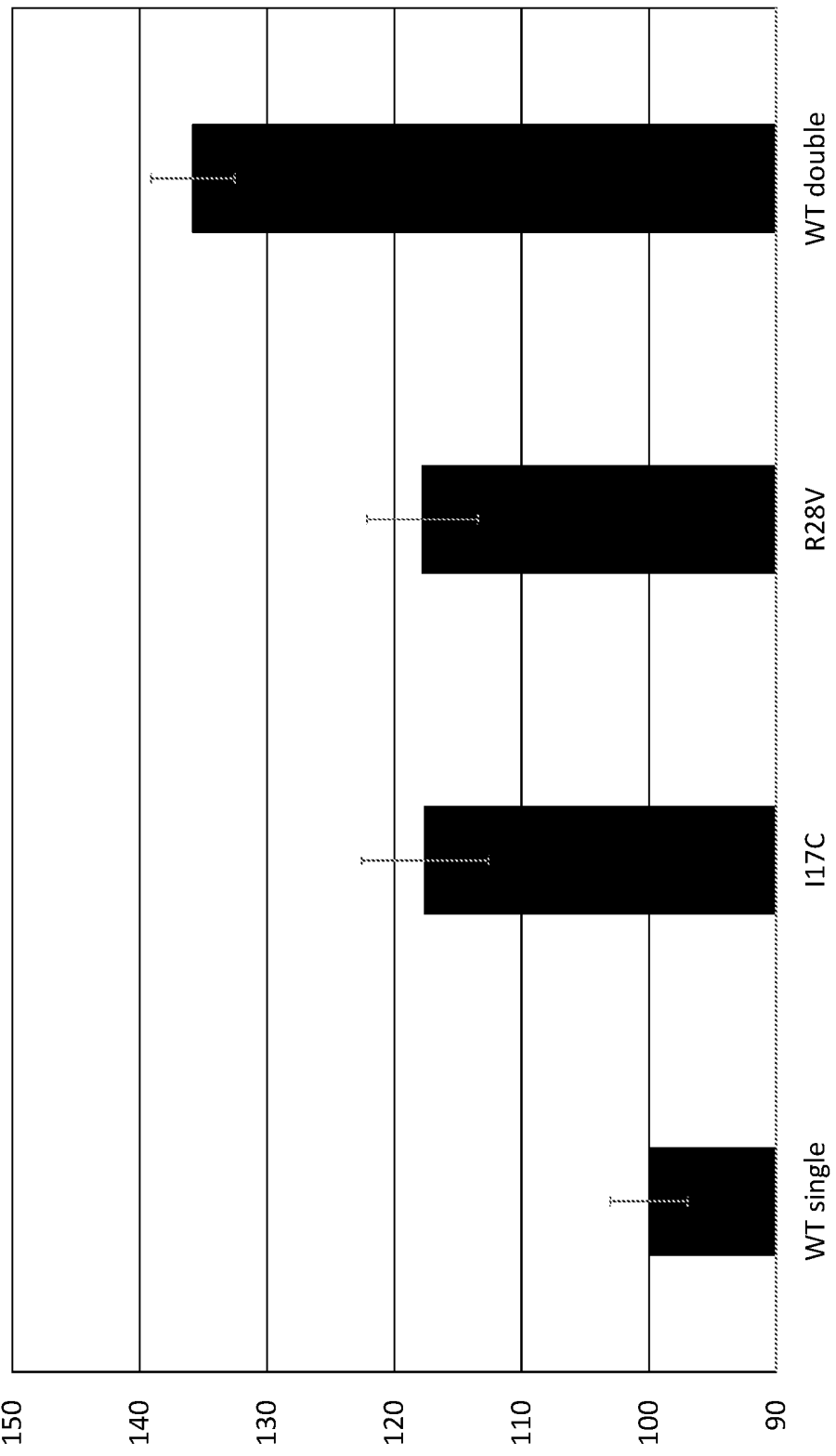
FIG. 1: Sucrose hydrolytic activity of two ScSUC2 variants (I17C and R28V) at pH 7, 28° C. For comparison, controls with single copy and double copies of the wild-type ScSUC2 gene were included. Assay conditions are described in Example 1. Outliers are omitted from the calculations.

The present disclosure provides variants of sucrose invertase with an enhanced ability to hydrolyze sucrose into glucose and fructose in fermentations carried out, for example, at pH 7, as well as related compositions, cultures, and methods.

Definitions

Terms used in the claims and specification are defined as set forth below unless otherwise specified.

As used herein, a "sucrose invertase" refers to an enzyme that catalyzes the hydrolysis of sucrose into glucose and fructose. Alternative names for sucrose invertase include EC 3.2.1.26, beta-fructofuranosidase, invertase, saccharase, glucosucrase, beta-h fructosidase, beta-fructosidase, invertin, sucrase, maxinvert L 1000, fructosylinvertase, alkaline invertase, and acid invertase. Sucrose invertase not only hydrolyzes sucrose to its monosaccharide constituents, but at a much slower rate it can also remove terminal 0-fructosyl residues from short-chain oligosaccharides, such as raffinose and kestoses. In addition, sucrose invertases can carry out transfructosylation reactions between its substrate molecules resulting in formation of oligosaccharides such as kestotrioses when sucrose serves as both the donor and acceptor.

A sucrose invertase has an "enhanced ability to hydrolyze sucrose into glucose and fructose" if the enzyme enables the production of more glucose and fructose from sucrose, as compared to a reference sucrose invertase (e.g., a wild-type sucrose invertase) acting under the same (or essentially the same) conditions. This enhancement in activity can be measured by measuring residual substrate (e.g., sucrose) after a period of time and/or increase in product (glucose and/or fructose) over a period of time, as e.g. exemplified in Example 1. Example 1 describes sucrose invertase variants that are expressed in illustrative host cells (*Prototheca moriformis*) and cultured in the presence of sucrose. Sucrose invertase variants were identified that, when expressed in cells cultured at pH 7, hydrolyzed more sucrose, than the unmodified, wild-type sucrose invertase, when expressed in the same cell type and cultured under the same conditions.

Numbering of a given amino acid polymer or nucleic acid polymer "corresponds to" or is "relative to" the numbering of a selected amino acid polymer or nucleic acid polymer when the position of any given polymer component (e.g., amino acid, nucleotide, also referred to generically as a "residue") is designated by reference to the same or to an equivalent position (e.g., based on an optimal alignment or a consensus sequence) in the selected amino acid or nucleic acid polymer, rather than by the actual numerical position of the component in the given polymer.

A "variant" is a polypeptide comprising a sequence that differs in one or more amino acid position(s) from that of a parent polypeptide sequence (e.g., by substitution, deletion, or insertion). The differences are termed "modifications." A variant may comprise a sequence that differs from the parent polypeptide sequence in up to 30% of the total number of residues of the parent polypeptide sequence, such as in up to 30%, 25%, 20%, 15%, 10%, 9%, 8%, 7%, 6%, 5%, 4%, 3%, 2% or 1% of the total number of residues of the parent polypeptide sequence. As used herein, the term "variant" refers to a polypeptide that includes an amino acid sequence that is not naturally occurring or some other structural modification that is not found in nature.

"Naturally occurring" as applied to a composition that can be found in nature as distinct from being artificially produced by man. For example, a polypeptide or polynucleotide that is present in an organism (including viruses, bacteria, protozoa, insects, plants or mammalian tissue) that can be isolated from a source in nature and that has not been intentionally modified by man in the laboratory is naturally occurring. "Non-naturally occurring" (also termed "synthetic" or "artificial") as applied to an object means that the object is not naturally-occurring—i.e., the object cannot be found in nature as distinct from being artificially produced by man.

"Microalgae" are microbial organisms that contain a chloroplast or plastid, and optionally that are capable of performing photosynthesis. Microalgae include obligate photoautotrophs, which cannot metabolize a fixed carbon source as energy, as well as heterotrophs, which can live solely off of a fixed carbon source. Microalgae include unicellular organisms that separate from sister cells shortly after cell division, such as *Chlamydomonas*, as well as microbes such as, for example, Volvox, which is a simple multicellular photosynthetic microbe of two distinct cell types. Microalgae include eukaryotic Chlorophyceae such as *Chlorella, Dunaliella,* and *Prototheca*. Microalgae also include other microbial photosynthetic organisms that exhibit cell-cell adhesion, such as *Agmenellum, Anabaena,* and *Pyrobotrys*. Microalgae also include obligate heterotrophic microorganisms that have lost the ability to perform photosynthesis, such as certain dinoflagellate algae species and species of the genus *Prototheca* or *Chlorella*.

An "oleaginous" cell is a non-human cell capable of producing at least 20% lipid by dry cell weight, naturally or through recombinant or classical strain improvement. An "oleaginous microbe" or "oleaginous microorganism is a microbe, including a microalga that is oleaginous.

As used with respect to polypeptides or polynucleotides, the term "isolated" refers to a polypeptide or polynucleotide that has been separated from at least one other component that is typically present with the polypeptide or polynucleotide. Thus, a naturally occurring polypeptide is isolated if it has been purified away from at least one other component that occurs naturally with the polypeptide or polynucleotide. A recombinant polypeptide or polynucleotide is isolated if it has been purified away from at least one other component present when the polypeptide or polynucleotide is produced.

The terms "polypeptide" and "protein" are used interchangeably herein to refer a polymer of amino acids, and unless otherwise limited, include atypical amino acids that can function in a similar manner to naturally occurring amino acids.

The term "sequence", as used in connection with a polypeptide or nucleic acid polymer refers to the order of monomers making up the polymer or the sub-polymer or fragment having that sequence.

A "subsequence" of an amino acid or nucleotide sequence is a portion of a larger sequence or the peptide or nucleic acid sub-polymer or fragment characterized by the portion of the larger sequence. A subsequence of an amino acid or nucleotide sequence can lack one or more of an N-terminal or 5' sequence, respectively, an internal sequence, and/or a C-terminal or 3' sequence respectively.

A "functional subsequence" of a larger amino acid sequence is one that, when present in a peptide or polypeptide, confers at least one function associated with the larger sequence. A functional subsequence of a larger nucleotide sequence that encodes a protein having at least one biological function is a subsequence of the larger nucleotide sequence, wherein the subsequence encodes a functional subsequence of the protein.

The term "percent sequence identity," in the context of two or more amino acid or nucleic acid sequences, refers to two or more sequences or subsequences that are the same or have a specified percentage of amino acid residues or nucleotides that are the same, when compared and aligned for maximum correspondence, as measured using a sequence comparison algorithm or by visual inspection. For sequence comparison to determine percent nucleotide or amino acid identity, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence (e.g., SEQ ID NOs:1 or 11), based on the designated program parameters. Optimal alignment of sequences for comparison can be conducted using the NCBI BLAST software (ncbi.nlm.nih.gov/BLAST/) set to default parameters. For example, to compare two nucleic acid sequences, one may use BLASTN program with its default parameters: (General Parameters: Max target sequences: 100; Expect threshold: 10; Word size: 28, Max matches in a query range: 0; Scoring parameters: Match/Mismatch Scores: 1, −2; Gap Costs: linear). For polypeptide sequence alignment and sequence identity calculations, BLASTP program can be used with its default parameters (General Parameters: Max target sequences: 100, Expect threshold: 10; Word size: 6; Max matches in a query range: 0; Scoring Parameters: Matrix=BLOSUM62; Gap costs: Existence=11, Extension=1; Compositional adjustments=Conditional compositional score). In certain embodiments, the sequence identity between two polypeptide sequences is determined using the Needleman-Wunsch algorithm (Needleman and Wunsch, 1970, J. Mol. Biol. 48: 443-453) as implemented in the Needle program of the EMBOSS package (https://www.ebi.ac.uk/Tools/psa/emboss_needle/) from the European Bioinformatics Institute, using its default parameters (Matrix: BLOSUM62; Gap Open: 10; Gap Extend: 0.5; End Gap Penalty: false; End Gap Open: 10; End Gap Extend: 0.5). In certain embodiments, the sequence identity between two nucleic acid sequences is determined using the Needleman-Wunsch algorithm described above using its default parameters (Matrix: DNAfull; Gap Open: 10; Gap Extend: 0.5; End Gap Penalty; false; End Gap Open: 10; End Gap Extend: 0.5). In certain embodiments, the sequence alignment of two or more sequences are performed using Clustal Omega or ClustalW using the suggested default parameters (Dealign input sequences: no; Mbed-like clustering guide-tree: yes; Mbed-like clustering iteration: yes; number of combined iterations: default(0); Max guide tree iterations: default; Max HMM iterations: default; Order: aligned.

As used with reference to polypeptides, the term "wild-type" refers to any polypeptide having an amino acid sequence present in a polypeptide from a naturally occurring organism, regardless of the source of the molecule; i.e., the term "wild-type" refers to sequence characteristics, regardless of whether the molecule is purified from a natural source; expressed recombinantly, followed by purification; or synthesized.

The term "mutation" shall mean a change in a protein, polypeptide, or peptide sequence or subsequence produced by altering one or more nucleotides in a nucleotide coding for the protein, polypeptide, or peptide, however the alteration is obtained. For example, a mutation can be produced randomly, by PCR mutation, by synthesis of entire gene, or any other method.

The term "vector" is used herein to describe a DNA construct containing a polynucleotide. Such a vector can be propagated stably or transiently in a host cell. The vector can, for example, be a plasmid, a viral vector, or simply a potential genomic insert. Once introduced into a suitable host, the vector may replicate and function independently of the host genome, or may, in some instances, integrate into the host genome.

As used herein, the terms "expression vector" or "expression construct" or "expression cassette" refer to a nucleic acid construct, generated recombinantly or synthetically, with a series of specified nucleic acid elements that permit transcription of a particular nucleic acid in a host cell. The expression vector can be part of a plasmid, virus, or nucleic acid fragment. An "expression cassette" includes a coding nucleic acid (CDS) to be transcribed operably linked to a promoter and a 3'UTR. Optionally, and in the Examples below, the promoter of an expression cassette is a heterologous promoter.

"Exogenous gene" refers to a nucleic acid transformed into a cell. The exogenous gene may be from a different species, or from the same species (and so homologous) relative to the cell being transformed. Thus, an exogenous gene can include a homologous gene that occupies a different location in the genome of the cell or is under different control relative to the endogenous copy of the gene. An exogenous gene may be present in more than one copy in the cell. An exogenous gene may be maintained in a cell as an insertion into the genome or as an episomal molecule.

As applied to amino acid sequences in a cell, the term "heterologous" refers to an amino acid sequence that is not encoded by a naturally occurring gene in that cell. Heterologous amino acid sequences can be derived, e.g., from other species or produced in any way known in the art, including, e.g., swapping of individual domains with an altered and/or non-naturally occurring domain, introduction of point mutations, introduction of altered or non-naturally occurring subsequences, or deletion of single amino acid residues, subsequences and/or domains.

An "inducible promoter" is one that mediates transcription of an operably linked gene in response to a particular stimulus.

As used herein, the phrase "in operable linkage" refers to a functional linkage between two nucleic acid sequences, such a control sequence (typically a promoter) and the linked sequence (typically a sequence that encodes a protein, also called a coding sequence). A promoter is in operable linkage with an exogenous gene if it can mediate transcription of the gene.

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription.

"Recombinant" is a cell, nucleic acid, protein or vector that has been modified due to the introduction of an exogenous nucleic acid or the alteration of a native nucleic acid. Thus, e.g., recombinant (host) cells can express genes that are not found within the native (non-recombinant) form of the cell or express native genes differently than those genes are expressed by a non-recombinant cell. Recombinant cells can, without limitation, include recombinant nucleic acids that encode a gene product or suppression elements such as mutations, knockouts, knockdowns, antisense, interfering RNA (RNAi) or dsRNA that reduce the levels of active gene product in a cell. A "recombinant nucleic acid" is a nucleic acid originally formed in vitro, in general, by the manipulation of nucleic acid, e.g., using polymerases, ligases, exonucleases, and endonucleases, using chemical synthesis, or otherwise is in a form not normally found in nature. Recombinant nucleic acids may be produced, for example, by placing two or more nucleic acids in operable linkage. Thus, an isolated nucleic acid or an expression vector formed in vitro by nucleic by ligating DNA molecules that are not normally joined in nature, are both considered recombinant for the purposes of this description. Recombinant nucleic acids can also be produced in other ways; e.g., using chemical DNA synthesis. Once a recombinant nucleic acid is made and introduced into a host cell or organism, it may replicate using the in vivo cellular machinery of the host cell; however, such nucleic acids, once produced recombinantly, although subsequently replicated intracellularly, are still considered recombinant for purposes of this description. Similarly, a "recombinant protein" is a protein made using recombinant techniques, i.e., through the expression of a recombinant nucleic acid.

A "transit peptide" is an amino acid sequence that directs the trafficking of a polypeptide fused to the signal sequence. In connection with plastidic cells expressing the polypeptide, the transit peptide may direct trafficking of the polypeptide to the plastid (i.e., a plastid targeting peptide).

The term "polynucleotide" refers to a deoxyribonucleotide or ribonucleotide polymer, and unless otherwise limited, includes known analogs of natural nucleotides that can function in a similar manner to naturally occurring nucleotides. The term "polynucleotide" refers to any form of DNA or RNA, including, for example, genomic DNA; complementary DNA (cDNA), which is a DNA representation of mRNA, usually obtained by reverse transcription of messenger RNA (mRNA) or amplification; DNA molecules produced synthetically or by amplification; and mRNA. The term "polynucleotide" encompasses double-stranded nucleic acid molecules, as well as single-stranded molecules. In double-stranded polynucleotides, the polynucleotide strands need not be coextensive (i.e., a double-stranded polynucleotide need not be double-stranded along the entire length of both strands).

The term "host cell" refers to a cell capable of maintaining a vector either transiently or stably. Host cells include, without limitation, bacterial cells, yeast cells, insect cells, algal cells (e.g., microalgal cells), plant cells and mammalian cells. Other host cells known in the art, or which become known, are also suitable for use.

As used herein, the term "complementary" refers to the capacity for precise pairing between two nucleotides. For example, if a nucleotide at a given position of a nucleic acid molecule is capable of hybridizing with a nucleotide of another nucleic acid molecule, then the two nucleic acid molecules are considered to be complementary to one another at that position. The term "substantially complementary" describes sequences that are sufficiently complementary to one another to allow for specific hybridization under stringent hybridization conditions. In various embodiments, the variant genes encoding variant ScSUC2 genes disclosed below can be replaced with a substantially complementary gene having suitable activity.

The phrase "stringent hybridization conditions" generally refers to a temperature about 5° C. lower than the melting temperature (Tm) for a specific sequence at a defined ionic strength and pH. Exemplary stringent conditions suitable for achieving specific hybridization of most sequences are a temperature of at least about 60° C. and a salt concentration of about 0.2 molar at pH 7.0.

Sucrose Invertase Variants

Sucrose invertases have been widely studied in plants, fungi, such as yeasts (e.g., *Saccharomyces cerevisiae*), and bacteria (e.g., *Escherichia coli*). Sucrose invertase variants can be produced from any sucrose invertase derived from these or other organisms. A number of different sucrose invertases have been derived from *Saccharomyces cerevisiae*, for example. These include a wild-type sucrose invertase whose full-length amino acid sequence (including a predicted transit peptide sequence) is SEQ ID NO:1. The predicted transit peptide for this enzyme consists of amino acid residues 1-19 of SEQ ID NO:1. Sucrose invertase variants having an enhanced ability to hydrolyze sucrose into glucose and fructose at pH 7 can be produced from any active sucrose invertase or any functional fragment thereof.

Proteins

The present disclosure provides a sucrose invertase variant comprising one or more modifications that provide an enhanced ability to hydrolyze sucrose into glucose and fructose, as compared to the unmodified sucrose invertase. In particular, a sucrose invertase variant provides an enhanced ability to hydrolyze sucrose at pH 7. The unmodified sucrose invertase can be a naturally occurring sucrose invertase or a non-naturally occurring sucrose invertase, e.g., one that already includes, e.g., one or more other amino acid substitutions, deletions, or insertions. In other words, the "unmodified" sucrose invertase is the sucrose invertase selected for modification to provide an enhanced ability to hydrolyze sucrose into glucose and fructose at pH 7.

In various embodiments, sucrose invertase variants can have one, two, three, four, five, six, seven, eight, nine, 10, 11, 12, 13, 14, 15, 16, 17, 18, 19, or 20 or more modifications. In various embodiments, the modifications can include amino acid substitutions, deletions, insertions, or combinations thereof.

The one or more modifications can be in different domains of the sucrose invertase. These include, for example, modifications (e.g., amino acids substitutions) within: (1) a predicted transit peptide sequence extending from amino acid residues 1-19, (2) an N-terminal region extending from amino acid residues 20-97, and/or (3) a C-terminal region extending from amino acid residue 98 to the C-terminus, wherein the amino acid residues correspond to amino acid residues numbered from the N-terminus of the transit peptide sequence of the unmodified sucrose invertase from *Saccharomyces cerevisiae* (ScSUC2), having the amino acid sequence SEQ ID NO:1. For example, the one or more modifications can include amino acid substitutions at positions that correspond to: (1) amino acid residue 17 of SEQ ID NO:1, (2) amino acid residue 28 of SEQ ID NO:1, and (3) amino acid residues 359 and/or 366 of SEQ ID NO:1 (respectively). In some embodiments the one or more modifications can include the following amino acid substitutions: (1) an amino acid substitution from isoleucine to a hydroxyl- or sulfur-containing amino acid, e.g. selected from cysteine, serine, threonine and methionine, at the position that corresponds to amino acid residue 17 of SEQ ID NO:1, (2) an amino acid substitution from arginine to an aliphatic or sulfur-containing amino acid e.g. selected from valine, leucine, isoleucine, alanine or methionine, at the position that corresponds to amino acid residue 28 of SEQ ID NO:1, (3) an amino acid substitution from asparagine to a basic amino acid, e.g. selected from lysine, arginine or histidine, at the position that corresponds to amino acid residue 359 of SEQ ID NO: 1, and/or (4) an amino acid substitution from phenylalanine to a sulfur-containing or aliphatic amino acid, e.g. selected from an methionine, leucine, isoleucine, valine or alanine at the position that corresponds to amino acid residue 366 of SEQ ID NO:1 (respectively). In some embodiments the one or more modifications can include the following amino acid substitutions: (1) an amino acid substitution from isoleucine to cysteine at the position that corresponds to amino acid residue 17 of SEQ ID NO:1, (2) an amino acid substitution from arginine to valine at the position that corresponds to amino acid residue 28 of SEQ ID NO:1, (3) an amino acid substitution from asparagine to lysine at the position that corresponds to amino acid residue 359 of SEQ ID NO: 1, and/or (4) an amino acid substitution from phenylalanine to methionine at the position that corresponds to amino acid residue 366 of SEQ ID NO:1 (respectively).

In some embodiments, the sucrose invertase variant includes amino acid substitutions at positions that correspond to: amino acid residue 17 of SEQ ID NO:1, amino acid residue 28 of SEQ ID NO:1, amino acid residue 359 of SEQ ID NO:1, and/or amino acid residue 366 of SEQ ID NO: 1. In some embodiments, the sucrose invertase variant includes the following four amino acid substitutions: an amino acid substitution from isoleucine to cysteine at the position that corresponds to amino acid residue 17 of SEQ ID NO:1, an amino acid substitution from arginine to valine at the position that corresponds to amino acid residue 28 of SEQ ID NO:1, an amino acid substitution from asparagine to lysine at the position that corresponds to amino acid residue 359 of SEQ ID NO:1, and an amino acid substitution from phenylalanine to methionine at the position that corresponds to amino acid residue 366 of SEQ ID NO:1.

Sucrose invertase variants, such as those described above, are generally produced by modifying a "starting" (unmodified) sucrose invertase. The starting sucrose invertase can be derived from any organism that has this enzyme and can depend on the host cell in which it is to be expressed. Generally, the starting sucrose invertase is one that expresses well in the host cell to be used for expression. In some embodiments, the starting sucrose invertase is a (naturally occurring or non-naturally occurring) sucrose invertase that derives from a yeast. Examples include: *Saccharomyces* sp., *Saccharomyces cerevisiae*, *Saccharomyces kluyveri*, *Saccharomyces uvarum*, *Saccharomyces validus*, *Saccharomyces fragilis*, *Saccharomyces ovisis*, *Zygosaccharomyces ashbyi*, *Schizosaccharomyces* sp., *Schizosaccharomybes japonis*, *Saccharomycodes ludwigii*, *Endomycopsis fibuliger*, *Endomycopsis chodati*, *Hansenula polymorpha*, *Pichia* sp., *Pichia stipites*, *Kluyveromyces polysporus*, *Kluyveromyces marxianus*, *Kluyveromyces* spp., *Candida* sp., *Candida utilis*, *Candidaflareri*, *Debaryomyces kloeckeri*, *Torulopsis colliculosa*, *Torulaspora rosei*, or *Yarrowia* sp., *Yarrowia lipolytica*.

In illustrative embodiments described in Example 1, the sucrose invertase is from *S. cerevisiae* (See, e.g., Romanos et al., Yeast, (1992), 8(6):423-488) and has SEQ ID NO:1. In certain embodiments, other suitable wild-type sucrose invertase sequences can be identified from National Center for Biotechnology Information ("NCBI"). BLASTP searches can be conducted against SEQ ID NO:1 using the default parameters of BLASTP. Amino acid modifications at positions 17, 28, 359 and/or 366, relative to SEQ ID NO:1, can be incorporated into any of these wild-type sucrose invertase sequences.

In various embodiments, the variant sucrose invertase (modified as described herein) can have at least 70%, 75%, 80%, 85%, 90%, 91%, 92%, 93%, 94%, 95%, 96%, 97%, or 99% amino acid sequence identity with the starting sucrose invertase (which can be a functional fragment of a longer enzyme). In various embodiments, the variant sucrose invertase (modified as described herein) can have at least 70%, 75%, 80%, 85%, 90%, 91%, 92%, 93%, 94%, 95%, 96%, 97%, or 99% amino acid sequence identity with a functional fragment of the starting sucrose invertase which does not include a predicted transit peptide sequence of amino acid residues 1-19 with reference to SEQ ID NO: 1. In various embodiments, the variant sucrose invertase (modified as described herein) can have at least 70%, 75%, 80%, 85%, 90%, 91%, 92%, 93%, 94%, 95%, 96%, 97%, or 99% amino acid sequence identity with a starting (naturally occurring or non-naturally occurring) sucrose invertase. In various embodiments, the variant sucrose invertase (modified as described herein) can have at least 70%, 75%, 80%, 85%, 90%, 91%, 92%, 93%, 94%, 95%, 96%, 97%, or 99% amino acid sequence identity with a starting (naturally occurring or non-naturally occurring) sucrose invertase from yeast. In various embodiments, the variant sucrose invertase (modified as described herein) can have at least 70%, 75%, 80%, 85%, 90%, 91%, 92%, 93%, 94%, 95%, 96%, 97%, or 99% amino acid sequence identity with a starting (naturally occurring or non-naturally occurring) sucrose invertase from the species *Saccharomyces*. In various embodiments, the variant sucrose invertase (modified as described herein) can have at least 70%, 75%, 80%, 85%, 90%, 91%, 92%, 93%, 94%, 95%, 96%, 97%, or 99% amino acid sequence identity with a starting (naturally occurring or non-naturally occurring) sucrose invertase from *Saccharomyces cerevisiae*. In various embodiments, the variant sucrose invertase (modified as described herein) can have at least 70%, 75%, 80%, 85%, 90%, 91%, 92%, 93%, 94%, 95%, 96%, 97%, or 99% amino acid sequence identity with *Saccharomyces cerevisiae* (ScSUC2) sucrose invertase, having the amino acid sequence SEQ ID NO:1. It is noted, however, that the variant sucrose invertases in accordance with the present invention exclude any of the naturally occurring sucrose invertases.

In certain embodiments, the variant sucrose invertase has an amino acid sequence of SEQ ID NO:2. In certain embodiments, the variant sucrose invertase has an amino acid sequence of SEQ ID NO:3. In certain embodiments, the variant sucrose invertase has an amino acid sequence of SEQ ID NO:4. In certain embodiments, the variant sucrose invertase has an amino acid sequence of SEQ ID NO:5. In certain embodiments, the variant sucrose invertase has an amino acid sequence of SEQ ID NO:6. In certain embodiments, the variant sucrose invertase has an amino acid sequence of SEQ ID NO:7. In certain embodiments, the variant sucrose invertase has an amino acid sequence of SEQ ID NO:8. In certain embodiments, the variant sucrose invertase has an amino acid sequence of SEQ ID NO:9. In certain embodiments, the variant sucrose invertase has an amino acid sequence of SEQ ID NO:2, 3, 4, 5, 6, 7, 8, or 9, without the transit peptide amino acid residues of position 1-19.

The modified sucrose invertase can, in various embodiments, exhibit an enhancement in ability to hydrolyze (invert) sucrose to glucose and fructose at pH 7 of at least 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 160%, 170%, 180%, 190%, or 200%, as compared to the "starting" (unmodified) sucrose invertase. This enhancement is reflected by the percentage increase in the amount of sucrose inverted by the modified sucrose invertase relative to the unmodified sucrose invertase under the same test conditions. In some embodiments, the sucrose invertase variant has this enhanced ability to hydrolyze sucrose into glucose and fructose at one or more of the following pHs: 4, 4.5, 5, 5.5, 6, 6.5, 7.5, or 8, as compared to the unmodified sucrose invertase. In certain embodiments, this enhanced ability to hydrolyze sucrose into glucose and fructose is observed at one or more temperatures between 25° C. and 35° C., inclusive (e.g., at 25° C., 26° C., 27° C., 28° C., 29° C., 30° C., 31° C., 32° C., 33° C., 34° C., and/or 35° C.).

Polynucleotides

The present disclosure also provides polynucleotides that include a nucleotide sequence encoding any of the sucrose invertase variants described herein. A nucleotide sequence encoding the sucrose invertase variants can be generated using standard molecular biology techniques well known in the art. Using the sequence information disclosed herein, a polynucleotide can be synthesized de novo using, e.g., an automatic DNA synthesizer. Alternatively, a polynucleotide encoding the sucrose invertase variants may be generated by use of site-directed mutagenesis of a wild-type nucleic acid molecule using techniques well-known in the art (e.g., PCR on a plasmid template using oligonucleotide primers). Customized nucleic acids can be ordered from various commercial sources.

In some embodiments, the polynucleotide is codon-optimized for expression in a selected host cell. The host cell can be any of those described herein (see the section entitled "Host Cells" below). Codon usage information for different host cells can be found, e.g., in the Codon Usage Database at www.kazusa.or.jp.codon/. A customized codon optimization tool and customized services are provided from various commercial sources (e.g., Integrated DNA Technologies and GeneScript). In an illustrative embodiment, the host cell is of the species Protheca, e.g., *Prototheca moriformis*, and preferred *Prototheca* codon usage is provided in Tables 2 of U.S. Pat. No. 10,316,299. In another illustrative embodiment, the host cell of the species *Chlorella*, e.g., *Chlorella* protothecoides, and preferred *Chlorella* codon usage is provided in Table 3 of U.S. Pat. No. 10,316,299. In some embodiments, at least 60%, 65%, 70%, 75%, 80%, 85%, 90%, 95%, or 100% of the codons used in the encoding polynucleotide can be the most preferred codon. In some embodiments, at least 60%, 65%, 70%, 75%, 80%, 85%, 90%, 95%, or 100% of the codons used in the encoding polynucleotide can be the first- or second-most preferred codon. It is understood that the term "preferred codon" is a codon optimized codon. The adaptiveness of a nucleotide sequence encoding a polypeptide to the codon usage of a host cell may be expressed as codon adaptation index (CAI). The codon adaptation index is herein defined as a measurement of the relative adaptiveness of the codon usage of a gene towards the codon usage of highly expressed genes in a particular host cell or organism. The relative adaptiveness (w) of each codon is the ratio of the usage of each codon, to that of the most abundant codon for the same amino acid. The CAI index is defined as the geometric mean of these relative adaptiveness values. Non-synonymous codons and termination codons (dependent on genetic code) are excluded. CAI values range from 0 to 1, with higher values indicating a higher proportion of the most abundant codons (see Sharp and Li, 1987, Nucleic Acids Research 15: 1281-1295; also see: Jansen et al., 2003, Nucleic Acids Res. 31(8):2242-51). An adapted nucleotide sequence preferably has a CAI of at least 0.2, 0.3, 0.4, 0.5, 0.6, 0.7, 0.8 or 0.9. Codon optimization methods for optimum gene expression in heterologous organisms are known in the art and have been previously described (see e.g., Welch et al., 2009, PLoS One 4:e7002; Gustafsson et al., 2004, Trends Biotechnol. 22:346-353; Wu et al., 2007, Nucl. Acids Res. 35:D76-79; Villalobos et al., 2006, BMC Bioinformatics 7:285; U.S. Patent Publication 2011/0111413; and U.S. Patent Publication 2008/0292918).

In various illustrative embodiments, the polynucleotides include a nucleotide sequence that has at least 60%, 65%, 70%, 75%, 80%, 85%, 90%, 91%, 92%, 93%, 94%, 95%, 96%, 97%, or 99% nucleotide sequence identity with the *Saccharomyces cerevisiae* (ScSUC2) sucrose invertase sequence of SEQ ID NO:11, SEQ ID NO:12, SEQ ID NO:13, SEQ ID NO:14, SEQ ID NO:15, SEQ ID NO:17, SEQ ID NO:18, or a functional subsequence thereof, and encodes a sucrose invertase variant described herein. In various illustrative embodiments, the polynucleotide comprise the sequence of SEQ ID NO:12, SEQ ID NO:13, SEQ ID NO:14, SEQ ID NO:15, or SEQ ID NO:17.

Expression of Sucrose Invertase Variants

Host cells can be engineered to express sucrose invertase variants using conventional techniques of molecular biology (including recombinant techniques), microbiology, cell biology, and biochemistry, which are within the skill of the art. Such techniques are explained fully in the literature, see e.g., "Molecular Cloning: A Laboratory Manual," fourth edition (Sambrook et al., 2012); "Oligonucleotide Synthesis" (M. J. Gait, ed., 1984); "Culture of Animal Cells: A Manual of Basic Technique and Specialized Applications" (R. I. Freshney, ed., 6th Edition, 2010); "Methods in Enzymology" (Academic Press, Inc.); "Current Protocols in Molecular Biology" (F. M. Ausubel et al., eds., 1987, and periodic updates); "PCR: The Polymerase Chain Reaction," (Mullis et al., eds., 1994); Singleton et al., Dictionary of Microbiology and Molecular Biology 2nd ed., J. Wiley & Sons (New York, N.Y. 1994). Methods, reagents and tools for transforming yeast are described in "Guide to Yeast Genetics and Molecular Biology," C. Guthrie and G. Fink, Eds., Methods in Enzymology 350 (Academic Press, San Diego 2002). Methods, reagents and tools for transforming *Y. lipolytica* are found in "*Yarrowia lipolytica*," C. Madzak J. M. Nicaud and C. Gaillardin in "Production of Recombinant Proteins Novel Microbial and Eucaryotic Expression Systems," G. Gellissen, Ed. 2005. Methods, reagents and tools for engineering cyanobacteria may be found in T. Thiel (1994), Genetic analysis of cyanobacteria, Kluwer Academic publishers 581-611. Other publications describing gene expression in algae and fungi include, e.g., Saunders & Warmbrodt, "Gene Expression in Algae and Fungi, Including Yeast," (1993), National Agricultural Library, Beltsville, Md.; WO2011/150410; and WO2011/150411, which are incorporated herein by reference in their entirety.

Vectors are polynucleotide vehicles used to introduce genetic material into a cell. Vectors useful in the methods described herein can be linear or circular. Vectors can integrate into a target genome of a host cell or replicate independently in a host cell. For many applications, integrating vectors that produced stable transformants are preferred. Vectors can include, for example, an origin of replication, a multiple cloning site (MCS), and/or a selectable marker. An expression vector typically includes an expression cassette containing regulatory elements that facilitate expression of a polynucleotide sequence (often a coding sequence) in a particular host cell. Vectors include, but are not limited to, integrating vectors, prokaryotic plasmids, episomes, viral vectors, cosmids, and artificial chromosomes.

Illustrative regulatory elements that may be used in expression cassettes include promoters, enhancers, internal ribosomal entry sites (IRES), and other expression control elements (e.g., transcription termination signals, such as polyadenylation signals and poly-U sequences). Such regulatory elements are described, for example, in Goeddel, Gene Expression Technology: Methods In Enzymology 185, Academic Press, San Diego, Calif. (1990).

In some embodiments, vectors may be used to introduce systems that can carry out genome editing, such as CRISPR systems. See U.S. Patent Pub. No. 2014/0068797, published 6 Mar. 2014; see also Jinek M., et al., "A programmable dual-RNA-guided DNA endonuclease in adaptive bacterial immunity," Science 337:816-21, 2012). In Type II CRISPR-Cas9 systems, Cas9 is a site-directed endonuclease, namely an enzyme that is, or can be, directed to cleave a polynucleotide at a particular target sequence using two distinct endonuclease domains (HNH and RuvC/RNase H-like domains). Cas9 can be engineered to cleave DNA at any desired site because Cas9 is directed to its cleavage site by RNA. Cas9 is therefore also described as an "RNA-guided nuclease." More specifically, Cas9 becomes associated with one or more RNA molecules, which guide Cas9 to a specific polynucleotide target based on hybridization of at least a portion of the RNA molecule(s) to a specific sequence in the target polynucleotide. Ran, F. A., et al., ("In vivo genome editing using *Staphylococcus aureus* Cas9," Nature 520 (7546):186-91, 2015 Apr. 9], including all extended data) present the crRNA/tracrRNA sequences and secondary structures of eight Type II CRISPR-Cas9 systems. Cas9-like synthetic proteins are also known in the art (see U.S. Published Patent Application No. 2014-0315985, published 23 Oct. 2014).

Vectors or other polynucleotides can be introduced into host cells by any of a variety of standard methods, such as transformation, conjugation, electroporation, nuclear microinjection, transduction, transfection (e.g., lipofection mediated or DEAE-Dextrin mediated transfection or transfection using a recombinant phage virus), incubation with calcium phosphate DNA precipitate, high velocity bombardment with DNA-coated microprojectiles, and protoplast fusion. Transformants can be selected by any method known in the art. Suitable methods for selecting transformants are described in the publications cited above.

In some embodiments, a construct for expressing a sucrose invertase variant is introduced, e.g., using any of a variety of available techniques, into a host cell to produce an "engineered cell." In particular embodiments, the engineered cell is capable of expressing the sucrose invertase variant (e.g., under appropriate culture conditions). Where the host cell is a microbe, the engineered cell is an engineered microbial cell. Wherein the host cell is a yeast cell, the engineered cell is an engineered yeast cell. Where the host cell is an algal cell, the engineered cell is an engineered algal cell. In certain embodiments, the engineered algal cell is an engineered *Prototheca* cell, e.g., an engineered *Prototheca moriformis* cell, as illustrated in Example 1. A wide variety of host cells are available for expressing enzymes such as the sucrose invertase variants, and examples are described below in the section entitled "Host Cells."

Engineered cells that express sucrose invertase variants such as those described herein can have, in various embodiments, an enhanced ability to hydrolyze (invert) sucrose into glucose and fructose at pH 7 of at least 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 160%, 170%, 180%, 190% or 200%, as compared to a cell of the same type that has been engineered to express a sucrose invertase lacking any of the amino acid substitutions described herein that confer an enhanced ability to hydrolyze sucrose into glucose and fructose at pH 7 (e.g., an unmodified form of the same sucrose invertase). In various embodiments, the enhanced ability to hydrolyze sucrose into glucose and fructose is also observed at one or more of the following pHs: 4, 4.5, 5, 5.5, 6, 6.5, 7.5, or 8, as compared to the unmodified sucrose invertase. In certain embodiments, this enhanced ability to hydrolyze sucrose into glucose and fructose is observed at one or more temperatures between 25° C. and 35° C., inclusive (e.g., at 25° C., 26° C., 27° C., 28° C., 29° C., 30° C., 31° C., 32° C., 33° C., 34° C., and/or 35° C.).

For example, one or more polynucleotides ("genes") encoding one or more of the aforementioned sucrose invertase variants can be used in any of a variety of genetic constructs including plasmids or other vectors for expression or recombination in a host cell. As noted above, the gene(s) can be codon optimized for expression in a target host cell. The gene(s) can be included in one or more expression cassette(s) that include a promoter (e.g., a heterologous promoter) and downstream regulatory element. The vector can include flanking sequences for homologous recombination. For example, the vector can cause insertion into a chromosome of the host cell, where it can be stably expressed. The proteins produced by the genes can be used in vivo (e.g., in a cell), in culture (e.g., if the protein is secreted into the culture medium), or in purified form. In an embodiment, an expression cassette comprises a homologous promoter, a CDS operable to express one or more sucrose invertase variants and a 3'UTR. The 3'UTR can comprise a polyadenylation site.

Secretion of a sucrose invertase (such as a sucrose invertase variant described above) can obviate the need for expression of a transporter that can transport sucrose into the cell. This is because a secreted invertase catalyzes the conversion of a molecule of sucrose into a molecule of glucose and a molecule of fructose, both of which can be transported and utilized by host cells described herein. For example, expression of a sucrose invertase with a secretion signal generates invertase activity outside the cell. See Hawkins et al., Current Microbiology Vol. 38 (1999), pp. 335-341 for examples of secretion signals active in *Chlorella* and/or *Prototheca*. Expression of such a protein, as enabled by the genetic engineering methodology disclosed herein, allows cells already capable of utilizing extracellular glucose as an energy source to utilize sucrose as an extracellular energy source. Alternatively, a sucrose invertase can also be expressed intracellularly in cells that express a sucrose transporter, as well as in cells that express any carbohydrate transporter that allows sucrose to enter the cell. Exemplary sucrose transporters include sequences described in Genbank accession numbers CAD91334, CAB92307, and CAA53390.

Co-Expression with Other Heterologous Molecules

In some embodiments, the sucrose invertase is expressed in the cell to efficiently utilize sucrose as a carbon source during fermentation to produce a product of interest (e.g., lipids). In certain embodiments, the sucrose invertase variant is co-expressed with one or more heterologous molecules, which are end products of interest. For example, the heterologous molecules can be an antibody, a fusion protein, or an enzyme, which are expressed and subsequently purified from the cells or supernatant. In certain embodiments, co-expressed heterologous molecules are intermediaries to produce other end products of interest. For example, heterologous molecules are enzymes in a biosynthetic pathway, to produce secondary metabolites as end products of interest. Such exemplary end products of interest include, but not limited to, a fatty acid, a lipid, a sterol, an enzyme, a fusion protein, an amino acid, an antioxidant, an antibody, or a pharmaceutical product.

In some embodiments, the heterologous molecules co-expressed with the sucrose invertase variant are enzymes of a lipid biosynthetic pathway, and the end products of interest are lipids. For example, the sucrose invertase variant is co-expressed with one or more heterologous or exogenous lipid biosynthesis enzymes selected from the group consisting of a fatty acyl thioesterase A (FATA), a fatty acyl thioesterase B (FATB), a fatty acyl desaturase (FAD), including without limitation phosphatidylglycerol desaturase (FAD4), plastidial oleate desaturase (FADE), plastidial linoleate desaturase (FAD7/FAD8), endoplasmic reticulum oleate desaturase (FAD2), endoplasmic reticulum linolate desaturase (FAD3), delta 12 fatty acid desaturase (Δ12 FAD), delta 15 fatty acid desaturase (Δ15 FAD), and stearoyl-ACP desaturase 2 (SAD2); a 1-acylglycerol-3-phosphate O-acyltransferase (LPAAT), a glycerol-3-phosphate acyltransferase (GPAT), an acyl CoA:diacylglycerol acyltransferase (DGAT), a fatty acid and a fatty acid elongase (FAE), and a long-chain acyl-CoA synthetase (LACS).

In some embodiments, the sucrose invertase variant is co-expressed with one or more exogenous or heterologous enzymes, such as an alpha galactosidase or a 4-amino-5-hydroxymethyl-2-methylpyrimidine phosphate synthase (THIC). Recombinant expression of heterologous or exogenous lipid biosynthesis enzymes is described, e.g., in U.S. Patent Publ. No. 2014/0178950, which is incorporated herein by reference in its entirety for all purposes.

In some embodiments, one or more lipid biosynthesis enzymes endogenous to the host cell selected from the group consisting of a fatty acyl thioesterase A (FATA), a fatty acyl thioesterase B (FATB), a fatty acyl desaturase (FAD), including without limitation phosphatidylglycerol desaturase (FAD4), plastidial oleate desaturase (FAD6), plastidial linoleate desaturase (FAD7/FAD8), endoplasmic reticulum oleate desaturase (FAD2), endoplasmic reticulum linolate desaturase (FAD3), delta 12 fatty acid desaturase (Δ12 FAD), delta 15 fatty acid desaturase (Δ15 FAD), and stearoyl-ACP desaturase 2 (SAD2); a 1-acylglycerol-3-phosphate O-acyltransferase (LPAAT), a glycerol-3-phosphate acyltransferase (GPAT), an acyl CoA:diacylglycerol acyltransferase (DGAT), a fatty acid elongase (FAE) and a long-chain acyl-CoA synthetase (LACS) are deleted, knocked out or knocked down. For example, one or more polynucleotides encoding one or more of the aforementioned enzymes can also be used to prepare antisense, or inhibitory RNA (e.g., RNAi or hairpin RNA) to inhibit complementary genes in the host cell. For example, armed with the knowledge of a gene sequence encoding one of the aforementioned proteins, one can engineer a host cell with the same or similar gene to express an RNAi construct, gene knockout, knockdown, point mutation, or the like, and thereby reduce the expression and/or activity of one or more of the enzymes in the host cell. As a result, the host cell (e.g., microalgal cell) can produce an oil with an altered fatty acid profile in which the mean chain length is decreased or increased, depending on the presence of other lipid biosynthesis genes. In some embodiments, a mutation (including knockout) or inhibition (e.g., using antisense or RNAi) of one or more endogenous desaturase genes (e.g., a stearoyl-ACP desaturase or fatty acid desaturase including a delta 12 fatty acid desaturase) can reduce or eliminate desaturase activity to produce a more fully saturated triglyceride profile.

When engineering cells for lipid production, depending on the desired properties of the lipid molecule to be produced, one or more genes encoding enzymes that utilize fatty acids or fatty acyl molecules as substrates to produce lipid molecules may be attenuated or over-expressed in the host cell (e.g., microalga), for example using RNAi, hairpin constructs, knockdowns, double or single knockouts or replacements (e.g., replacing an endogenous gene with a heterologous gene), and/or promoter swap (e.g., replacing an endogenous promoter with a heterologous promoter).

Exemplary lipids which may be produced as end products of interest from microalgal cells include high oleic oil with a fatty acid profile of greater than 75% oleic acid, triglycerides enriched with mid-chain fatty acids (e.g., C8, C10, or C12 fatty acids), SOS, POP, or POS, wherein 'P' represents palmitic acid, 'S' represents stearic acid, and 'O' represents oleic acid. Methods for production of various triglycerides in microalgal cells are described in, for example, U.S. Pat. Nos. 8,476,059, 7,883,882, 8,592,188, 10,287,613, 10,053,715, 10,125,382 which are incorporated herein by reference in their entirety.

Host Cells

Any species of organism that can be engineered to express a sucrose invertase can be used as the host cell. A wide variety of microbial host cells are used in the fermentative production of chemicals and biologics.

Bacteria cells, including gram-positive or gram-negative bacteria can be engineered as described above. Examples include *Bacillus subtilis*, *B. licheniformis*, *B. lentus*, *B. brevis*, *B. stearothermophilus*, *B. alkalophilus*, *B. amyloliquefaciens*, *B. clausii*, *B. halodurans*, *B. megaterium*, *B. coagulans*, *B. circulans*, *B. lautus*, *B. thuringiensis*, *Corynebacteria glutamicum* cells, *S. albus*, *S. lividans*, *S. coelicolor*, *S. griseus*, *Pseudomonas* sp., *P. alcaligenes*, *P. citrea*, *Lactobacillus* spp. (such as *L. lactis*, *L. plantarum*), *L. grayi*, *E. coli*, *E. faecium*, *E. gallinarum*, E. casseliflavus, and/or *E. faecalis* cells.

In some embodiments, the microbial host cells used in the methods described herein are filamentous fungal cells. (See, e.g., Berka & Barnett, Biotechnology Advances, (1989), 7(2):127-154). Examples include *Trichoderma longibrachiatum*, *T. viride*, *T. koningii*, *T. harzianum*, *Penicillium* sp., *Humicola insolens*, *H. lanuginose*, *H. grisea*, *Chrysosporium* sp., *C. lucknowense*, *Gliocladium* sp., *Aspergillus* sp. (such as *A. oryzae*, *A. niger*, *A. sojae*, *A. japonicus*, *A. nidulans*, or *A. awamori*), *Fusarium* sp. (such as *F. roseum*, *F. graminum F. cerealis*, *F. oxysporuim*, or *F. venenatum*), *Neurospora* sp. (such as *N. crassa* or *Hypocrea* sp.), *Mucor* sp. (such as *M. miehei*), *Rhizopus* sp., and *Emericella* sp. cells. In particular embodiments, the fungal cell engineered as described above is *A. nidulans*, *A. awamori*, *A. oryzae*, *A. aculeatus*, *A. niger*, *A. japonicus*, *T. reesei*, *T. viride*, *F. oxysporum*, or *F. solani*. Illustrative plasmids or plasmid components for use with such hosts include those described in U.S. Patent Pub. No. 2011/0045563.

Yeasts can also be used as the microbial host cell in the methods described herein. Examples include: *Saccharomyces* sp., *Saccharomyces cerevisiae*, *Saccharomyces kluyveri*, *Saccharomyces uvarum*, *Saccharomyces validus*, *Saccharomyces fragilis*, *Saccharomyces ovisis*, *Zygosaccharomyces ashbyi*, *Schizosaccharomyces* sp., *Schizosaccharomybes japonis*, *Saccharomycodes ludwigii*, *Endomycopsis fibuliger*, *Endomycopsis chodati*, *Hansenula polymorpha*, *Pichia* sp., *Pichia stipites*, *Kluyveromyces polysporus*, *Kluyveromyces marxianus*, *Kluyveromyces* spp., *Candida* sp., *Candida utilis*, *Candida flareri*, *Debaryomyces kloeckeri*, *Torulopsis colliculosa*, and *Torulaspora rosei*.

In other embodiments, the host cell is a cyanobacterium, such as cyanobacterium classified into any of the following groups based on morphology: Chlorococcales, Pleurocapsales, Oscillatoriales, Nostocales, Synechosystic or Stigonematales (See, e.g., Lindberg et al., Metab. Eng., (2010) 12(1):70-79). Illustrative plasmids or plasmid components for use in cyanobacterial cells include those described in U.S. Patent Pub. Nos. 2010/0297749 and 2009/0282545 and in Intl. Pat. Pub. No. WO 2011/034863.

In some embodiments, the host cell can be an algal cell derived, e.g., from a green alga, red alga, a glaucophyte, a chlorarachniophyte, a euglenid, a chromista, or a dinoflagellate.

In some embodiments, the host cell is a microalga. Non-limiting examples of microalgae that can be used for expression of sucrose invertase variants include, e.g., *Achnanthes orientalis*, *Agmenellum*, *Amphiprora hyaline*, *Amphora coffeiformis*, *Amphora coffeiformis linea*, *Amphora coffeiformis punctata*, *Amphora coffeiformis taylori*, *Amphora coffeiformis tenuis*, *Amphora delicatissima*, *Amphora delicatissima capitata*, *Amphora* sp., *Anabaena*,

*Ankistrodesmus, Ankistrodesmus falcatus, Boekelovia hooglandii, Borodinella* sp., *Botryococcus braunii, Botryococcus sudeticus, Bracteococcus minor, Bracteococcus medionucleatus, Carteria, Chaetoceros gracilis, Chaetoceros muelleri, Chaetoceros muelleri subsalsum, Chaetoceros* sp., *Chlorella anitrata, Chlorella Antarctica, Chlorella aureoviridis, Chlorella candida, Chlorella capsulate, Chlorella desiccate, Chlorella ellipsoidea, Chlorella emersonii, Chlorella fusca, Chlorella fusca* var. *vacuolata, Chlorella glucotropha, Chlorella infusionum, Chlorella infusionum* var. *actophila, Chlorella infusionum* var. *auxenophila, Chlorella kessleri, Chlorella lobophora* (strain SAG 37.88), *Chlorella luteoviridis, Chlorella luteoviridis* var. *aureoviridis, Chlorella luteoviridis* var. *lutescens, Chlorella miniata, Chlorella minutissima, Chlorella mutabilis, Chlorella nocturna, Chlorella ovalis, Chlorella parva, Chlorella photophila, Chlorella pringsheimii, Chlorella* protothecoides (including any of UTEX strains 1806, 411, 264, 256, 255, 250, 249, 31, 29, 25), *Chlorella protothecoides* var. *acidicola, Chlorella regularis, Chlorella regularis* var. *minima, Chlorella regularis* var. *umbricata, Chlorella reisiglii, Chlorella saccharophila, Chlorella saccharophila* var. *ellipsoidea, Chlorella salina, Chlorella simplex, Chlorella sorokiniana, Chlorella* sp., *Chlorella sphaerica, Chlorella stigmatophora, Chlorella vanniellii, Chlorella vulgaris, Chlorella vulgaris f tertia, Chlorella vulgaris* var. *autotrophica, Chlorella vulgaris* var. *viridis, Chlorella vulgaris* var. *vulgaris, Chlorella vulgaris* var. *vulgaris* f. *tertia, Chlorella vulgaris* var. *vulgaris* f. *viridis, Chlorella xanthella, Chlorella zofingiensis, Chlorella trebouxioides, Chlorella vulgaris, Chlorococcum infusionum, Chlorococcum* sp., *Chlorogonium, Chroomonas* sp., *Chrysosphaera* sp., *Cricosphaera* sp., *Crypthecodinium cohnii, Cryptomonas* sp., *Cyclotella cryptica, Cyclotella meneghiniana, Cyclotella* sp., *Dunaliella* sp., *Dunaliella bardawil, Dunaliella bioculata, Dunaliella granulate, Dunaliella maritime, Dunaliella minuta, Dunaliella parva, Dunaliella peircei, Dunaliella primolecta, Dunaliella salina, Dunaliella terricola, Dunaliella tertiolecta, Dunaliella viridis, Dunaliella tertiolecta, Eremosphaera viridis, Eremosphaera* sp., *Ellipsoidon* sp., *Euglena, Franceia* sp., *Fragilaria crotonensis, Fragilaria* sp., *Gleocapsa* sp., *Gloeothamnion* sp., *Hymenomonas* sp., *Isochrysis* aff. *galbana, Isochrysis galbana, Lepocinclis, Micractinium, Micractinium* (UTEX LB 2614), *Monoraphidium minutum, Monoraphidium* sp., *Nannochloris* sp., *Nannochloropsis salina, Nannochloropsis* sp., *Navicula acceptata, Navicula biskanterae, Navicula pseudotenelloides, Navicula pelliculosa, Navicula saprophila, Navicula* sp., *Nephrochloris* sp., *Nephroselmis* sp., *Nitschia communis, Nitzschia alexandrina, Nitzschia communis, Nitzschia dissipata, Nitzschia frustulum, Nitzschia hantzschiana, Nitzschia inconspicua, Nitzschia intermedia, Nitzschia microcephala, Nitzschia pusilla, Nitzschia pusilla elliptica, Nitzschia pusilla monoensis, Nitzschia quadrangular, Nitzschia* sp., *Ochromonas* sp., *Oocystis parva, Oocystis pusilla, Oocystis* sp., *Oscillatoria limnetica, Oscillatoria* sp., *Oscillatoria subbrevis, ParaChlorella kessleri, Pascheria acidophila, Pavlova* sp., *Phagus, Phormidium, Platymonas* sp., *Pleurochrysis carterae, Pleurochrysis dentate, Pleurochrysis* sp., *Prototheca wickerhamii, Prototheca stagnora, Prototheca portoricensis, Prototheca moriformis, Prototheca zopfli, PseudoChlorella aquatica, Pyramimonas* sp., *Pyrobotrys, Rhodococcus opacus, Sarcinoid chrysophyte, Scenedesmus armatus, Schizochytrium, Spirogyra, Spirulina platensis, Stichococcus* sp., *Synechococcus* sp., *Tetraedron, Tetraselmis* sp., *Tetraselmis suecica, Thalassiosira weissflogii,* and *Viridiella fridericiana.*

In some embodiments, the host cell is a plastidic cell, e.g., a heterotrophic microalga of the phylum Chlorpophya, the class Trebouxiophytae, the order Chlorellales, or the family Chlorellacae. In some embodiments, the cell is oleaginous and capable of accumulating at least 40% oil by dry cell weight. The cell can be an obligate heterotroph, such as a species of *Prototheca*, including *Prototheca moriformis* or *Prototheca zopfli*. In some embodiments, the host cell is a marine protist of the class Labyrinthulomycetes, the family Thraustochytriaceae, or a genus selected from the group consisting of: Althomia; *Aplanochytrium*; Elnia; *Japonochytrium; Schizochytrium; Thraustochytrium; Aurantiochytrium; Oblongichytrium;* and *Ulkenia*. The nucleic acid encoding the sucrose invertase variants described herein can also be expressed in autotrophic algae or plants.

Cell Culture

The engineered cells described herein can be cultured in a suitable culture medium to optimize expression of the sucrose invertase variant and/or end products of interest. Cell culture media are well known and include, but not limited to, a minimal medium, i.e., one containing the minimum nutrients possible for cell growth. Minimal medium typically contains: (1) a carbon source for microbial growth; (2) salts, which may depend on the particular microbial cell and growing conditions; and (3) water. Suitable media can also include any combination of the following: a nitrogen source for growth and product formation, a sulfur source for growth, a phosphate source for growth, metal salts for growth, vitamins for growth, and other cofactors for growth. Minimal medium can be further supplemented with one or more selective agents (e.g., antibiotics). For certain engineered host cells, complex media (e.g., yeast extract-peptone-dextrose broth) can be used. In general, culture media conditions are optimized by selecting suitable type and amount of carbon source, the type and amount of nitrogen source, the carbon-to-nitrogen ratio, the amount of different minerals, vitamins, the dissolved oxygen level, temperature, pH, duration of different phases (biomass growth and production phase), and other conditions.

The term "carbon source" refers to one or more carbon-containing compounds capable of being metabolized by a cultured cell. Typically, the carbon source is a carbohydrate (such as a monosaccharide, a disaccharide, an oligosaccharide, or a polysaccharide), or an invert sugar (e.g., enzymatically treated sucrose syrup). Illustrative monosaccharides include glucose (dextrose), fructose (levulose), and galactose; illustrative oligosaccharides include dextran or glucan, and illustrative polysaccharides include starch and cellulose. Suitable sugars include C6 sugars (e.g., fructose, mannose, galactose, or glucose) and C5 sugars (e.g., xylose or arabinose). Other, less expensive carbon sources include sugar cane juice, beet juice, sorghum juice, and the like, any of which may, but need not be, fully or partially deionized. Because the engineered cells described herein are able to use sucrose, in certain embodiments, the culture medium includes sucrose (or sources of sucrose such as sugar cane or sugar beets) as a carbon source. In certain embodiments, the culture medium comprises sucrose in a mixture with other carbon sources.

In various embodiments, the culturing is carried out at a pH of about 4, 4.5, 5, 5.5, 6, 6.5, 7, 7.5, or 8. In certain embodiments culturing is carried out at pH 7 if production of end products of interest by the engineered cells is optimal at pH 7. The present sucrose invertase variants are particularly useful at pH 7 as the wild-type sucrose invertase activity is optimal at a lower pH.

Generally, the temperature during culturing is maintained between about 4° C. and about 60° C., typically between about 10° C. and 50° C., more typically between about 20° C. and 40° C. Any suitable fermentation temperature can be used in the methods described herein to optimize production of end products of interest.

The duration of culturing or fermentation to obtain an end product of interest depends on the nature of the end product. In certain embodiments, engineered cells are cultured for a period of about 6 hours to 300 hours, or for at least 12, 24, 36, 48, 60, 72, 84 hours or more. Any suitable fermentation period can be used to optimize production of end products of interest.

Standard culture conditions and modes of fermentation, such as batch, fed-batch, or continuous fermentation that can be used. These fermentation processes are common and well known in the art, and examples can be found in Brock, Biotechnology: A Textbook of Industrial Microbiology, Second Edition (1989) Sinauer Associates, Inc.; Manual of Industrial Microbiology and Biotechnology. A. Demain and J. Davies Eds. ASM Press (1999). In certain embodiments, solid-state fermentation processes can be applied where sucrose or a sucrose containing material is used as a carbon source during fermentation.

Engineered cells can be cultured both for purposes of conducting genetic manipulations and for subsequent production of end product of interest. The former type of culture is conducted on a small scale and initially, at least, under conditions in which the starting microorganism can grow. Culture for commercial production of end product of interest is usually conducted on a large scale. The cultivation is performed using a suitable nutrient medium typically comprising sucrose (or a sucrose containing material) and optionally other carbon source and further comprising nitrogen sources and inorganic salts, using procedures known in the art. Suitable media are available from commercial suppliers or may be prepared according to published compositions, for example, in catalogues of the American Type Culture Collection, Atlas and Parks (eds.) The Handbook of Microbiological Media (1993) CRC Press, Boca Raton, Fla., which are incorporated herein by reference.

For microalgal cells, suitable instructions for the preparation of particular media that are suitable for a wide variety of strains of microorganisms can be found, for example, online at utex.org/, a site maintained by the University of Texas at Austin for its culture collection of algae (UTEX). For example, various fresh water and salt water media are provided in U.S. Patent Publ. No. 2012/0288930, hereby incorporated herein by reference in its entirety for its description of these media. Other suitable media for use with the methods described herein can be readily identified by consulting the URL identified above, or by consulting other organizations that maintain cultures of microorganisms, such as SAG, CCAP, or CCALA. SAG refers to the Culture Collection of Algae at the University of Gottingen (Gottingen, Germany), CCAP refers to the culture collection of algae and protozoa managed by the Scottish Association for Marine Science (Scotland, United Kingdom), and CCALA refers to the culture collection of algal laboratory at the Institute of Botany (ccala.butbn.cas.cz/, Czech Republic).

Microalgal cultures can be contained within a bioreactor. Optionally, the bioreactor does not allow light to enter. Alternatively, microalgae can also be cultured in photobioreactors that contain a fixed carbon source and allow light to strike the cells. Exposure of microalgae cells to light, even in the presence of a fixed carbon source that the cells transport and utilize (i.e., mixotrophic growth), can accelerate growth compared to culturing cells in the dark. Culture condition parameters can be manipulated to increase or improve total production of end product of interest. In some instances, it is preferable to culture cells in the dark, such as, for example, when using extremely large (e.g., 10,000 L, 40,000 L, 100,000 L, 500,000 L, or larger, bioreactors) fermenters that do not allow light to strike the culture. Standard methods for the growth and propagation of various microalgal cells are known. For example, the methods and tools for *Chlorella* and/or *Prototheca* are known and described in, e.g., Miao and Wu, J. Biotechnology, 2004, 11:85-93 and Miao and Wu, Biosource Technology (2006) 97:841-846.

Recovery of Sucrose Invertase Variants/Products of Interest from Cell Cultures

Any of the cell culture methods described herein may further include a step of recovering any sucrose invertase variants produced by an engineered cell described herein. In some embodiments, where a sucrose invertase variant is produced intracellularly and not secreted, cells are recovered and a cell lysate is produced that contains the variant. In some embodiments, where a sucrose invertase variant is secreted, the variant is recovered from the culture medium. In any case, a so-called harvest stream can be recovered/harvested from the production vessel. The harvest stream may include, for instance, cell-containing or cell-free aqueous solution coming from the production vessel. Cells present in the harvest stream can be separated from the culture medium by any operations known in the art, such as for instance filtration, centrifugation, decantation, membrane crossflow ultrafiltration or microfiltration, tangential flow ultrafiltration or microfiltration or dead-end filtration.

Further steps of separation and/or purification of the produced sucrose invertase variant from other components, i.e., so-called downstream processing steps can optionally be carried out. These steps may include any means known to a skilled person, such as, for instance, concentration, extraction, crystallization, precipitation, adsorption, ion exchange, chromatography and/or distillation. These procedures can be used alone or in combination to purify a sucrose invertase variant. Further purification steps can include one or more of, e.g., concentration, crystallization, precipitation, washing and drying, treatment with activated carbon, ion exchange and/or re-crystallization. The design of a suitable purification protocol may depend on the cells, the culture medium, the size of the culture, the production vessel, etc., and is within the level of skill in the art.

While the above described techniques are described in the context of sucrose invertase variants, they can be also applied to the recovery of any end products of interest.

Methods of Using Sucrose Invertase Variants

Sucrose invertase variants can be used to hydrolyze any suitable substrate by contacting it with enzyme under suitable conditions for hydrolysis to occur. This contact can occur intracellularly, in a culture medium, or in an in vitro reaction mixture. In some embodiments, the substrate is sucrose, and one or more sucrose invertase variants are used to produce glucose and fructose.

For a wild-type enzyme, the temperature at which the rate of reaction is at its greatest is reportedly 60° C., at an optimum pH of 4.5 (Schiweck, Hubert; Clarke, Margaret; Pollach, Gunter (2007) "Sugar," Ullmann's Encyclopedia of Industrial Chemistry, Weinheim: Wiley-VCH). Such conditions can be used for an in vitro reaction, but when the sucrose invertase variant is contacted with a substrate in a living cell or growing cell culture, the need for cell viability may dictate different conditions, which can be determined by those skill in the art. Illustrative suitable conditions in such embodiments include, but are not limited to, a temperature range of about 25° C. to 35° C., and a pH of about 4, 4.5, 5, 5.5, 6, 6.5, 7.0, 7.5, or 8.

EXAMPLE

The following example is offered to illustrate, but not to limit the claimed invention.

Example 1—Sucrose Invertase Variants with Enhanced Activity at pH 7

To minimize or eliminate the need for exogenous invertase addition during fermentation of microorganisms (e.g., Prototheca moriformis), directed evolution was employed to generate sucrose invertase variants that are more active at pH 7 and can allow us to widen the operating pH range of fermentation of microorganisms without compromising performance.

Materials and Methods

Construction and Transformation of the Saturation Mutagenesis Library

In this study, NDC/VHG saturation mutagenesis was performed on codons 2-385 of the wild-type ScSUC2 gene (SEQ ID NO:11) using a Phusion site-directed mutagenesis protocol familiar to those skilled in the art. This method utilizes PCR with degenerate oligonucleotides to replace each codon of interest with one of 21 different codons that together code for 19 different amino acids. A pUC19-based plasmid harboring the wild-type ScSUC2 gene (construct pSZ6657; SEQ ID NO:11) was used as the PCR template.

PCR oligonucleotides were designed to anneal to the template in an adjacent, back-to-back orientation such that the resulting PCR product comprised the entire template sequence in linear form. For each amino-acid position, two mutagenic forward oligonucleotides were designed such that a degenerate codon (NDC or VHG) at the extreme 5' end would overlap with the wild-type codon to be mutagenized. The reverse oligonucleotide was not mutagenic. All of the oligonucleotides were phosphorylated prior to initiating the mutagenic PCR reaction.

For convenience, four saturation mutagenesis libraries (amino acids 2-97, 98-193, 194-289, and 290-385) were synthesized to cover the N-terminus of the expressed ScSUC2 gene (SEQ ID NO:11). Each of these libraries could contain up to 2016 variants, with each variant expecting to harbor a single amino acid substitution. To generate each library, mutagenic PCR reactions were performed in parallel in a 96-well format. Equal volumes of the resulting PCR products were then pooled and subjected to gel purification. The isolated fragment was subsequently circularized using T4 ligase, and the ligation reaction was transformed into electrocompetent *Escherichia co/i* cells, with transformants growing on LB agar containing 100 mg/L ampicillin for selection.

For each library, quality control was performed on 20 randomly selected *E. coli* transformants via colony PCR and Sanger sequencing, techniques that are familiar to those skilled in the art, to confirm the mutagenized sequences exhibited high mutational diversity but with minimal frame-shift mutations. Plasmid DNA was then prepared from an E. co/i culture that was inoculated with a sufficiently large number of transformants (approx. 50,000) to ensure adequate coverage of all possible variants in the library. The transformants were grown in LB medium with 200 mg/L ampicillin for selection. This DNA was digested with the PmeI restriction enzyme to yield a ~3.9-kb fragment of interest for transformation into the *P. moriformis* base strain, S7485, via a suitable technique (as described in U.S. Pat. Nos. 8,846,352; 9,328,351 and 9,649,368). This fragment includes: 1) the 5' and 3' homology arms for targeted integration into the DAO1b locus of *P. moriformis* and 2) the CrTUB2 promoter and PmPGH 3'-UTR for expression of the ScSUC2 wild-type and variant genes, which endows *P. moriformis* transformants with the ability to grow on agar plates with medium (as detailed in U.S. Pat. Nos. 8,846,352; 9,328,351 and 9,649,368 and published PCT Patent Application WO2018/067849) containing 20 g/L sucrose as the sole carbon source.

Library Screening, Evaluation of Sucrose Invertase Activity, and Identification of Mutations of Interest For each library, approximately 1000-1500 *P. moriformis* transformants were selected and cultured individually in growth medium at pH 7 and 28° C. until they reached mid-log phase. They were then pooled and plated for clonal isolation. Approximately 1,500 of the isolated clones were evaluated for their sucrose hydrolytic activity at pH 7 and 28° C. First, they were cultured in nitrogen-replete EB03 growth medium (as detailed in published PCT Patent Application WO2018/067849) with glucose as the sole carbon source for 72 h (until the glucose was completely depleted). Then they were used to inoculate nitrogen-replete H29 growth medium (as detailed in published PCT Patent Application WO2018/067849) with 55 g/L sucrose as the sole carbon source. The resulting sucrose-based cultures were grown for 20-24 h, after which the residual sucrose concentration (g/L) of each culture was measured using an enzymatic colorimetric assay or a YSI biochemistry analyzer (YSI Inc.). Similar procedures were followed to assess the sucrose hydrolytic activities of the isolated clones at pH 5 and/or 32° C. In those cases, the inoculum size used and the fermentation time of the sucrose-based cultures were adjusted, as necessary, to ensure the sucrose in these cultures was not completely depleted.

To perform the colorimetric assay, each sucrose-based culture was diluted 20-fold with water, and 5 µL of the diluted culture was mixed with 125 µL or 150 µL Infinity™ Glucose Hexokinase Liquid Stable Reagent (Thermo Fisher Scientific Inc.), both plus and minus the addition of 1 µL of a 20 g/L Maxinvert® 200000 MG (DSM Food Specialties) invertase solution. Both reaction mixtures were incubated at room temperature for approximately 1 h, at which point their absorbances at 340 nm were measured. Glucose standards were included in the assay to generate a linear correlation between different glucose concentrations and their absorbance measurements at 340 nm to facilitate calculation of the residual glucose (g/L) in each test mixture. For each culture, the residual sucrose concentration (g/L) was obtained by subtracting the residual glucose concentration of the reaction mixture without the added invertase from the residual glucose concentration of the reaction mixture with the added invertase, dividing this difference by 180.16 (molecular weight of glucose), and then multiplying by 342.3 (molecular weight of sucrose). The amount of sucrose hydrolyzed (g/L) during the fermentation period was determined by subtracting the residual sucrose concentration of the test culture from that of the medium control (approximately 55 g/L). With the YSI biochemistry analyzer, each sucrose-based culture was first diluted with an equal volume of water and pelleted by centrifugation. The residual sucrose and glucose concentrations of the resulting supernatant were then measured according to the instructions in the user's manual.

Mutant clones with significantly lower residual sucrose concentrations in their sucrose-based cultures (hence higher percentage of sucrose inverted) than the controls expressing one copy of the wild-type ScSUC2 gene at the targeted locus of integration were identified as potential hits. The ScSUC2 variant genes harbored by these clones were PCR-amplified from their genomic DNA and sequenced to identify the causative mutations that led to their increase in sucrose hydrolytic activity using techniques familiar to those skilled in the art. Clones harboring more than one ScSUC2 variant gene according to the sequencing data were eliminated from further evaluation.

Results

Beneficial Mutations Isolated from the Saturation Mutagenesis

Figure 2:
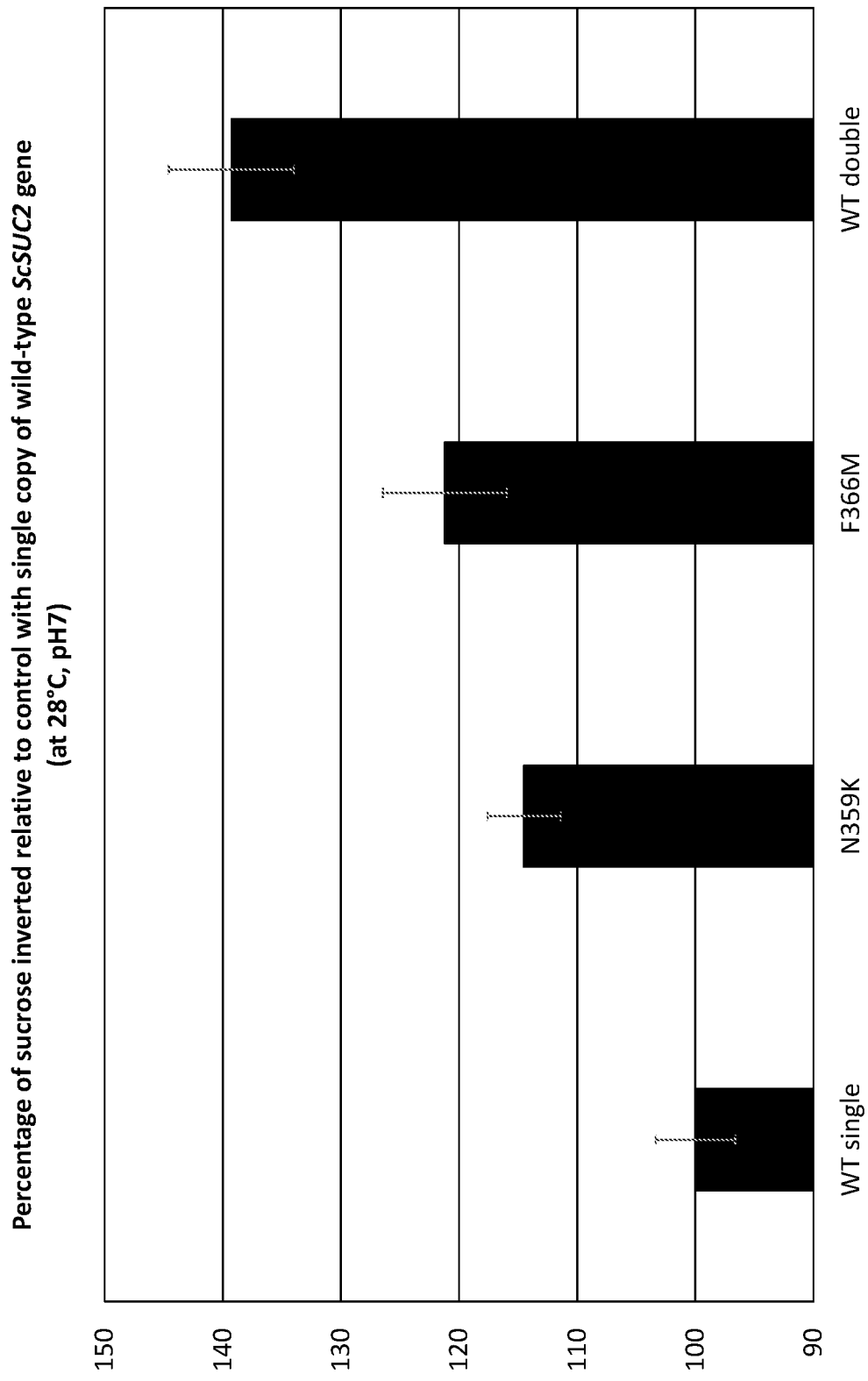
FIG. 2: Sucrose hydrolytic activity of two ScSUC2 variants (N359K and F366M) at pH 7, 28° C. For comparison, controls with single copy and double copies of the wild-type ScSUC2 gene were included. Assay conditions are described in Example 1. Outliers are omitted from the calculations.

Four beneficial mutations were identified from the ScSUC2 saturation mutagenesis libraries. These include an isoleucine-to-cysteine mutation at amino-acid position 17 (I17C, SEQ ID NO:2), which is located within the predicted transit peptide (amino acid 1-19) of the ScSUC2 enzyme. They also include an arginine-to-valine mutation at amino-acid position 28 (R28V, SEQ ID NO: SEQ ID NO:3), an asparagine-to-lysine mutation at amino-acid position 359 (N359K, SEQ ID NO:4), and a phenylalanine-to-methionine mutation at amino-acid position 366 (F366M, SEQ ID NO:5), which are located within the mature enzyme. As shown in FIGS. 1 and 2, the expression of each of these ScSUC2 variants increased sucrose hydrolysis (as represented by the amount of sucrose inverted in the sucrose-based cultures) by 15-21% compared to the expression of a single copy of the wild-type ScSUC2 gene. For reference, the expression of two copies of the wild-type ScSUC2 gene (one copy at each allele of the targeted locus) increased sucrose hydrolysis by approx. 36-39%.

Figure 3A:
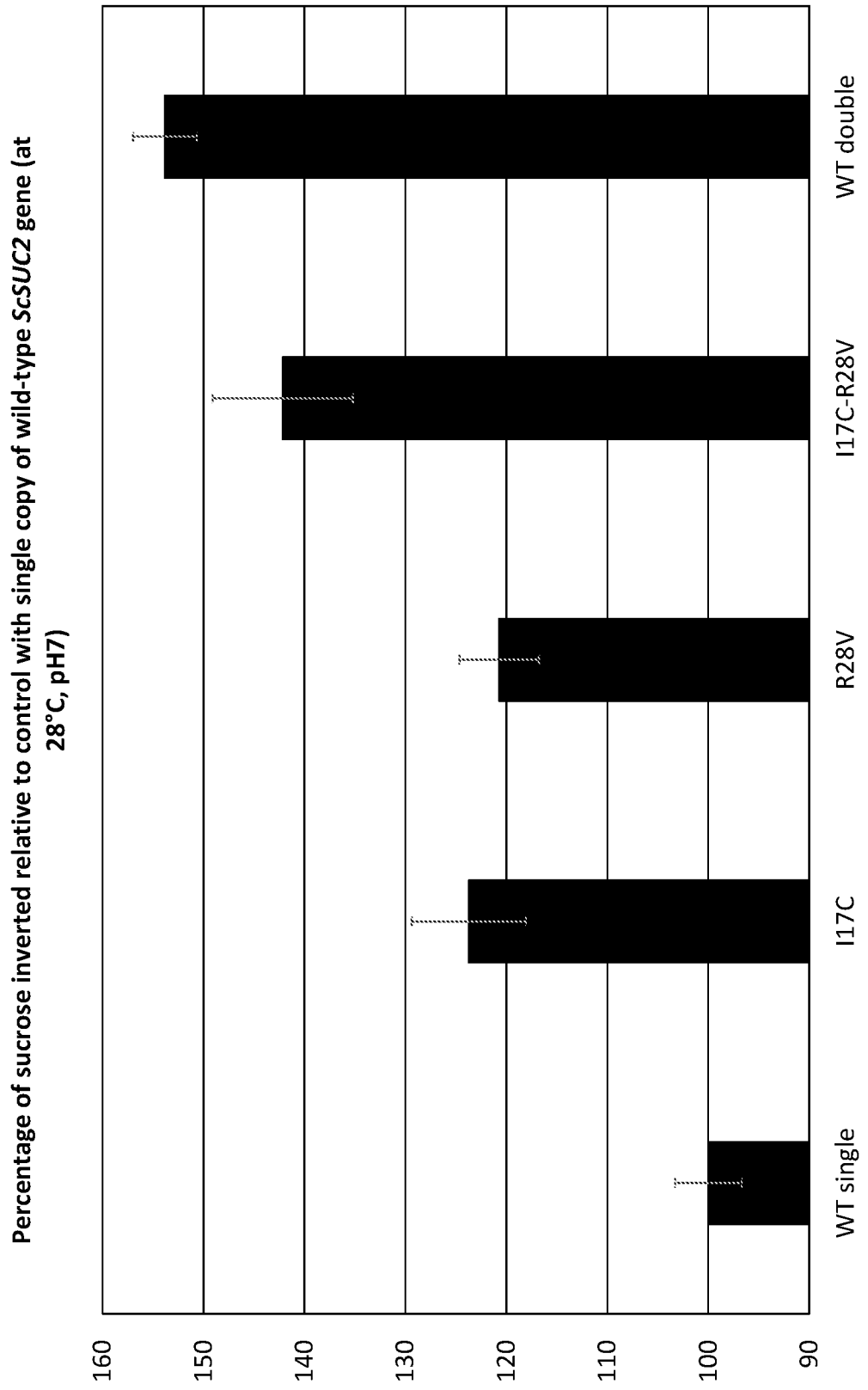
FIG. 3A-3B: Sucrose hydrolytic activity of three ScSUC2 variants (I17C, R28V, and I17C-R28V) at (A) pH 7, 28° C. and (B) pH 7, 32° C. For comparison, controls with single copy and double copies of the wild-type ScSUC2 gene were included. Assay conditions are described in Example 1. Outliers are omitted from the calculations.
Figure 3B:
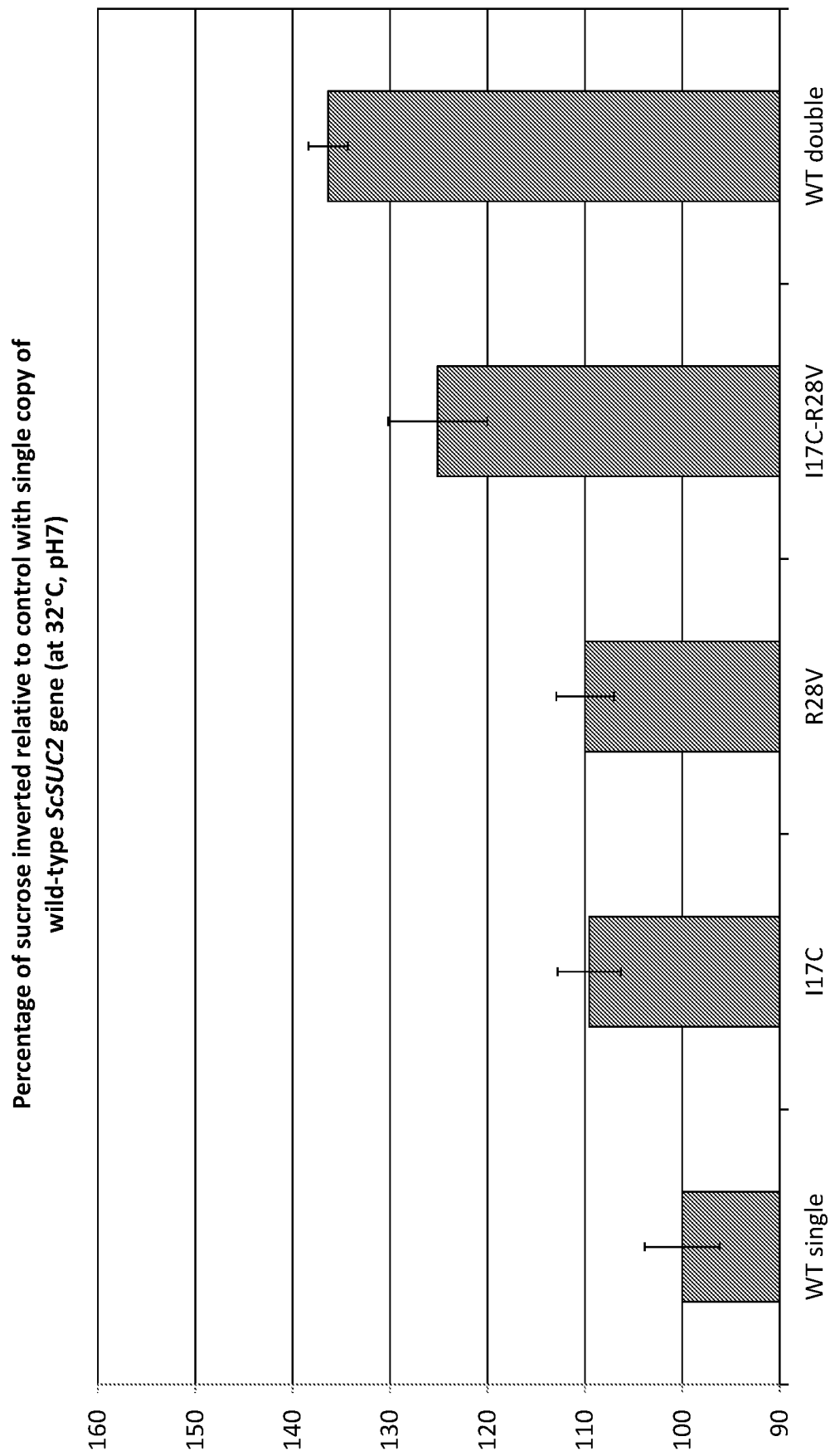
Figure 4A:
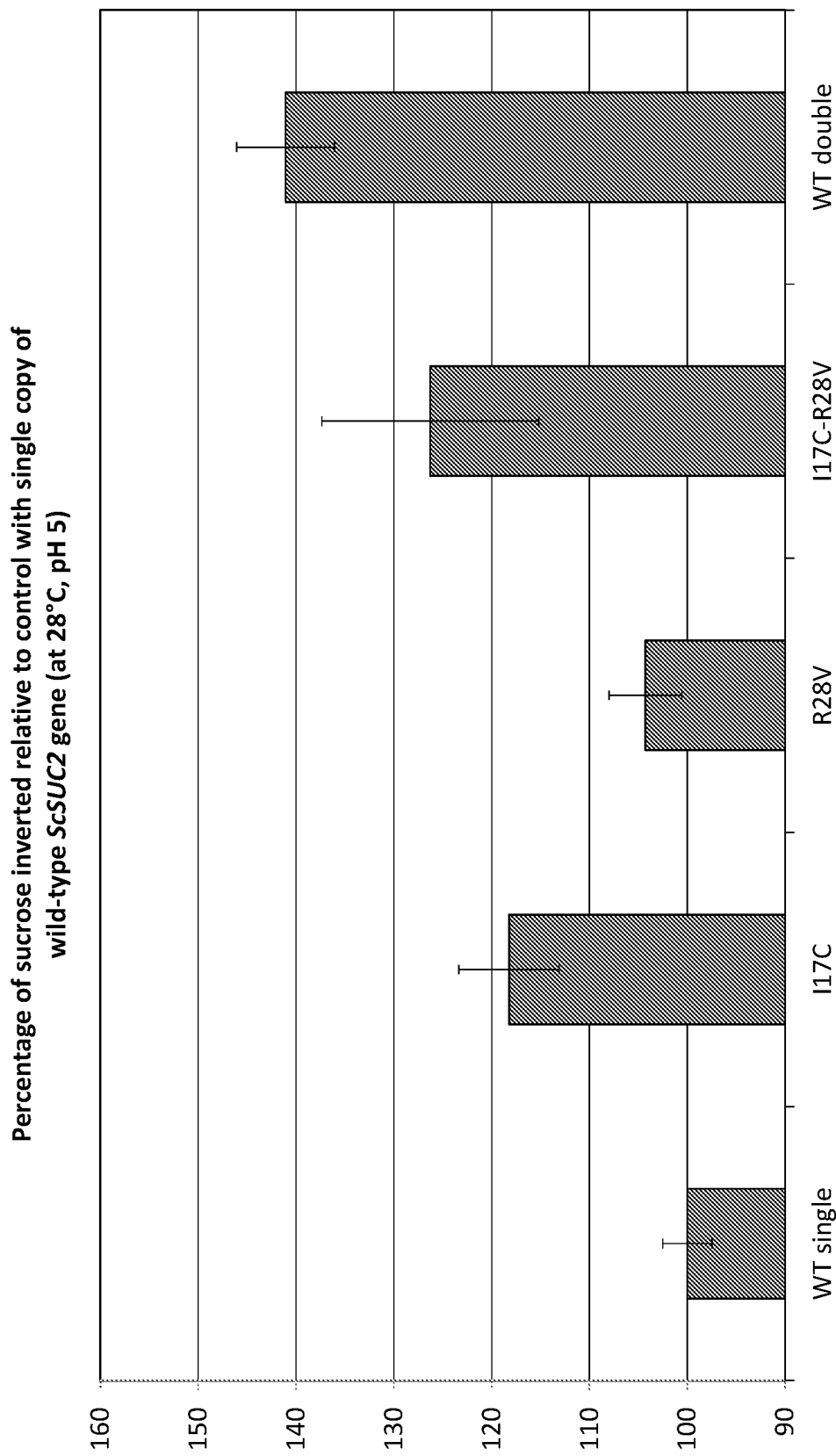
FIG. 4A-4B: Sucrose hydrolytic activity of three ScSUC2 variants (I17C, R28V, and I17C-R28V) at (A) pH 5, 28° C. and (B) pH 5, 32° C. For comparison, controls with single copy and double copies of the wild-type ScSUC2 gene were included. Assay conditions are described in Example 1. Outliers are omitted from the calculations.
Figure 4B:
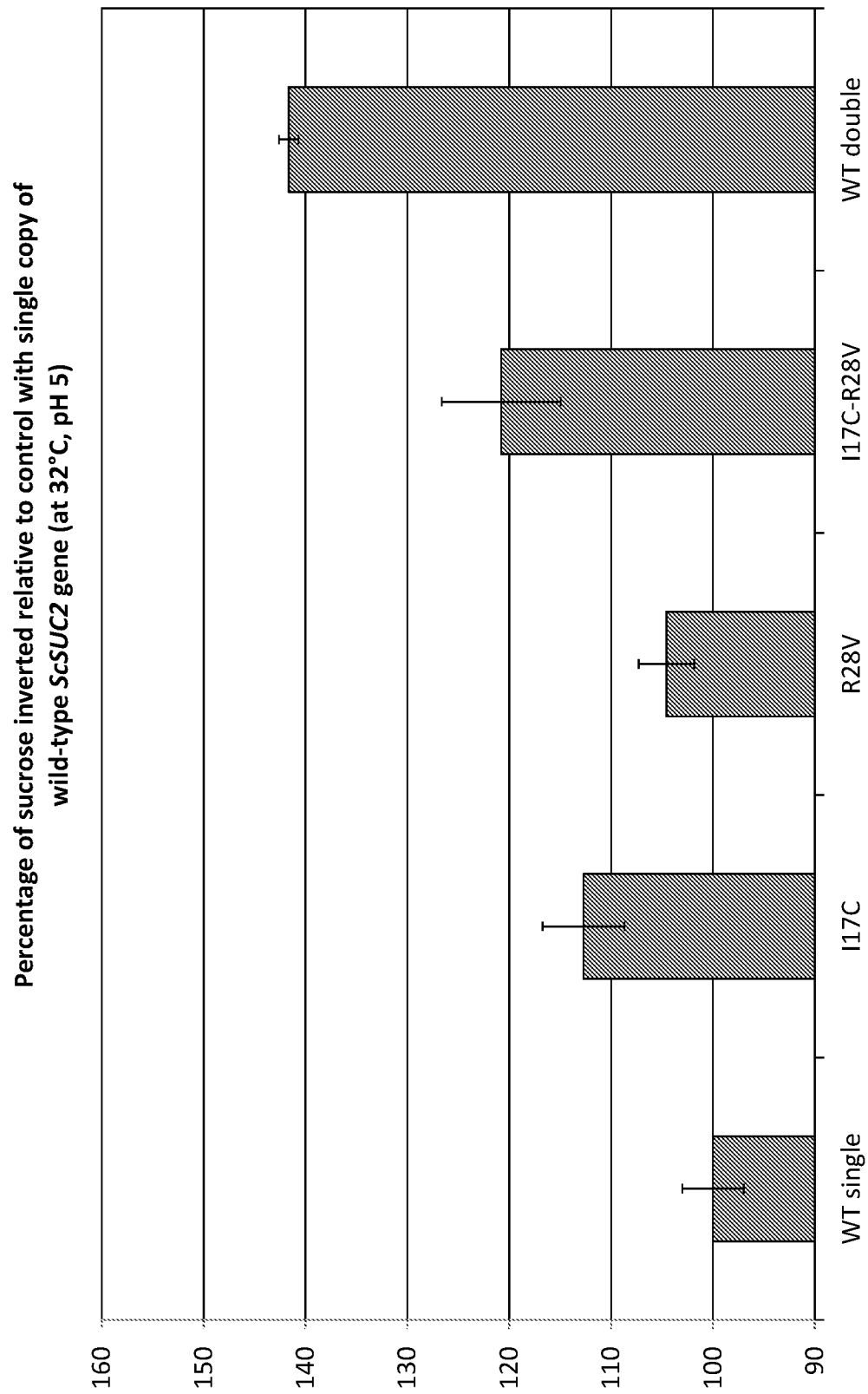

Combining the I17C and R28V Mutations to Further Increase Sucrose Hydrolytic Activity In an effort to further enhance the sucrose hydrolytic activity of the ScSUC2 enzyme, the I17C and R28V mutations were combined together (SEQ ID NO:6) and cloned into the algal expression vector (construct pSZ6857, SEQ ID NO: 14) using techniques familiar to those skilled in the art. For comparison, they were also re-cloned as single mutations into the same expression vector (construct pSZ6703, SEQ ID NO:12 and pSZ6698, SEQ ID NO:13). Each of the resulting constructs was transformed into strain S7485. For each construct, six to twelve clonally-purified transformants expressing only one copy of the ScSUC2 variant gene were selected for evaluation using the assays described above. As shown in FIG. 3, the ScSUC2 variant that harbors both mutations (I17C-R28V) exhibited higher sucrose hydrolytic activity than either of the single-mutation variants (I17C or R28V) at pH 7 and 28° C. On average, its expression increased the amount of inverted sucrose in the sucrose-based cultures by 41% compared to the expression of a single copy of the wild-type ScSUC2 gene. In fact, the sucrose hydrolytic activity of the $ScSUC2^{I17C-R28V}$ variant approached that achieved by the double-copy, wild-type ScSUC2 control. Similar improvements in sucrose hydrolysis were observed when the three ScSUC2 variants were tested at the higher temperature of 32° C. (FIG. 3). They also showed increased sucrose hydrolytic activity compared to the single-copy, wild-type control when evaluated at the lower pH of 5 (FIG. 4). Our results indicate that the $ScSUC2^{I17C-R28V}$ variant consistently out-performed the $ScSUC2^{I17C}$ and $ScSUC2^{R28V}$ variants under all four test conditions.

Two Mutations Confirmed to Further Increase Sucrose Hydrolytic Activity when Combined with the I17C-R28V Double Mutations Given these promising results, the other two beneficial mutations identified from the saturation mutagenesis libraries (N359K and F366M) were added to the $ScSUC2^{I17C-R28V}$ variant either individually or in combination using techniques familiar to those skilled in the art. The resulting variants—$ScSUC2^{I17C-R28V-N359K}$ (SEQ ID NO:7), $ScSUC2^{I17C-R28V-F366M}$ (SEQ ID NO:8), and $ScSUC2^{I17C-R28V-N359K-F366M}$ (SEQ ID NO:9)—were cloned into the algal expression vector to generate constructs pSZ6897 (SEQ ID NO:15), pSZ6899 (SEQ ID NO:16), and pSZ6917 (SEQ ID NO:17), respectively, which were each transformed into strain S7485. For each construct, six to twelve clonally-purified transformants expressing only one copy of the ScSUC2 variant gene were selected for evaluation using the assays described above.

Figure 5:
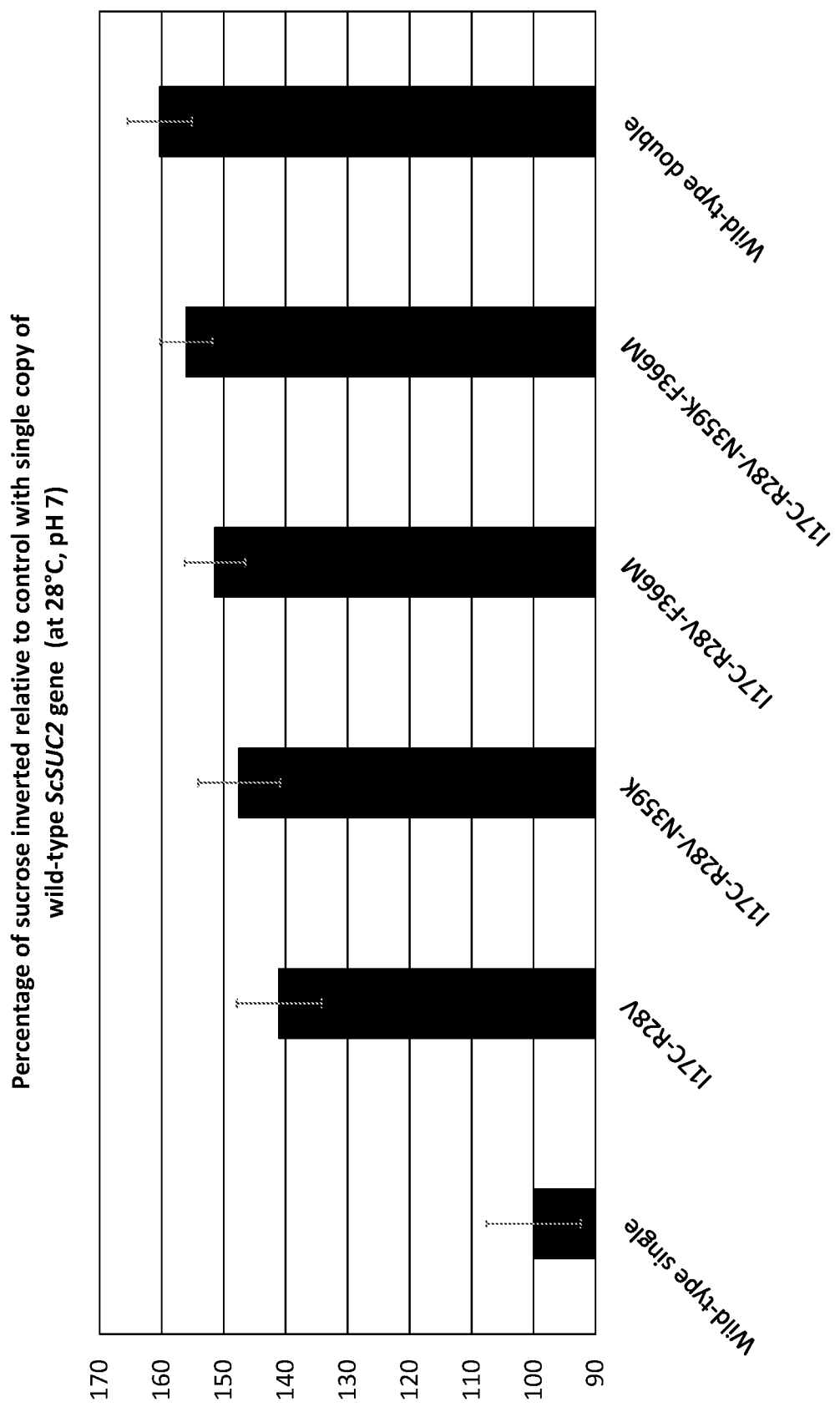
FIG. 5: Sucrose hydrolytic activity of four ScSUC2 variants (I17C-R28V, I17C-R28V-N359K, I17C-R28V-F366M and I17C-R28V-N359K-F366M) at pH 7, 28° C. For comparison, controls with single copy and double copies of the wild-type ScSUC2 gene were included. Assay conditions are described in Example 1. Outliers are omitted from the calculations.
Figure 6:
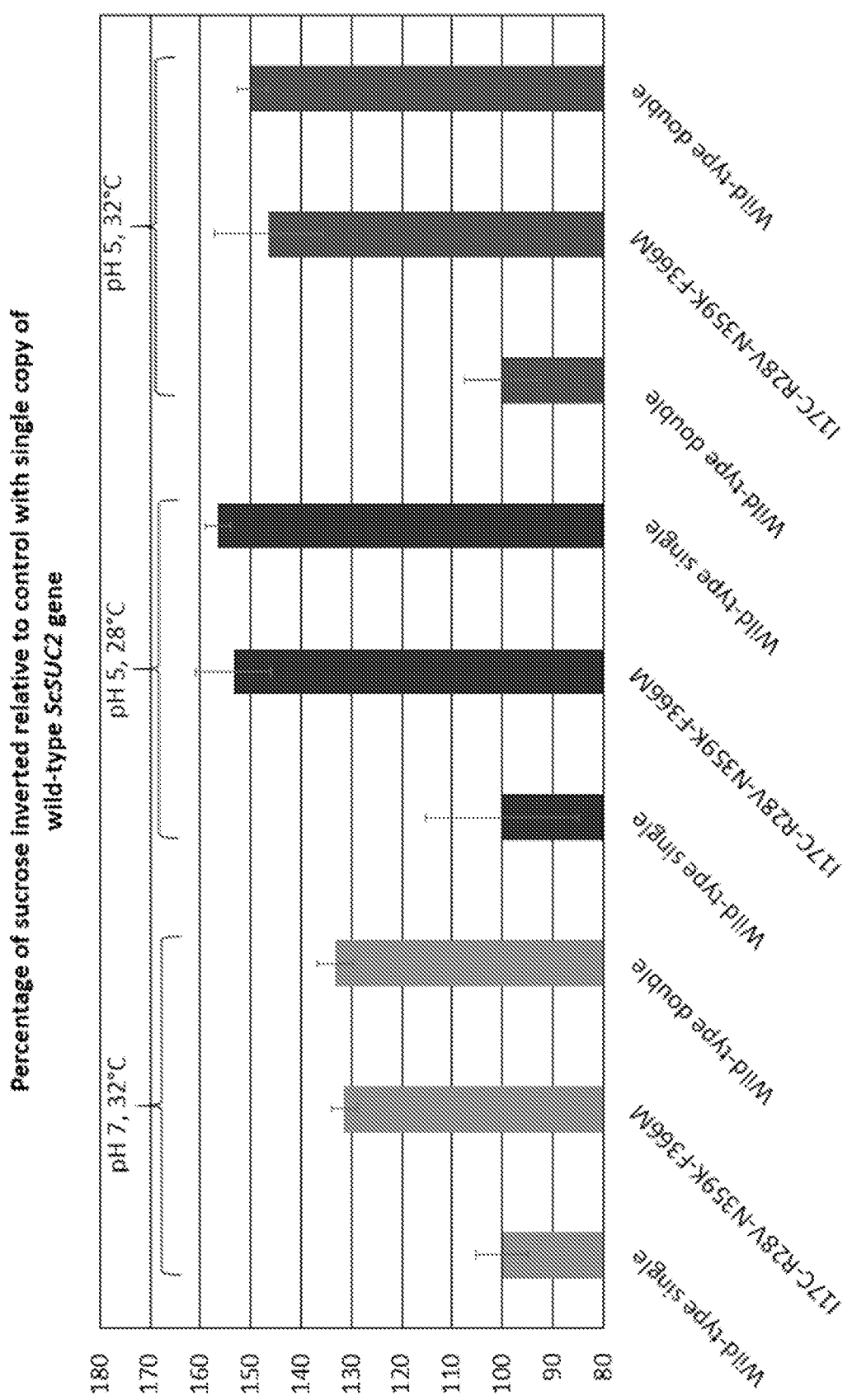
FIG. 6: Effect of pH and temperature on the sucrose hydrolysis activity of ScSUC2 variant (I17C-R28V-N359K-F366M). For comparison, controls with single copy and double copies of the wild-type ScSUC2 gene were included. Assay conditions are described in Example 1. Outliers are omitted from the calculations.

As shown in FIG. 5, both the N359K and F366M mutations further increased the sucrose hydrolytic activity of the ScSUC2 invertase, when they were individually combined with the I17C-R28V double mutation. At pH 7 and 28° C., expression of the $ScSUC2^{I17C-R28V-N359K}$ or $ScSUC2^{I17C-R28V-F366M}$ variant on average increased the amount of inverted sucrose in the sucrose-based cultures by 48-51% compared to the expression of a single copy of the wild-type ScSUC2 gene. When all four mutations were combined together, the resulting $ScSUC2^{I17C-R28V-N359K-F366M}$ variant exhibited sucrose hydrolytic activity that was on average 56% higher than that observed for the single-copy, wild-type ScSUC2 control. Moreover, this activity is now comparable to that achieved by the double-copy, wild-type ScSUC2 control. Similar experiments carried out at pH 5 and/or 32° C. also showed that the $ScSUC2^{I17C-R28V-N359K-F366M}$ variant can invert sucrose as efficiently as the double-copy, wild-type ScSUC2 control under these test conditions (FIG. 6). Together, the above results confirm the improved invertase activity of the $ScSUC2^{I17C-R28V-N359K-F366M}$ variant and highlight its utility in providing sufficient sucrose hydrolysis for consumption by *P. moriformis* in fermentations conducted at pH 7.

The wild-type sucrose invertase (ScSUC2) expressed in *Prototheca moriformis* strains to enable the hydrolysis of sucrose to glucose and fructose for consumption by the cells during fermentation. However, because ScSUC2 activity is optimal at pH 4.5 and decreases with increasing pH, fermentations conducted at pH 7 require the addition of a significant amount of exogenous invertase to ensure sufficient sucrose hydrolysis. Since the optimal culture condition for achieving maximal production of a product of interest by the host cells may be at pH 7 or other neutral pH, the identification of a sucrose invertase variant that is more active at pH 7 or other neutral pH can reduce or eliminate the need for addition of exogenous sucrose invertase addition, which can lower overall production costs.

Nucleic Acid Sequence of Construct pSZ6917 (SEQ ID NO:1c) for the Expression of *S. cerevisiae* $SUC2^{I17C-R28V-N359K-F366M}$ ($ScSUC2^{I17C-R28V-N359K-F366M}$) in *P. moriformis* (Table 1).

Nonspecific or vector sequences are in plain uppercase. Relevant restriction sites (5' 3' 3' PmeI, KpnI, XbaI, MfeI, BamHI, SacI, and PmeI) are in bold, underlined lowercase. PmeI sites delimit the 5' and 3' ends of the transforming DNA. The 5' and 3' homology targeting arms for integration at the DAcgb locus are in bold lowercase. Proceeding in the 5' to 3' direction, the CrTUB2 promoter is in boxed, lowercase italics. The ScSUC2$^{I17C\text{-}R28V\text{-}NV359K\text{-}F366M}$ gene variant is bold, lowercase italics. The PmPGH 3'-UTR is in plain, underlined lowercase. The buffer DNA sequence that follows is in plain lowercase.

TABLE 1

AGCGGAAGAGCGCCCAATgtttaaacagcccgcaccctcgttgatctgggagccctgcgcagc cccttaaatcatctcagtcaggtttctgtgttcaactgagcctaaagggctttcgtcatgcgc acgagcacacgtatatcggccacgcagtttctcaaaagcggtagaacagttcgcgagccctcg taggtcgaaaacttgcgccagtactattaaattaaattaattgatcgaacgagacgcgaaact tttgcagaatgccaccgagtttgcccagagaatgggagtggcgccattcaccatccgcctgtg cccggcttgattcgccgagacgatggacggcgagaccagggagcggcttgcgagcccgagcc ggtagcaggaacaatgatcgacaatcttcctgtccaattactggcaaccattagaaagagccg gagcgcgttgaaagtctgcaatcgagtaattttcgatacgtcgggcctgctgaaccctaagg ctccggactttgtttaaggcgatccaagatgcacgcggccccaggcacgtatctcaagcacaa accccagccttagtttcgagactttgggagatagcgaccgatatctagtttggcattttgtat attaattacctcaagcaatggagcgctctgatgcggtgcagcgtcggctgcagcacctggcag tggcgctagggtcgccctatcgctcggaacctggtcagctggctcccgcctcctgctcagcct cttccggtacc<u>ctttcttgcgctatgacacttccagcaaaaggtagggcgggctgcgagacgg</u>

<u>cttcccggcgctgcatgcaacaccgatgatgcttcgaccccccgaagctccttcggggctgca</u>

<u>tgggcgctccgatgccgctccagggcgagcgctgtttaaatagccaggcccccgattgcaaag</u>

<u>acattatagcgagctaccaaagccatattcaaacacctagatcactaccacttctacacaggc</u>

<u>cactcgagcttgtgatcgcactccgctaagggggcgcctcttcctcttcgtttcagtcacaac</u>

<u>ccgcaaa</u>tctagaATATCA*atgctgctgcaggccttcctgttcctgctggccggcttcgccg*

*ccaagtgcagcgcctccatgacgaacgagacgtccgacgtgcccctggtgcacttcaccccca*

*acaagggctggatgaacgaccccaacggcctgtggtacgacgagaaggacgccaagtggcacc*

*tgtacttccagtacaacccgaacgacaccgtctgggggacgcccttgttctggggccacgcca*

*cgtccgacgacctgaccaactgggaggaccagcccatcgccatcgccccgaagcgcaacgact*

*ccggcgccttctccggctccatggtggtggactacaacaacacctccggcttcttcaacgaca*

*ccatcgacccgcgccagcgctgcgtggccatctggacctacaacaccccggagtccgaggagc*

*ahyacatctcctacagcctggacggcggctacaccttcaccgagtaccagaagaaccccgtgc*

*tggccgccaactccacccagttccgcgacccgaaggtcttctggtacgagccctcccagaagt*

*ggatcatgaccgcggccaagtcccaggactacaagatcgagatctactcctccgacgacctga*

*agtcctggaagctggagtccgcgttcgccaacgagggcttcctcggctaccagtacgagtgcc*

*ccggcctgatcgaggtccccaccgagcaggaccccagcaagtcctactgggtgatgttcatct*

TABLE 1-continued

*ccatcaaccccggcgcccggccggcggctccttcaaccagtacttcgtcggcagcttcaacg*

*gcacccacttcgaggccttcgacaaccagtcccgcgtggtggacttcggcaaggactactacg*

*ccctgcagaccttcttcaacaccgacccgacctacgggagcgccctgggcatcgcgtgggcct*

*ccaactggagtactccgccttcgtgccaccaacccctggcgctcctccatgtccctcgtgc*

*gcaagttctccctcaacaccgagtaccaggccaacccggagacggagctgatcaacctgaagg*

*ccgagccgatcctgaacatcagcaaggccggccctggagccggatggccaccaacaccacgt*

*tgacgaaggccaacagctacaacgtcgacctgtccaacagcaccggcaccctggagttcgagc*

*tggtgtacgccgtcaacaccacccagacgatctccaagtccgtgttcgcggacctctccctct*

*ggttcaagggcctggaggaccccgaggagtacctccgcatgggcttcgaggtgtccgcgtcct*

*ccttcttcctggaccgcgggaacagcaaggtgaagttcgtgaaggagaacccctacttcacca*

*accgcatgagcgtgaacaaccagcccttcaagagcgagaacgacctgtcctactacaaggtgt*

*acggcttgctggaccagaacatcctggagctgtacttcaacgacggcgacgtcgtgtccacca*

*acacctacttcatgaccaccgggaacgccctgggctccgtgaacatgacgacggggtggaca*

*acctgttctacatcgacaagttccaggtgcgcgaggtcaagtgacaattg*acgcccgcgcggc gcacctgacctgttctctcgagggcgcctgttctgccttgcgaaacaagcccctggagcatgc
gtgcatgatcgtctctggcgccccgccgcgcggtttgtcgccctcgcggggcgccgcggccgcg
ggggcgcattgaaattgttgcaaaccccacctgacagattgagggcccaggcaggaaggcgtt
gagatggaggtacaggagtcaagtaactgaaagtttttatgataactaacaacaaagggtcgt
ttctggccagcgaatgacaagaacaagattccacatttccgtgtagaggcttgccatcgaatg
tgagcgggcgggccgcggacccgacaaaacccttacgacgtggtaagaaaaacgtggcgggca
ctgtccctgtagcctgaagaccagcaggagacgatcggaagcatcacagcacaggatcccgcg
tctcgaacagagcgcgcagaggaacgctgaaggtctcgcctctgtcgcacctcagcgcggcat
acaccacaataaccacctgacgaatgcgcttggttcttcgtccattagcgaagcgtccggttc
acacacgtgccacgttggcgaggtggcaggtgacaatgatcggtggagctgatggtcgaaacg
ttcacagcctaggATCGAGTGTACAGTCAATGAATGGTgagctcagcgtctgcgtgttgggag
ctggagtcgtgggcttgacgacggcgctgcagctgttgcaggatgtgcctggcgtgcgcgttc
acgtcgtggctgagaaatatggcgacgaaacgttgacggctggggccggcgggctgtggatgc
catacgcattgggtacgcggccattggatgggattgataggcttatggagggataatagagtt
tttgccggatccaacgcatgtggatgcggtatcccggtgggctgaaagtgtggaaggatagtg
cattggctattcacatgcactgcccacccctttttggcaggaaatgtgccggcatcgttggtgc
accgatggggaaaatcgacgttcgaccactacatgaagatttatacgtctgaagatgcagcga
ctgcgggtgcgaaacggatgacggtttggtcgtgtatgtcacagcatgtgctggatcttgcgg
gctaactccccctgccacggcccattgcaggtgtcatgttgactggagggtacgacctttcgt TABLE 1-continued

```
ccgtcaaattcccagaggaggacccgctctgggccgacattgtgcccactGAAGAGCgtttaa
acCGCCTCTCCCCGCGCGTTGGCCGATTCATTAATGCAGCTGGCACGACAGGTTTCCCGACTG
GAAAGCGGGCAGTGAGCGCAACGCAATTAATGTGAGTTAGCTCACTCATTAGGCACCCCAGGC
TTTACACTTTATGCTTCCGGCTCGTATGTTGTGTGGAATTGTGAGCGGATAACAATTTCACAC
AGGAAACAGCTATGACCATGATTACGCCAAGCTCGAAATTAACCCTCACTAAAGGGAACAAAA
GCTGGCCAATTCGCCCTATAGTGAGTCGTATTACAATTCACTGGCCGTCGTTTTACAACGTCG
TGACTGGGAAAACCCTGGCGTTACCCAACTTAATCGCCTTGCAGCACATCCCCCTTTCGCCAG
CTGGCGTAATAGCGAAGAGGCCCGCACCGATCGCCCTTCCCAACAGTTGCGCAGCCTGAATGG
CGAATGGGACGCGCCCTGTAGCGGCGCATTAAGCGCGGCGGGTGTGGTGGTTACGCGCAGCGT
GACCGCTACACTTGCCAGCGCCCTAGCGCCCGCTCCTTTCGCTTTCTTCCCTTCCTTTCTCGC
CACGTTCGCCGGCTTTCCCCGTCAAGCTCTAAATCGGGGGCTCCCTTTAGGGTTCCGATTTAG
TGCTTTACGGCACCTCGACCCCAAAAAACTTGATTAGGGTGATGGTTCACGTAGTGGGCCATC
GCCCTGATAGACGGTTTTTCGCCCTTTGACGTTGGAGTCCACGTTCTTTAATAGTGGACTCTT
GTTCCAAACTGGAACAACACTCAACCCTATCTCGGTCTATTCTTTTGATTTATAAGGGATTTT
GCCGATTTCGGCCTATTGGTTAAAAAATGAGCTGATTTAACAAAAATTTAACGCGAATTTTAA
CAAAATATTAACGCTTACAATTTAGGTGGCACTTTTCGGGGAAATGTGCGCGGAACCCCTATT
TGTTTATTTTTCTAAATACATTCAAATATGTATCCGCTCATGAGACAATAACCCTGATAAATG
CTTCAATAATATTGAAAAAGGAAGAGTATGAGTATTCAACATTTCCGTGTCGCCCTTATTCCC
TTTTTTGCGGCATTTTGCCTTCCTGTTTTTGCTCACCCAGAAACGCTGGTGAAAGTAAAAGAT
GCTGAAGATCAGTTGGGTGCACGAGTGGGTTACATCGAACTGGATCTCAACAGCGGTAAGATC
CTTGAGAGTTTTCGCCCCGAAGAACGTTTTCCAATGATGAGCACTTTTAAAGTTCTGCTATGT
GGCGCGGTATTATCCCGTATTGACGCCGGGCAAGAGCAACTCGGTCGCCGCATACACTATTCT
CAGAATGACTTGGTTGAGTACTCACCAGTCACAGAAAAGCATCTTACGGATGGCATGACAGTA
AGAGAATTATGCAGTGCTGCCATAACCATGAGTGATAACACTGCGGCCAACTTACTTCTGACA
ACGATCGGAGGACCGAAGGAGCTAACCGCTTTTTTGCACAACATGGGGGATCATGTAACTCGC
CTTGATCGTTGGGAACCGGAGCTGAATGAAGCCATACCAAACGACGAGCGTGACACCACGATG
CCTGTAGCAATGGCAACAACGTTGCGCAAACTATTAACTGGCGAACTACTTACTCTAGCTTCC
CGGCAACAATTAATAGACTGGATGGAGGCGGATAAAGTTGCAGGACCACTTCTGCGCTCGGCC
CTTCCGGCTGGCTGGTTTATTGCTGATAAATCTGGAGCCGGTGAGCGTGGGTCTCGCGGTATC
ATTGCAGCACTGGGGCCAGATGGTAAGCCCTCCCGTATCGTAGTTATCTACACGACGGGGAGT
CAGGCAACTATGGATGAACGAAATAGACAGATCGCTGAGATAGGTGCCTCACTGATTAAGCAT
TGGTAACTGTCAGACCAAGTTTACTCATATATACTTTAGATTGATTTAAAACTTCATTTTTAA
TTTAAAAGGATCTAGGTGAAGATCCTTTTTGATAATCTCATGACCAAAATCCCTTAACGTGAG
TTTTCGTTCCACTGAGCGTCAGACCCCGTAGAAAAGATCAAAGGATCTTCTTGAGATCCTTTT
TTTCTGCGCGTAATCTGCTGCTTGCAAACAAAAAAACCACCGCTACCAGCGGTGGTTTGTTTG
CCGGATCAAGAGCTACCAACTCTTTTTCCGAAGGTAACTGGCTTCAGCAGAGCGCAGATACCA
AATACTGTCCTTCTAGTGTAGCCGTAGTTAGGCCACCACTTCAAGAACTCTGTAGCACCGCCT
ACATACCTCGCTCTGCTAATCCTGTTACCAGTGGCTGCTGCCAGTGGCGATAAGTCGTGTCTT
ACCGGGTTGGACTCAAGACGATAGTTACCGGATAAGGCGCAGCGGTCGGGCTGAACGGGGGGT
TCGTGCACACAGCCCAGCTTGGAGCGAACGACCTACACCGAACTGAGATACCTACAGCGTGAG
```

TABLE 1-continued

```
CTATGAGAAAGCGCCACGCTTCCCGAAGGGAGAAAGGCGGACAGGTATCCGGTAAGCGGCAGG

GTCGGAACAGGAGAGCGCACGAGGGAGCTTCCAGGGGGAAACGCCTGGTATCTTTATAGTCCT

GTCGGGTTTCGCCACCTCTGACTTGAGCGTCGATTTTTGTGATGCTCGTCAGGGGGGCGGAGC

CTATGGAAAAACGCCAGCAACGCGGCCTTTTTACGGTTCCTGGCCTTTTGCTGGCCTTTTGCT

CACATGTTCTTTCCTGCGTTATCCCCTGATTCTGTGGATAACCGTATTACCGCCTTTGAGTGA

GCTGATACCGCTCGCCGCAGCCGAACGACCGAGCGCAGCGAGTCAGTGAGCGAGGA
```

What is claimed is:

1. A sucrose invertase variant comprising a polypeptide sequence having at least 80%, 85%, 90%, 91%, 92%, 93%, 94%, 95%, 96%, 97%, 98%, or 99% amino acid sequence identity to: (i) a full-length wild-type *Saccharomyces cerevisiae* sucrose invertase having the amino acid sequence of SEQ ID NO: 1 or (ii) SEQ ID NO:1 lacking the first 19 amino acids, wherein the sucrose invertase variant comprises a modification comprising at least one amino acid substitution in at least one amino acid residue position selected from the group consisting of positions 17, 28, 359, and 366, wherein the amino acid residue positions correspond to amino acid residues numbered from the N-terminus of SEQ ID NO:1, wherein the one or more amino acid substitutions are selected from the group consisting of:

(a) an amino acid substitution from isoleucine to a hydroxyl- or sulfur-containing amino acid at amino acid residue position 17;
(b) an amino acid substitution from arginine to an aliphatic or sulfur-containing amino acid at amino acid residue position 28;
(c) an amino acid substitution from asparagine to a basic amino acid at amino acid residue position 359; and
(d) an amino acid substitution from phenylalanine to a sulfur-containing or aliphatic amino acid at amino acid residue position 366.

2. The sucrose invertase variant of claim 1, wherein the one or more amino acid substitutions are selected from the group consisting of:

(a) an amino acid substitution from isoleucine to cysteine at amino acid residue position 17 (I17C);
(b) an amino acid substitution from arginine to valine at amino acid residue position 28 (R28V);
(c) an amino acid substitution from asparagine to lysine at amino acid residue position 359 (N359K); and
(d) an amino acid substitution from phenylalanine to methionine at amino acid residue position 366 (F366M).

3. The sucrose invertase variant of claim 1, wherein the one or more amino acid substitutions comprises an amino acid substitution at amino acid residue position 17.

4. The sucrose invertase variant of claim 3, wherein the amino acid substitution at amino acid residue position 17 is an amino acid substitution from isoleucine to cysteine (I17C).

5. The sucrose invertase variant of claim 1, wherein the one or more amino acid substitutions comprises an amino acid substitution at amino acid residue position 28.

6. The sucrose invertase variant of claim 5, wherein the amino acid substitution at amino acid residue position 28 is an amino acid substitution from arginine to valine (R28V).

7. The sucrose invertase variant of claim 5, wherein the one or more amino acid substitutions comprises an amino acid substitution at amino acid residue position 359.

8. The sucrose invertase variant of claim 7, wherein the amino acid substitution at amino acid residue position 359 is an amino acid substitution from asparagine to lysine (N359K).

9. The sucrose invertase variant of claim 1, wherein the one or more amino acid substitutions comprises an amino acid substitution at amino acid residue position 366.

10. The sucrose invertase variant of claim 9, wherein the amino acid substitution at amino acid residue position 366 is from phenylalanine to methionine (F366M).

11. The sucrose invertase variant of claim 1, wherein the variant comprises at least two amino acid substitutions at residue positions selected from the group consisting of positions 17, 28, 359, and 366.

12. The sucrose invertase variant of claim 11, wherein the at least two amino acid substitutions comprise amino acid substitutions at a pair of amino acid residue positions selected from the group consisting of:
(a) 17 and 28;
(b) 17 and 359;
(c) 17 and 366;
(d) 28 and 359;
(e) 28 and 366; and
(f) 359 and 366.

13. The sucrose invertase variant of claim 1, wherein the sucrose invertase variant comprises at least three amino acid substitutions at residue positions selected from the group consisting of positions 17, 28, 359, and 366.

14. The sucrose invertase variant of claim 1, wherein the sucrose invertase variant comprises at least four amino acids substitutions at residue positions selected from the group consisting of positions 17, 28, 359, and 366.

15. The sucrose invertase variant of claim 1, wherein the amino acid sequence identity is at least 95%, 96%, 97%, or 99%, or optionally wherein the sucrose invertase variant comprises:
(a) an amino acid sequence of SEQ ID NO:2, or a subsequence of SEQ ID NO: 2 that lacks predicted transit peptide amino acid residues 1-19 of SEQ ID NO:2;
(b) an amino acid sequence of SEQ ID NO:3, or a subsequence of SEQ ID NO: 3 that lacks predicted transit peptide amino acid residues 1-19 of SEQ ID NO:3;
(c) an amino acid sequence of SEQ ID NO:4, or a subsequence of SEQ ID NO: 4 that lacks predicted transit peptide amino acid residues 1-19 of SEQ ID NO:4;
(d) an amino acid sequence of SEQ ID NO: 5, or a subsequence of SEQ ID NO: 5 that lacks predicted transit peptide amino acid residues 1-19 of SEQ ID NO:5;
(e) an amino acid sequence of SEQ ID NO:6, or a subsequence of SEQ ID NO: 6 that lacks predicted transit peptide amino acid residues 1-19 of SEQ ID NO:6;
(f) an amino acid sequence of SEQ ID NO: 7, or a subsequence of SEQ ID NO: 7 that lacks predicted transit peptide amino acid residues 1-19 of SEQ ID NO:7;
(g) an amino acid sequence of SEQ ID NO:8, or a subsequence of SEQ ID NO: 8 that lacks predicted transit peptide amino acid residues 1-19 of SEQ ID NO:8; or
(h) an amino acid sequence of SEQ ID NO:9, or a subsequence of SEQ ID NO: 9 that lacks predicted transit peptide amino acid residues 1-19 of SEQ ID NO:9.

16. The sucrose invertase variant of claim 1, wherein the sucrose invertase variant has an enhanced ability to hydrolyze sucrose into glucose and fructose at pH 7, as compared to an unmodified form of the full-length wild-type *Saccharomyces cerevisiae* sucrose invertase variant having the amino acid sequence of SEQ ID NO:1.

17. A polynucleotide comprising a nucleotide sequence encoding the sucrose invertase variant of claim 1.

18. The polynucleotide of claim 17, wherein the nucleotide sequence identity is at least 95%, 96%, 97%, 98%, or 99% identical to a nucleotide sequence selected from the group consisting of:
(a) the nucleotide sequence of SEQ ID NO:11;
(b) the nucleotide sequence of SEQ ID NO:12;
(c) the nucleotide sequence of SEQ ID NO:13;
(d) the nucleotide sequence of SEQ ID NO:14;
(e) the nucleotide sequence of SEQ ID NO:15;
(f) the nucleotide sequence of SEQ ID NO:16;
(g) the nucleotide sequence of SEQ ID NO:17; or
(h) the nucleotide sequence of SEQ ID NO:18.

19. An expression construct comprising the polynucleotide of claim 17 wherein the polynucleotide is operably linked to a promoter, or an engineered cell comprising the polynucleotide of claim 17,
optionally wherein the engineered cell comprises two or more copies of the polynucleotide of claim 17.

* * * * *

UNITED STATES PATENT AND TRADEMARK OFFICE
CERTIFICATE OF CORRECTION

| | | |
|---|---|---|
| PATENT NO. | : 12,338,468 B2 | Page 1 of 1 |
| APPLICATION NO. | : 17/777711 | |
| DATED | : June 24, 2025 | |
| INVENTOR(S) | : Nien-Hsi Ko, Janice Lau Wee and Douglas A. Hattendorf | |

It is certified that error appears in the above-identified patent and that said Letters Patent is hereby corrected as shown below:

In the Claims

In Claim 2, Column 79, Line 65, please replace "(117C)" with "(I17C)".

In Claim 7, Column 80, Line 53, please replace "claim 5" with "claim 1".

Signed and Sealed this
Twenty-first Day of October, 2025

John A. Squires
*Director of the United States Patent and Trademark Office*